United States Patent
Yu

(10) Patent No.: US 10,796,787 B2
(45) Date of Patent: *Oct. 6, 2020

(54) METHOD FOR IDENTIFYING ANTIGEN-SPECIFIC T CELL RECEPTORS IN PRIMATE

(71) Applicant: Qyuns Therapeutics Co.,Ltd., Taizhou (CN)

(72) Inventor: Guo-liang Yu, Hillsborough, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/021,024

(22) Filed: Jun. 28, 2018

(65) Prior Publication Data

US 2018/0322244 A1 Nov. 8, 2018

Related U.S. Application Data

(62) Division of application No. 15/208,850, filed on Jul. 13, 2016, now Pat. No. 10,042,975.

(60) Provisional application No. 62/162,502, filed on May 15, 2015, provisional application No. 62/333,941, filed on May 10, 2016.

(51) Int. Cl.
| | |
|---|---|
| *C07K 14/725* | (2006.01) |
| *C12N 15/10* | (2006.01) |
| *G16B 30/00* | (2019.01) |
| *C07K 16/28* | (2006.01) |
| *G01N 33/50* | (2006.01) |
| *C40B 30/04* | (2006.01) |

(52) U.S. Cl.
CPC .......... *G16B 30/00* (2019.02); *C07K 14/7051* (2013.01); *C07K 16/2818* (2013.01); *C07K 16/2827* (2013.01); *G01N 33/5005* (2013.01); *C07K 2317/14* (2013.01); *C07K 2317/21* (2013.01); *C07K 2317/24* (2013.01); *C07K 2317/565* (2013.01); *C07K 2317/76* (2013.01); *C07K 2317/92* (2013.01); *C40B 30/04* (2013.01)

(58) Field of Classification Search
None
See application file for complete search history.

(56) References Cited

U.S. PATENT DOCUMENTS

2010/0303829 A1* 12/2010 Fernandez ........... C07K 14/705
424/160.1

OTHER PUBLICATIONS

Blackman (Science, vol. 248, p. 1335-1341, 1990) (Year: 1990).*

* cited by examiner

*Primary Examiner* — Michael Allen
(74) *Attorney, Agent, or Firm* — Jun He Law Offices P.C.; James J. Zhu; Yi Zhang

(57) ABSTRACT

Provided are methods for identifying T-cell receptors that bind to an antigen in primates. In certain embodiments, the methods comprise: sequencing the cDNA prepared from a combined population of T-cells to obtain a plurality of T-cell receptor alpha chain sequences and a plurality of T-cell receptor beta chain sequences; grouping the obtained alpha chain sequences into alpha chain groups based on their CDR3 sequences; grouping the obtained beta chain sequences into beta chain groups based on their CDR3 sequences; pairing the alpha chain groups with the beta chain groups based on the number of alpha chain or beta chain sequences in each group; pairing one alpha chain sequence and one beta chain sequence in each paired alpha chain group and beta chain group; and testing candidate T-cell receptor comprising the paired alpha chain and beta chain sequences for binding to the antigen.

12 Claims, 12 Drawing Sheets
Specification includes a Sequence Listing.

| SEQ ID NO | Name | Sequence |
|---|---|---|
| 1 | 138-H5-7 | SLQLVQSGAEVKRPGESLKISCKTSGYSFTS---YWISWVRQMPGKGLEWMGAIDP---SD-- |
| 2 | 138-H3C-5 | EVQLAESGGGLVQPGGSLRLSCAASGFIFDD---YAMSWVRQAPGKGLEWVSRVTW---NS- |
| 3 | 138-H3B-5 | EVHLVESGGGLVQPGGSLRLSCAASGFTFSD---SWMSWIRQAPGKGLEWVARIKREADG- |
| 4 | 138-H3C-6 | EVRLVESGGGLVQPGGSLRLSCAASGFNFSD---YYIYWVRQAPGMGLEWVGFVRKPAYG- |
| 5 | 138-H3B-1 | EVQLVESGGALAQPGGSLRLSCAASGFTFTD---YYMDWVRQAPGKGLEWVSRIRNKANS- |
| 6 | 138-H3B-3 | EVRLVESGGGLVQPGGSLRLSCAASGFTFSD---YYMSWVRQAPGKGLEWVGFIRNKVNG- |
| 7 | 138-H3C-4 | EVQLIDSGGGLVQPGGSLRLSCAASGFRLTD---YAIYWVRQAPGKGLEWLGFIRSKAYD- |
| 8 | 138-H3B-4 | EVRLVESGGGLVQPGGSLRLSCAASGFTFSD---YYMSWVRQAPGKGLEWVGFIRNKANG- |
| 9 | 138-H3B-2 | EVHLVESGGDLVHPGGSLRLSCAASGFPFSD---YTIYWVRQAPRKGLEWVGFIRTKAFD- |
| 10 | 138-H3B-10 | EVHLVESGGDLVHPGGSLRLSCAASGFPFSD---YTIYWVRQAPRKGLEWVGFIRTKAFD- |
| 11 | 138-H3A-9 | EVQLVESGGGLVWPGGSLTLSCAASGFIFSD---YGFNWVRQAPGKGLEWISYISP----YS- |
| 12 | 138-H3A-2 | EVQLVETGGGLVQSGGSLRLSCEASGFLFRS---RGMNWVRQAPGKGLEWVSGISF----DG- |
| 13 | 138-H3B-7 | EVQLVESGGGLVQPGGSLRLSCVASGFTFIK---YGINWVRQAPGKGLEWVAFITY---EG- |
| 14 | 138-H3C-8 | EVQLVESGGGLVQPGGSLRLSCAASGFTFTT---YGIHWVRQAPGKGLEWVAFISS---DG- |
| 15 | 138-H3A-4 | EVQLVESGGGLVQPGGSLRLSCAASGFTFSS---YSMYWVRQAPGKGLEWVALISY---DG- |
| 16 | 138-H4-10 | EVQLVESGGGLVQPGGSLRLSCTASGFTFSS---YGMHWVRQAPGKGLEWVAVISY---DG- |
| 17 | 138-H3A-6 | --EQLVESGGGLVQPGASLRLSCAASEFTFSL---YDMHWVRQAPGKGLEWISGINI---G---- |
| 18 | 138-H3C-9 | DVQLVESGGGLVKPGGFLRVSCEGSGFTFSH---HEMHWVRQAPGKGLEWVSVISK--TG- |
| 19 | 138-H3B-8 | EVQLMESGGGLAKPGGSLRLSCAASGFIFSD---HYMDWVRQAPGKGLDWVSRIDN--AG- |
| 20 | 138-H3A-10 | DMQLVETGGGLVQPGGSLRLSCAASGLSFST---YGLNWVRQAPGKGLEWVSGLSY----SP- |
| 21 | 138-H3C-7 | EVQLVESGGGLVQPGGSLRLSCVASGFTFNK---YGMTWVRQAPGKGLEWVSSIND---GG- |
| 22 | 138-H3A-8 | EVQLVESGGGLAKPGGSLRLTCVASGFTFSN---YAMHWVRQAPGKGLDWVSGINS---GG- |
| 23 | 138-H3A-5 | EELLMDLGGGLAQPGGSLRISCAASRFTFNY---YGMNWVRQAPGKGLEWISGING---GG- |
| 24 | 138-H3B-9 | EVQLVETGGGLAKPGGSLRLSCAASGLTFST---YSMHWVRQAPGKGLEWISAINS---GG- |
| 25 | 138-H2-10 | QVTLKESGPALVKPTQTLTLTCTFSGFSLTTSGLGVGWIRQSPGRTLEWLGTIFW--D-- |
| 26 | 138-H2-4 | QITLKESGPALINPTQTLTLTCTFSGFSFSDSGTGVAWIRQPPGKALEWLTSIYW--N--- |
| 27 | 138-H2-2 | QITLKESGPTLVRPTQTLTLTCTFSGFSITTSKTGVGWIRQPPGKALEWLGNIYW--N--- |
| 28 | 138-H2-9 | QVTLKESGPALVKPTQTLTLTCTFSGFSLSTSGMGVGWIRQPPGKALEWLALIYW--D--- |
| 29 | 138-H6-2 | QVRLQESGPGLVKPSQTLSLTCAISGDTVSRYSATWNWVRQSPSRGLEWLGRTYF--RSK |
| 30 | 138-H6-5 | QVQLQESGPGLVKPSQTLSLTCAISGDSVSSNSATWNWIRQSPSRGLEWLGRTYY--RSK |
| 31 | 138-H4-2 | QVQLQESGPGLVRPSETLSLTCAVSGDSVSS-INWWSWIRQSPGKGLDWIGSLSG----SG- |
| 32 | 138-H4-4 | QVQLQESGPAVVKPSETLSLTCVVSGGSISG-GYGWSWIRQAPPKGLEWIGSIYG---LS- |
| 33 | 138-H4-9 | QVQLQESGPGLVKPLETLSLTCGVSGGSISS---NHWSWIRQAPGKGLEWIGLFTY------S- |
| 34 | 138-H4-3 | QVQMQESGPGLVKPSETLSVTCAFSGDSISN---YYWSWFRQSPGKGLEWIGYIYG---SD- |
| 35 | 138-H4-8 | QVQLQESGPGLVKPSETLSLTCTVSGDSISN---YYWTWIRQPPGKGLEWIGYIYG---S--- |
| 36 | 138-H4-1 | QVQLQESGPGLVKPSETLSLTCAVSGGSISG----YYWNWIRQPPGKGLEWIGYIGG---SS- |
| 37 | 138-H4-6 | QVQLQDSGPGLVKPSETLSLTCAVSGGSISG----YYWNWIRQPPGKGLEWIGYIGG---SS- |

FIG. 5A

| SEQ ID NO | Name | Sequence |
|---|---|---|
| 1 | 138-H5-7 | SDTRYSPSFQGQVTISADKSISTAYLQWSSLKASDTATYYCAKDRY--------------G |
| 2 | 138-H3C-5 | YTTSYADSVKGRFTISRENAANSLYLQMNRLNPEDTGLYYCARDGDEHCT-G---------IGC |
| 3 | 138-H3B-5 | GTADYAATVKGRFTISRDDSKNTLYLQMNSLKTEDTAVYYCTTDRGT------------G |
| 4 | 138-H3C-6 | GTSEYAASVKGRFILSRDDSKDVAYLQMGSLKIEDTAVYYCSMAYS---S-------AWD |
| 5 | 138-H3B-1 | YTTEYAASVKGRFTISRDDSKNTLYLQMNSLQTEDTAVYYCARTAA---Y-------SGK |
| 6 | 138-H3B-3 | GTTEYAASVKGRFTISRDDSKSIASLQMNSLKTEDTAVYYCTRGGIAVVV---------SPT |
| 7 | 138-H3C-4 | GTAEYAASVKGRFTFSRDDSKDTAFLQMSSLKTEDSAVYYCTRGNWNY-------------V |
| 8 | 138-H3B-4 | GTAEYAASVKGRFAISRDDSKNTTYLQLSSLKTEDSAVYFCTRGNWNY------------V |
| 9 | 138-H3B-2 | GTADYAASVKGRFTLSRDDSKNTAYLQLSSLKTEDSAVYFCTRANWNY------------V |
| 10 | 138-H3B-10 | GTADYAASVKGRFTISRDDSKNTAYLQLSSLKTEDSAVYFCTRANWNY------------V |
| 11 | 138-H3A-9 | SFIYYSDSVKGRFTISRDSATDSVSLLMDGLRPDDTAVYYCAKSRLSWN----------DGR |
| 12 | 138-H3A-2 | RPIYYADAVPGRFTISRDNSRNTLYLEMQSLEIEDTAVYYCVKQNGDTVG----------TVD |
| 13 | 138-H3B-7 | SKKYYADAVTDRFTISRDNSNNILYLQMNNLKVEDSAVYFCARDRDYFDS------------ |
| 14 | 138-H3C-8 | SKKYYVDSMKDRFTISRDNSKNMVYLQLNNLKMEDTAVYYCVRPKMRIAA--------VLY |
| 15 | 138-H3A-4 | SKKYYADSMKGRFTISRDNSKNMLYLQKNMLKLEDTAVYYCASRSY-----------SYS |
| 16 | 138-H4-10 | SRKYYADSVKDRFTISRDNSKNMLYLQMTTLKLEDTAVYYCAPESV-----------TLS |
| 17 | 138-H3A-6 | DGTYYSDSVTGPSIISRDNAKNSLYLQVNSLRTEDTGVYYCTRTKG------------YTI |
| 18 | 138-H3C-9 | DVTYYADSVKGPFTISRDNAKNSLSLQMNSLTAEDTAVYFCTRVSISILRVD-------IKP |
| 19 | 138-H3B-8 | HSTWYADSAKDRFTMSRDNTKNTLFLQMDSLRGEDTAVYYCAAAY------------DRQ |
| 20 | 138-H3A-10 | GSTYYADSVKGRFTISRDTSKNMLTLQMNSLRIEDTAVYYCAKVGGPTE--I-----TPV |
| 21 | 138-H3C-7 | DSTFYAESVKGRFVISRDNSKNMLSLQMNSLTIADTAVYYCATGS--------------- |
| 22 | 138-H3A-8 | STYYADSVKGRFTISRDNSNNTLSLQMDSLRTEDMAVYYCAKDPE------W-------ITA |
| 23 | 138-H3A-5 | DTTYYADSVPGRFTISRDNSENTLSLQMNSLRVEDTAVYYCAKRG--------------- |
| 24 | 138-H3B-9 | GSIWYIDSVKGRFTISRDNSKNTLSLQMNSLRPEDTAVYYCAKGG--------------- |
| 25 | 138-H2-10 | GDRNYNTSLGNRITISKDTSTNQVVLTLTDVDPLDTGTYYCARGSGPLKWIPKLRNYQKC |
| 26 | 138-H2-4 | DGKYWSPSLENRLSVFKDPSKNQVVLRMTNMDPEDTATYYCAWLQLTRVTISGVVKY-GQ |
| 27 | 138-H2-2 | GDKSYTPSLKRGLTISKDTTKNQVLLTLTNLAPVDTATYYCAPLYVMNVLT----------A |
| 28 | 138-H2-9 | DDKRYSTSLKSPLTISKDTSKNQVVLTMTNMDPVDTAFYYCARGDWGTVGT---------V |
| 29 | 138-H6-2 | WYSDYAQSVENRITIGSDTSRNQFSLEVNSVSPEDTAVYFCTRVQ-------WG-------HLM |
| 30 | 138-H6-5 | WYNDYAQSVQNRITINPDTSKNQFSLQLNSVTPEDMAVYYCARGGAL----MD-----VWG |
| 31 | 138-H4-2 | GTIYLNPSLKSRVNLSIDTSRNHLSFNLTSVTSADTAVYYCARHEIV------------G |
| 32 | 138-H4-4 | GGTFYNPSLKSRITISKDTSKTQVSLKLSPVTVADTAVYYCARQFRYNSGWA------PEN |
| 33 | 138-H4-9 | GSANYNSYLKSRVTLSVDTSKNQFSLKLTSVTAADTAVYYCARVGE--------------- |
| 34 | 138-H4-3 | RTIKYNPSLKSRATLSVDTSKNQFSLKLDSVTAADTAVYYCARDRM--------------- |
| 35 | 138-H4-8 | GSTYYNPSLKSRVTISKDTSKNQYSLKVNSATAADTAAYYCAREGGVAA--D-----LGG |
| 36 | 138-H4-1 | GSTDYNPSLKSRVTISTDTSKNQFSLKLTSVTAADTAIYYCARHSDT----------VGG |
| 37 | 138-H4-6 | GSTDYIPSLKSRVTLSVDTSKNQFSLKLSSVTAADTAVYYCARNGRTA---------ATD |

FIG. 5B

| SEQ ID NO | Name | Sequence |
|---|---|---|
| 1 | 138-H5-7 | TYFYYWGQGVLVTVSS |
| 2 | 138-H3C-5 | YLIDSWGQGVLVTVSS |
| 3 | 138-H3B-5 | TTILYWGQGVLVTVSS |
| 4 | 138-H3C-6 | ISFEFWGQGALVTVSS |
| 5 | 138-H3B-1 | HFSDYWGQGVLVTVSS |
| 6 | 138-H3B-3 | PYFYYWGQGALVTVSS |
| 7 | 138-H3C-4 | DWFDVWGPGVLVTVSS |
| 8 | 138-H3B-4 | NWFDVWGPGVMVTVSS |
| 9 | 138-H3B-2 | NWFDVWGPGVLVTVSS |
| 10 | 138-H3B-10 | NWFDVWGPGVLVTVSS |
| 11 | 138-H3A-9 | YGLDSWGQGAVVTVSS |
| 12 | 138-H3A-2 | GYFDLWGQGALVNVFS |
| 13 | 138-H3B-7 | GYWAYWGQGVLVTVSS |
| 14 | 138-H3C-8 | YGLDSWGQGVVVTVSS |
| 15 | 138-H3A-4 | FGLDSWGQGVVVTVSS |
| 16 | 138-H4-10 | YYFYNWGQGVLVTVSS |
| 17 | 138-H3A-6 | YGLDSWGQGAVVTVSS |
| 18 | 138-H3C-9 | VYFDVWGPGVLVTVSS |
| 19 | 138-H3B-8 | YAIDHWGQGVLVIVSS |
| 20 | 138-H3A-10 | YYFYWGPGVQVIVSS |
| 21 | 138-H3C-7 | -NYDYWGQGVLVSVSS |
| 22 | 138-H3A-8 | YGLDSWGQGAVVTVSS |
| 23 | 138-H3A-5 | LALDVWGRGILVTVSS |
| 24 | 138-H3B-9 | LALDVWGRGVLVTVSS |
| 25 | 138-H2-10 | PAFHLWGPGLSVTVSS |
| 26 | 138-H2-4 | GRFEVWGQGAVVTVSS |
| 27 | 138-H2-2 | GGFYYWGQGILVTVSS |
| 28 | 138-H2-9 | DYFYYWGQGVLVTVSS |
| 29 | 138-H6-2 | RWFDVWGPGILVTVAS |
| 30 | 138-H6-5 | SWFDVWGPGVLVTVSS |
| 31 | 138-H4-2 | NALYFWGQGVLVTVSS |
| 32 | 138-H4-4 | YGLDFWGQGAVVTVSS |
| 33 | 138-H4-9 | ------PWGQGLRVTVSS |
| 34 | 138-H4-3 | WGVYYWGPGVLVTVSS |
| 35 | 138-H4-8 | NWLDVWGPGVRVTVSS |
| 36 | 138-H4-1 | YSLDVWGRGVLVTVSS |
| 37 | 138-H4-6 | YGLDSWGQGVVVTVSS |

FIG. 5C

| SEQ ID NO | Name | Sequence |
|---|---|---|
| 38 | 138-L1-3 | DVVMTQSPLSLPITPGQPASISCRSSQSLVH-SNGNTYLSWYQQKPGQPPRLLIYQVSNR |
| 39 | 138-L1-5 | DVVMTQSPLSLPITPGQPASISCRSSQSLVH-SDGNTYLSWYQQKPGQPPRLLIYKVSNR |
| 40 | 138-L1-4 | DIVMTQTPLSLPVTLGEPASISCRSSQSLVY-SDGKTYLDWYLQKPGQSPQLLMYLVSKR |
| 41 | 138-L1-9 | DIVMTQAPVSLPVIPGESASISCRSSQSLFDSEDGNTYLDWYLQKPGQSPQLLIYEVSNR |
| 42 | 138-L1-6 | DIVTTQTPLSLPVTPGEPASISCRSSQSLLDSEDGKTFLDWYLQKPGQSPQLLIYEVSNR |
| 43 | 138-L1-7=8 | DIVMTQTPLSLPVTPGEPASISCRSSQSLLDSEDGNTYLDWYLQKPGQSPQLLIYEVSNR |
| 44 | 138-L1-1 | DIVMTQTPLSLPVTPGEPASISCRSSQSLLDSEDGNTYLEWYLQKPGQSPQPLLIYEVSNR |
| 45 | 138-L1-10 | DIVMTQTPLSLPVTPGEPASISCRSSQSLLDSEDGNTYLDWYLQKPGQSPQFLLIYEVSNR |
| 46 | 138-L3B-6 | QILLTQSPATLSLSPGERATLSCRASQSVS------SSLSWYQQKPGQAPRLLIWGATRR |
| 47 | 138-L3B-8 | QVILTQSPATLSLSPGDRATLSCRASQSVD------RSLAWYQQQPGQAPRLLIYGVSSR |
| 48 | 138-L3A-10 | QILLTQSPATLSLSPGERATLSCRASQSVS------TNLAWYQQKPGQAPRLLIYGASSR |
| 49 | 138-L3A-6 | QAILTQSPATLSLSPGERATLSCRASQSVA------SSLAWYQQKAGQAPRLLIYGASSR |
| 50 | 138-L3B-7 | QVILTQSPATLSLSPGERATLSCRASQSVS------SSLAWYQQKPGQAPRLLIYGASSR |
| 51 | 138-L3B-10 | QVILTQSPATLSLSPGERATLSCRASQSVS------SSLAWYQQKPGQAPRLLIYGASSR |
| 52 | 138-L3B-3 | QIVLTQSPATLSLSPGERATLSCRASQNVG------DYLAWYHQKPGQAPRLLIHSVSTR |
| 53 | 138-L3B-1 | QVILTQSPATLSLSPGERATLSCRAGQTVS------TFLAWYQQKPGQAPRLLVHSASKR |
| 54 | 138-L3B-2 | QVILTQSPATLSLSPGERATLSCRASQSVS------SYLAWYQQKPGQAPRLLIHSASSR |
| 55 | 138-L3A-1 | EVVMTQSPATLSLSPGETATISCRTSQSIS------AKLAWYQHKPGQAPRVVIYSASKR |
| 56 | 138-L3A-3 | EILMTQSPATLVLSPGLRATLSCRASQNVS------NYLAWYHKPGQAPRLLIYGASNR |
| 57 | 138-L3B-5 | EIVMTQSPATLSLSPGERATLSCRASQSVS------SYLAWYQQKPGQAPRLLIYDASSR |
| 58 | 138-L3B-4 | EIVLTQSPATLSLSPGERATLSCRASQRVG------SNLDWYQQKPGQPPRLLIYYTSNR |
| 59 | 138-L3A-8 | EIVMTQSPATLSLSPGERATLSCRASQSVG------SSLAWYQQKPGQAPRLLIYGASSR |
| 60 | 138-L3A-2 | EIEMTQSPATLSLSPGERATLSCRASQSVS------SNLAWYQQKPGQAPRLLIYYATNR |
| 61 | 138-L3A-4 | EIVMTQSPATLSLSPGERATLSCRASQGVS------SNLAWYQQKPGQAPRLLIYYASNR |
|  |  | :  **:* :*  :  *  *::***:.* :             * ** :: ** |

| SEQ ID NO | Name | Sequence |
|---|---|---|
| 38 | 138-L1-3 | YSGVPDRFSGSGAGTDFTLKISRVEADDVGVYYCGQGAHLP-RTFGQGTKVEIKR |
| 39 | 138-L1-5 | YSGVPDRFSGSGAGTDFTLKISRVEAEDVGVYYCGQGTKVP-LTFGGGTKVEIKR |
| 40 | 138-L1-4 | ASGVPDKFSGSGSGTDFTLKISRVEAEDVGVYYCMQALRSP-LTFGGGTKVEIKR |
| 41 | 138-L1-9 | ASGVPDRFSGSGSDTDFTLKIRRVEAEDAGVYYCMQGVEFP-YSFGQGTKVEFKR |
| 42 | 138-L1-6 | ASGVPDRFSGSGSDTDFTLKISRVEAEDVGVYYCMQSMKFP-FTFGPGTKLDIKR |
| 43 | 138-L1-7=8 | ASGVPDRFSGSGSDTDFTLKISRVEAEDVGVYYCMQGIEFPLYSFGQGTKVEIKR |
| 44 | 138-L1-1 | ASGVPDRFSGSGSDTDFTLKISRVEAEDVGVYYCMQGIEYP-WTFGQGTKVEIKR |
| 45 | 138-L1-10 | ASGVPDRFSGSGPDTDFTLKISRVEAEDVGVYYCMQGIEFP-WTFGQGTKVEIKR |
| 46 | 138-L3B-6 | ATGIPDRFSGSGSGTEFTLTISSLEPEDFAIYYCQRYDNSP-YSFGQGTKVEINR |
| 47 | 138-L3B-8 | ATGIPDRFSGSGSGTEFTLTISSLEPEDFALYYCQKYFT-S-WTFGQGTKVELKR |
| 48 | 138-L3A-10 | ATGIPDRFSGSGSGTDFTLTISSLEPEDFAVYYCQKYSSPP-HSFGQGTKVEIKR |
| 49 | 138-L3A-6 | ATGIPDRFSGSGSGTEFILTISSLEPEDFAVYYCQKYSSSP-FTFGPGTRLDIKR |
| 50 | 138-L3B-7 | ATGIPDRFSGSGSGTEFTLTISSLEPEDFAVYYCQKYSNSP-LTFGGGTKVEIKR |
| 51 | 138-L3B-10 | ATGIPDRFSGSGSGTEFTLTISSLEPEDFAVYYCQKYSSSP--TFGQGTKVEIKR |
| 52 | 138-L3B-3 | ATGIPDKFIGSGSGTQFTLTISRLESEDVGVYHCYQYYN-N-YSFGQGTKVEIKR |
| 53 | 138-L3B-1 | AAGTPDRFSGSGSGTEFTLTISSLEPEDVGIYHCYQYYD-K-WTFGQGTKVEIKR |
| 54 | 138-L3B-2 | ATGIPDRFSGSGSGTEFTLTISSLEPEDVGVYHCYQYYT-G-YSFGQGTKVEIKR |
| 55 | 138-L3A-1 | ATGIPGRFSGRGSETDFTLTISSLEPEDFAVYFCQETPNF---WTFGQGTKVEVKR |
| 56 | 138-L3A-3 | ATGIPDRFSGSGSGTEFTLTISSLEPEDVGVYFCLQSSNWP-LTFGGGTKVEIKR |
| 57 | 138-L3B-5 | ATGIPDRFSGSGSGTEFTLTISSLEPEDVAVYFCQQESNW--WTFGQGTKVEIKR |
| 58 | 138-L3B-4 | ATGIPERFSGSGSGTDFTLTISSLEPEDVGVYYCQQENNWP-LTFGGGTKVEIKR |
| 59 | 138-L3A-8 | ATGIPDRFSGSGSGTDFTLTISSLEPEDVAVYYCLQRSNWP-LTFGGGTKVEIKR |
| 60 | 138-L3A-2 | ATGIPDRFSGSGSGTDFTLTISSLEPEDVGVYYCQQESNWP-LTFGGGTKVEIKR |
| 61 | 138-L3A-4 | ATGIPDRFSGSGSGTDFTLTISSLEPEDVGVYYCQQESNWP-RTFGQGTKVEIKR |
|  |  | :* * :* * * *:* *.* :* :* .:*.* :         :** **::::.:* |

FIG. 6

```
SEQ ID NO   Name            Sequence
   62       H1-2ndPCR-4     QEQLVQSGGGLVQPGGSLRVSCAASGFTFSDYVIYWVRQTPGKGLEWVGLIRRKANGGTA
   63       H1-2ndPCR-12    QVQLVQSGGDWVQPGGSLRLSCAASGFAFNNAWMNWVRQAPGKGLVWVARIKSKGNGETP
   64       H1-2ndPCR-2=3   QVQLVQSGGGLVQPGGSLRLSCAASGFTFSNAWMNWVRQAPGKGLVWVARIKSKANGETA
   65       H1-2ndPCR-9     EVQLVQSGGGLVQPGGSLRLSCAASGFTFSNAWMNWVRQAPGKGLVWVARIKSKANGETT
   66       H1-2ndPCR-11    EVQLVQSGGGLVQPGGSLRVSCGASGFIFSNAWMNWVRQAPGKGLVWVARIKNKPNGETA
   67       H1-2ndPCR-7     QEQLVQSGGGLVQPGGSLRLSCAVSGFTFSNYWMNWVRQAPGKGLDWVGRIKDKVDGGTA
   68       H1-2ndPCR-8     QVQLVQSGGGLVQPGGSLRLSCAASGFTFSNYWMSWVRQAPGKGLDWVGRIKNKADGGAA
   69       H1-2ndPCR-1     QEQLVQSGGGLVQPGGSLRLSCAASGFTFSGYEMHWVRQAPGKGLESVSIIGG-DS-SYT
   70       H1-2ndPCR-6     QVQLVQSGGGLVQPGGSLRLSCAASGFTFSGYEMHWVRQAPGKGLESVSIIGG-DS-SYT
   71       H1-2ndPCR-5     QEQLVQSGGGLVQPGGSLRLSCVTSGFTFSDYEMAWVRQATGKGLEWVSSISQ-PSGTNT
                            : *******  ********:**  .*** *.   : ****: ****    *. *      .

SEQ ID NO   Name            Sequence
   62       H1-2ndPCR-4     QEQLVQSGGGLVQPGGSLRVSCAASGFTFSDYVIYWVRQTPGKGLEWVGLIRRKANGGTA
   63       H1-2ndPCR-12    QVQLVQSGGDWVQPGGSLRLSCAASGFAFNNAWMNWVRQAPGKGLVWVARIKSKGNGETP
   64       H1-2ndPCR-2=3   QVQLVQSGGGLVQPGGSLRLSCAASGFTFSNAWMNWVRQAPGKGLVWVARIKSKANGETA
   65       H1-2ndPCR-9     EVQLVQSGGGLVQPGGSLRLSCAASGFTFSNAWMNWVRQAPGKGLVWVARIKSKANGETT
   66       H1-2ndPCR-11    EVQLVQSGGGLVQPGGSLRVSCGASGFIFSNAWMNWVRQAPGKGLVWVARIKNKPNGETA
   67       H1-2ndPCR-7     QEQLVQSGGGLVQPGGSLRLSCAVSGFTFSNYWMNWVRQAPGKGLDWVGRIKDKVDGGTA
   68       H1-2ndPCR-8     QVQLVQSGGGLVQPGGSLRLSCAASGFTFSNYWMSWVRQAPGKGLDWVGRIKNKADGGAA
   69       H1-2ndPCR-1     QEQLVQSGGGLVQPGGSLRLSCAASGFTFSGYEMHWVRQAPGKGLESVSIIGG-DS-SYT
   70       H1-2ndPCR-6     QVQLVQSGGGLVQPGGSLRLSCAASGFTFSGYEMHWVRQAPGKGLESVSIIGG-DS-SYT
   71       H1-2ndPCR-5     QEQLVQSGGGLVQPGGSLRLSCVTSGFTFSDYEMAWVRQATGKGLEWVSSISQ-PSGTNT
                            : *******  ********:**  .*** *.   : ****: ****    *. *      .

SEQ ID NO   Name            Sequence
   62       H1-2ndPCR-4     VSS
   63       H1-2ndPCR-12    VSS
   64       H1-2ndPCR-2=3   VSS
   65       H1-2ndPCR-9     VSS
   66       H1-2ndPCR-11    VSS
   67       H1-2ndPCR-7     VSS
   68       H1-2ndPCR-8     VSS
   69       H1-2ndPCR-1     VSS
   70       H1-2ndPCR-6     VSS
   71       H1-2ndPCR-5     VSS
                            ***
```

FIG. 7

| SEQ ID NO | Name | Sequence |
|---|---|---|
| 72 | 138-L2-2ndPCR-5 | DVVMTQSPLSLPVTPGEPASISCRSSQSLLDSEDGNTYLDWYLQKPGQSPQPLIYEVSNR |
| 73 | 138-L2-2ndPCR-4 | DVAMTQSPLSLPVTPGEPASISCRSSQSLLDSEDGNTYLDWYLQKPGQSPQLLIYEVSNR |
| 74 | 138-L2-2ndPCR-8 | DVVMTQSPLSLPVTPGEPASISCRSSQSLLDSEDGNTYLDWYLQKPGQSPQLLIYEVSNR |
|  |  | .**************************************** ***** |

| SEQ ID NO | Name | Sequence |
|---|---|---|
| 72 | 138-L2-2ndPCR-5 | ASGVPDRFSGSGSDTDFTLKISRVEAEDVGVYYCMQGIEFPYSFGQGTKVEIKR |
| 73 | 138-L2-2ndPCR-4 | ASGVPDRFSGSGSDTDFTLKISRVEAEDVGVYYCMQGIEFPYSFGQGTKVEIKR |
| 74 | 138-L2-2ndPCR-8 | ASGVPDRFSGSGSDTDFTLKISRVEAEDVGVYYCMQGIEFPYSFGQGTKVEIKR |
|  |  | ****************************************************** |

FIG. 8

METHOD FOR IDENTIFYING ANTIGEN-SPECIFIC T CELL RECEPTORS IN PRIMATE

CROSS-REFERENCE TO RELATED APPLICATIONS

This application is a divisional application of U.S. application Ser. No. 15/208,850, filed Jul. 13, 2016, which claims priority to U.S. provisional patent application Nos. 62/162,502, filed May 15, 2015, and 62/333,941, filed May 10, 2016, the disclosure of which is incorporated herein by reference.

FIELD OF THE INVENTION

The present invention generally relates to methods of generating antibodies and T cell receptors.

BACKGROUND OF THE INVENTION

Antibodies have emerged as effective tools in the treatment of variety of conditions including cancer, inflammation, and other diseases. However, non-human antibodies have been demonstrated to induce human immune responses, which results in neutralization of administered antibody and limits the application of such antibodies in treatment of human diseases. The art has attempted to overcome this problem by humanizing monoclonal antibodies derived from non-human animals, e.g., mice and rabbit. For example, a humanized antibody can be accomplished by grafting the appropriate complementary determining region (CDR) coding segments into a human antibody framework. However, antibodies humanized by CDR graft method often have problem of loss of affinity to their specific targets.

T cell receptor (TCR) is a molecule found on the surface of T cells that is responsible for recognizing antigens bound to major histocompatibility complex (MHC) molecules. The binding between TCR and antigen is of relatively low affinity and is degenerate, i.e., many TCRs recognize the same antigen and many antigens are recognized by the same TCR. The affinity of TCR or a specific antigen makes them valuable for therapeutic uses, e.g., cancer treatment by using adoptive immunotherapy. In order to extend the capacity to use adoptive immunotherapy, it is a goal to transfer enriched, peptide-specific effector T cells that have been selected for their ligand specificities to effectively attack tumor cells which avoiding serious attack of normal tissues. For this purpose, the TCRs of such ligand-specific T cells can be cloned and expressed as TCR-transgenes in activated T cells, such that the transgenic T cells obtain defined specificities and do not have the capacity to attack normal host tissues.

Therefore, there is a continuing need for new method to develop antibodies and T cell receptors.

BRIEF SUMMARY OF THE INVENTION

In one aspect, the present disclosure relates to methods of identifying a primate antibody that binds to an antigen. In some embodiments, the method may comprise the steps of: a) obtaining a population of antibody-producing B cells from a primate that has been immunized by the antigen; b) obtaining from the population of antibody-producing B cells (i) a plurality of antibody heavy chain sequences and (ii) a plurality of antibody light chain sequences; c) grouping said obtained plurality of antibody heavy chain sequences into at least one heavy chain group, wherein said antibody heavy chain sequences in the heavy chain group are related in lineage; d) grouping said obtained plurality of antibody light chain sequences into at least one light chain group, wherein said antibody light chain sequences in the light chain group are related in lineage; e) selecting said heavy chain group and said light chain group; f) pairing a heavy chain sequence from said heavy chain group and a light chain sequence from said light chain group; and g) testing a candidate antibody comprising the heavy and light chain sequences for binding to the antigen.

In certain embodiments, the CDR3 regions of said antibody heavy chain sequences in the heavy chain group contain up to five amino acid differences relative to one another, and the CDR3 regions of said antibody light chain sequences in the light chain group contain up to five amino acid differences relative to one another.

In certain embodiments, the antigen is a human antigen.

In certain embodiments, the antibody heavy chain sequences are antibody heavy chain variable domain sequences and the antibody light chain sequences are antibody light chain variable domain sequences.

In certain embodiments, the primate is an old world monkey, an orangutan, a gorilla or a chimpanzee. In certain embodiments, the primate is a crab-eating macaque, a rhesus macaque or a pigtail macaque.

In certain embodiments, the CDR3 region of said antibody heavy chain sequences in the heavy chain group contains 0, 1 or 2 amino acid differences relative to one another; and wherein the CDR3 region of the antibody light chain sequences in the light chain group contains 0, 1 or 2 amino acid differences relative to one another.

In certain embodiments, step b) is done by sequencing cDNAs encoding the heavy and light chain sequences from single B cells, or cultures of the same.

In certain embodiments, step b) is done by sequencing cDNAs encoding the heavy and light chain sequences made from a plurality of B cells.

In certain embodiments, the population of antibody-producing B cells are enriched by binding to the antigen.

In certain embodiments, the heavy chain group and the light chain group both contain at least 2, at least 5, at least 10, at least 20 members.

In certain embodiments, the step g) comprises testing the candidate antibody in a blocking assay, a neutralization assay, an agonist assay or an antagonist assay.

In certain embodiments, the step g) comprises testing the candidate antibody in an ELISA.

In certain embodiments, the step b) comprises obtaining at least 100 different antibody heavy chain sequences and at least 100 different antibody light chain sequences.

In certain embodiments, the antibody-producing B cells are obtained from bone marrow, spleen, lymph node or peripheral blood.

In certain embodiments, the method further comprises: h) aligning the heavy chain sequence with a human heavy chain sequence, wherein the human heavy chain sequence is most homologous to the heavy chain sequence; i) aligning the light chain sequence with a human light chain sequence, wherein the human light chain sequence is most homologous to the light chain sequence; and j) substituting at least one amino acid residues in the heavy chain or light chain sequence with the corresponding amino acid of the human heavy chain or human light chain sequence, thereby producing a humanized antibody.

In another aspect, the present disclosure provides a method for identifying a T-cell receptor (TCR) that binds to an antigen, comprising steps of: a) obtaining a population of T cells of a primate that has been immunized by the antigen; b) obtaining from the population of T cells (i) a plurality of TCR α-chain sequences and (ii) a plurality of TCR β-chain sequences; c) grouping said obtained plurality of TCR α-chain sequences into at least one TCR α-chain group, wherein the TCR α-chain sequences in the TCR α-chain group are related in lineage; d) grouping said obtained plurality of TCR β-chain sequences into at least one TCR β-chain group, wherein the TCR β-chain sequences in the TCR β-chain group are related in lineage; e) selecting the TCR α-chain group and the TCR β-chain group; f) pairing a TCR α-chain sequence from the TCR α-chain group and a TCR β-chain sequence from the TCR β-chain group; and g) testing a candidate TCR comprising the TCR α-chain sequence and the TCR β-chain sequence for binding to the antigen.

In certain embodiments, the CDR3 regions of said TCR α-chain sequences in the TCR α-chain group contain up to five amino acid differences relative to one another, and the CDR3 regions of said TCR β-chain sequences in the TCR β-chain group contain up to five amino acid differences relative to one another.

In certain embodiments, the antigen is a human antigen.

In certain embodiments, the TCR α-chain sequences are TCR α-chain variable domain sequences and the TCR β-chain sequences are TCR β-chain variable domain sequences.

In certain embodiments, the primate is an old world monkey, an orangutan, a gorilla or a chimpanzee. In certain embodiments, the primate is a crab-eating macaque, a rhesus macaque or a pigtail macaque.

In certain embodiments, the CDR3 regions of the TCR α-chain sequences in the TCR α-chain group contain 0, 1 or 2 amino acid differences relative to one another; and wherein the CDR3 regions of the TCR β-chain sequences in the TCR β-chain group contain 0, 1 or 2 amino acid differences relative to one another.

In certain embodiments, step b) is done by sequencing cDNAs encoding the TCR α-chain and TCR β-chain sequences from single cells, or cultures of the same.

In certain embodiments, step b) is done by sequencing cDNAs encoding the TCR α-chain and TCR β-chain sequences made from a plurality of T cells.

In certain embodiments, the T cells are enriched by binding to the antigen.

In certain embodiments, the TCR α-chain group and the TCR β-chain group both contain at least 2, at least 5, or at least 10 members.

In certain embodiments, the step g) comprises testing the candidate TCR in a blocking assay, a neutralization assay, an agonist assay, or an antagonist assay.

In certain embodiments, the step g) comprises testing the candidate TCR in an ELISA.

In certain embodiments, step b) comprises obtaining at least 100 different TCR α-chain variable domain sequences and at least 100 different TCR β-chain variable domain sequences.

In certain embodiments, the T cells are obtained from bone thymus, lymph node or peripheral blood.

In certain embodiments, the method further comprises: h) aligning TCR α-chain sequence with a human TCR α-chain sequence, wherein said human TCR α-chain sequence is most homologous to said TCR α-chain sequence; i) aligning the TCR β-chain sequence with a human TCR β-chain sequence, wherein said human TCR n-chain sequence is most homologous to said TCR β-chain sequence; and j) substituting at least one amino acid residues in the human TCR α-chain sequence or human TCR β-chain sequence, thereby producing a humanized TCR.

BRIEF DESCRIPTION OF THE FIGURES

FIG. 5A shows the alignment of part of the heavy chain variable region sequences of the antibodies generated in a monkey immunized with PD-L1.

FIG. 5B shows the alignment of the heavy chain variable region sequences continued from FIG. 5A.

FIG. 5C shows the alignment of the heavy chain variable region sequences continued from FIG. 5B.

FIG. 6 shows the alignment of the light chain variable region sequences of the antibodies generated in a monkey immunized with PD-L1.

FIG. 7 shows the alignment of the heavy chain variable region sequences of the antibodies generated in in a monkey immunized with PD-L1 after a second round PCR.

FIG. 8 shows the alignment of the light chain variable region sequences of the antibodies generated in in a monkey immunized with PD-L1 after a second round PCR.

DETAILED DESCRIPTION OF THE INVENTION

Figure 1:
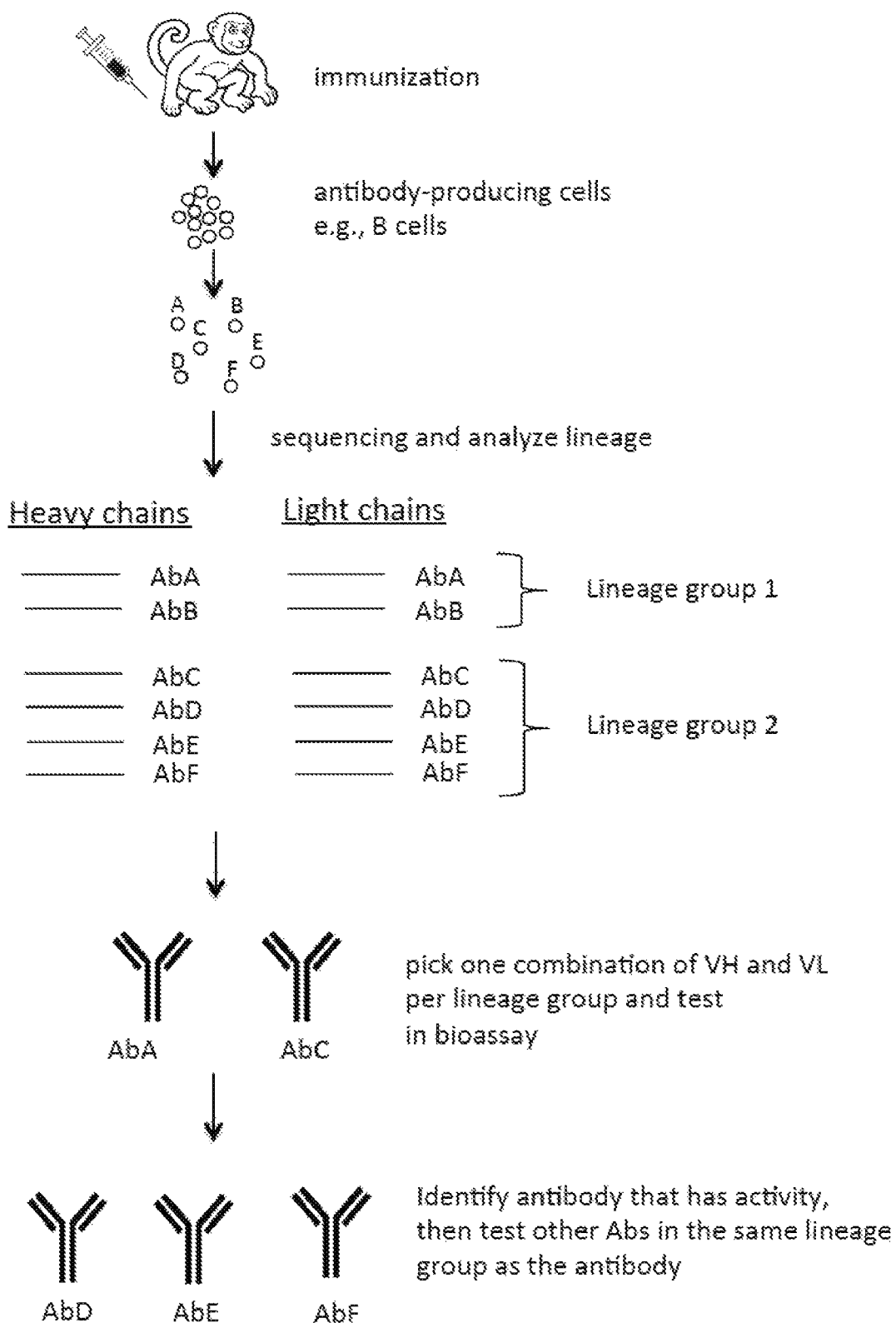
FIG. 1 illustrates an embodiment of identifying a primate antibody that specifically binds to an antigen.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

It must be noted that as used herein and in the appended claims, the singular forms "a," "an," and "the" include the plural reference unless the context clearly dictates otherwise. Thus, for example, a reference to a "cell" is a reference to one or more cells, and includes equivalents thereof known to those skilled in the art and so forth.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without there specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

Definitions

The meaning of certain terms and phrases employed in the specification, examples, and appended claims are provided. The definitions are not meant to be limiting in nature and serve to provide a clearer understanding of certain aspects of the present invention.

The terms "antibody" and "immunoglobulin" are used interchangeably herein. These terms are well understood by those in the art, and refer to a protein consisting of one or more polypeptides that specifically binds an antigen. One form of antibody constitutes the typical structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized human immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the N-terminus and a kappa or lambda constant region at the C-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme that generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed e term are Fab', Fv, F(ab')2, and or other antibody fragments that retain specific binding to antigen, and monoclonal antibodies.

Antibodies may exist in a variety of other forms including, for example, Fv, Fab, and (Fab')2, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed., 1984, and Hunkapiller and Hood, Nature, 323, 15-16, 1986).

An immunoglobulin light or heavy chain variable region consists of a framework region (FR) interrupted by three hypervariable regions, also called "complementarity determining regions" or "CDRs". The extent of the framework region and CDRs have been precisely defined (see, E. Kabat et al., "Sequences of Proteins of Immunological Interest," U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

The term "chimeric antibodies" refers to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody, although other mammalian species may be used.

The term "humanized antibody" or "humanized immunoglobulin" refers to a non-human (e.g., mouse, rabbit or primate) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. As used herein, the primate immunoglobulin providing the CDRs is called the "parent" or "acceptor" and the human antibody providing the framework changes is called the "donor". Constant regions need not be present, but if they are, they are usually substantially identical to human antibody constant regions, i.e., at least about 85-90%, preferably about 95% or more identical. Hence, in some embodiments, a full length humanized primate heavy or light chain immunoglobulin contains a human constant region, primate CDRs, and human framework. In many embodiments, a "humanized antibody" is an antibody comprising a humanized variable light chain and/or a humanized variable heavy chain. For example, a humanized antibody would not encompass a typical chimeric antibody as defined above, e.g., because the entire variable region of a chimeric antibody is non-human. A modified antibody that has been "humanized" by the process of "humanization" binds to the same antigen as the parent antibody that provides the CDRs and is usually less immunogenic in humans, as compared to the parent antibody.

The term "natural" antibody refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from an animal immunized with an antigen are natural antibodies.

The term "non-naturally paired", with respect to $V_H$ and $V_L$ chains of an engineered antibody, refers to a $V_H$ and $V_L$ pair that is not found in a natural antibody. Thus, a non-naturally paired antibody is a combination of $V_H$ and $V_L$ chain of two different natural antibodies. The $V_H$ and $V_L$ chains of a non-naturally paired antibody are not mutated relative to the $V_H$ and $V_L$ chains of the two different antibodies which provide the and $V_L$ chains. For example, the "non-naturally paired" IgH and IgL chains of the engineered antibody may contain the IgH variable chain from a first antibody producing cell obtained from an animal and the IgL variable chain of second antibody producing cell obtained from the same animal, where the amino acid sequence of the antibody produced by the first cell is different from the amino acid sequence of the antibody produced by the second cell. In this example, the IgH and IgL chains may be from the same lineage group. An antibody containing "non-naturally paired" IgH and IgL chains may or not be made by phage display. As such, antibodies may or may not contain viral (e.g., bacteriophage M13)-derived sequences.

The term "lineage-related antibodies" and "antibodies that related by lineage" as well as grammatically-equivalent variants thereof, are antibodies that are produced by cells that share a common B cell ancestor. Related antibodies produced by related antibody producing cells bind to the same epitope of an antigen and are typically very similar in sequence, particularly in their H3 and L3 CDRs. Both the H3 and L3 CDRs of lineage-related antibodies have a near identical sequence (i.e., differ by up to 5, i.e., 0, 1, 2, 3, 4 or 5 residues result from substitution, insertion or deletion) (see U.S. Pat. No. 7,462,697 to Couto). In certain cases, the B cell ancestor contains a genome having a rearranged light chain VJC region and a rearranged heavy chain VDJC region, and produces an antibody that has not yet undergone affinity maturation. "Naïve" or "virgin" B cells present in spleen tissue, are exemplary B cell common ancestors. Related antibodies are related via a common antibody ancestor, e.g., the antibody produced in the naïve B cell ancestor. The term "related antibodies" is not intended to describe a group of antibodies that are not produced by cells that arise from the same ancestor B-cell. A "lineage group" contains a group of antibodies that are related to one another by lineage.

The term "expression" refers to the process by which a polypeptide is produced based on the sequence of a gene. The process includes both transcription and translation.

The term "introduced" in the context of inserting a nucleic acid sequence into a cell, means "transfection", or "transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "nucleic acid" encompasses DNA, RNA, single stranded or double stranded and chemical modification thereof. The terms "nucleic acid" and "polynucleotide" are used interchangeably herein.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The term "plurality" refers to more than 1, for example more than 2, more than about 5, more than about 10, more than about 20, more than about 50, more than about 100, more than about 200, more than about 500, more than about 1000, more than about 2000, more than about 5000, more than about 10,000, more than about 20,000, more than about 50,000, more than about 100,000, more than about 500,000, more than about 1,000,000. A "population" contains a plurality of items.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones.

The terms "treating" or "treatment" of a condition or disease refer to providing a clinical benefit to a subject, and include: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by its self. Antigens are usually proteins and polysaccharides, less frequently also lipids. Suitable antigens include without limitation parts of bacteria (coats, capsules, cell walls, flagella, fimbrai, and toxins), viruses, and other microorganisms. As used herein, antigens also include immunogens and haptens.

The term "T cell receptor" (TCR) refers the molecule found on the surface of T lymphocyte (T cells) for recognizing antigens bound to major histocompatibility (MHC) molecules. Typically, the TCR is a disulfide-linked membrane-anchored heterodimer normally consisting of the highly variable alpha and beta chain, which forms a complex with CD3 molecules. A minority (~5%) of T cells express an alternate receptor, formed by variable gamma and delta chains. The variable domain of the TCR alpha-chain and beta-chain each have three hypervariable or complementary determining regions (CDRs), whereas the variable region of the beta-chain has an additional area of hypervariability (HV4) that does not normally contact antigen. CDR3 is the main CDR responsible for recognizing processed antigen, although CDR1 of the alpha chain has also been shown to interact with the N-terminal part of the antigenic peptide, whereas CDR1 of the beta-chain interacts with the C-terminal part of the peptide. CDR2 is thought to recognize the MHC. CDR4 of the beta-chain is not thought to participate in antigen recognition but has been shown to interact with superantigens. The constant domain of the TCR consists of short connecting sequences in which a cysteine residue forms disulfide bonds, which forms a link between the two chains. The binding between TCR and antigens is of relative low affinity and is degenerate: that is, many TCR recognize the same antigen and many antigens are recognized by the same TCR.

As used herein, a "primate" refers to a mammal of the order Primates, including human beings, apes, and monkeys. Examples of primates include, without limitation, prosimians (e.g., lemurs, lorises, pottos, angwantibos, tarsiers), new world monkeys (e.g., marmosets, tamarins, capuchins, squirrel monkeys, owl monkeys, titis, sakis uakaris, howler monkeys, spider monkeys, and woolly monkeys), old world monkeys (e.g., Allen's swamp monkeys, talapoins, patas monkeys, green monkeys, privets, bale mountains vervet, tantalus monkeys, vervet monkeys, malbroucks, Kryas monkeys, Diana monkeys, roloway monkeys, greate spot-nosed monkeys, blue monkeys, silver monkeys, golden monkeys, skyes' monkeys, mona monkeys, Campbell's mona monkeys, Lowe's mona monkeys, crested mona monkeys, wolf's mona monkeys, Dent's mona monkeys, lesser spot-nosed monkeys, white-throated guenons, Sclater's guenons moustached guenons, red-tailed monkeys, L'Hoest's monkeys, Preuss's monkeys, Sun-tailed monkeys, Hamlyn's monkeys, Lesulas, De Brazza's monkeys, Barbary macaques, lion-tailed macaques, southern pig-tailed macaques, northern pig-tailed macaques, Pagai island macaques, Siberut macaques, moor macaques, booted macaques, Tonkean macaques, Heck's macaques, Gorontalo macaques, Celebes crested macaques, crab-eating macaques, stump-tailed macaques, rhesus macaques, Formosan rock macaques, Japanese macaques, toque macaques, bonnet macaques, assam macaques, Tibetan macaques, Arunachal macaques, white-cheeked macaques, grey-cheeked mangabeys, black crested mangabeys, opdenbosh's mangabeys, Uganda mangabeys, Johnston's mangabeys, Osman Hill's mangabeys, kipunjis, baboons, geladas, sooty mangabeys, collared mangabeys, agile mangabeys, golden-bellied mangabeys, Tana River mangabeys, Sanje mangabeys, mandrills, black colobus, Angola colobus, king colobus, ursine colobus, mantled guerezas, Western red colobus, Pennants' colobus, Niger Delta red colobus, Preuss's red colobus, Zanzibar red colobus, Central African red colobus, Ugandan red colobus, Udzungwa red colobus, Bouvier's red colobus, gray langurs, lutungs, surili, douc langurs, snub-nosed monkeys, long-nosed monkeys, pig-tailed langurs, gibbons, orangutans, gorillas, chimpanzees.

Methods of Identifying a Primate Antibody that Binds to an Antigen

In an aspect, the present invention relates to a method of identifying a primate antibody that binds to an antigen. In certain embodiments, the method may comprise the steps of: a) obtaining a plurality of antibody heavy chain sequences and a plurality of antibody light chain sequences from a population of antibody-producing B cells of a primate that has been immunized by the antigen; b) grouping said obtained plurality of antibody heavy chain sequences into a plurality of heavy chain groups and, independently, grouping said obtained plurality of antibody light chain sequences into a plurality of light chain groups, wherein: antibody heavy chain sequences that comprise CDR3 regions that are of the same length and contain up to five amino acid substitutions relative to one another are grouped together; and antibody light chain sequences that comprise CDR3 regions that are of the same length and contain up to five amino acid substitutions relative to one another are grouped together; c) selecting a heavy chain group and a light chain group from the groups grouped in step b); d) pairing a heavy chain sequence and a light chain sequence from the groups selected in step c); and e) testing an antibody comprising the heavy and light chain sequences paired in d) for binding to the antigen.

One embodiment of the subject method is illustrated in FIG. 1. With reference to FIG. 1, the embodiment of the method may involve immunizing a non-human primate animal with a selected antigen. In FIG. 1, six different antibody producing cells A-F that produce antibodies that bind to a target antigen are enriched from a larger population of antibody producing cells. However, in many embodiments, there may be several hundred, several thousand or several million enriched cells. Each of these cells produces a natural antibody that contains a naturally paired IgH and IgL chain. The amino acid sequences of the heavy and light chains of the antibodies produced by the enriched cells are obtained by sequencing the nucleic acids encoding the IgH and IgL chains of the antibodies (in certain cases, only the nucleic acids encoding the variable region of the IgH and IgL chains of the antibodies are sequenced), and the sequences are analyzed and put into lineage groups which, as discussed above, are groups of antibodies that are produced by cells that share a common B cell ancestor. Such antibodies generally have very similar sequences, and have H3 CDRs of identical length and near identical sequence as well as L3 CDRs of identical length and a near identical sequence. In the embodiment shown in FIG. 1, the six antibody producing cells produce antibodies (AbA to AbF) that are in two lineage groups (i.e., lineage groups 1 and 2, where AbA and AbB are in lineage group 1 and AbC, AbE and AbF are in lineage group 2). After the antibodies have been placed into lineage groups, a single antibody (or, in certain cases, multiple antibodies from each lineage group) from at least one of the lineage group, e.g., AbA from lineage group 1 and AbC from lineage group 2, is selected for testing in a bioassay, where a bioassay identifies an antibody with a biological activity (e.g., a blocking or neutralizing activity). Once an antibody having a biological activity has been identified, e.g., AbC, other antibodies from the same lineage group as the identified antibody are tested to identify a second antibody that has the same biological activity as the first antibody. In the example shown in FIG. 1, antibodies D, E and F, which belong to the same lineage group as antibody C, are tested.

Many non-human primate animals, including without limitation, gorillas, chimpanzees, orangutans, gibbons, crab-eating macaques, rhesus macaques, pig-tailed macaques, may be used as a source of antibody-producing cells. In certain embodiments, the non-human primate animals used to provide antibody-producing cells are rhesus macaques, crab-eating macaques and pigtail macaques. Procedures for immunizing animals are well known in the art, and are described in Harlow et al., ("Antibodies: A Laboratory Manual", First Edition (1988) Cold Spring Harbor, N.Y.).

Suitable antigens include extracellularly-exposed fragments of Her2, GD2, PD-1 (programmed cell death 1), PD-L1 (programmed death-ligand 1), EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL—related ligand), CA125 (carcinoma antigen 125), CEA (carcinoembrionic antigen), CD2 (I-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine A11), HER2/neu, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFβR (Beta platelet-derived growth factor receptor), PMSA, renal carcinoma antigen G250, RSV, E-Selectin, TGFbeta1, TGFbeta2, TNFalpha, TRAIL-R1, VAP-1 (vascular adhesion protein 1) or TNFα, or the like. In many embodiments, a peptide having the amino acid sequence corresponding to a portion of an extracellular domain of one of the above-listed proteins is employed as an antigen.

In certain embodiments, an affinity purification method is utilized to isolate antibody producing cells that produce antibodies that bind to an antigen. The antigen with which the animal was immunized may be immobilized on a solid phase and used to selectively retain antibody producing cells that express an antibody on their surface that binds to the antigen, while other cells are washed away. The retained cells may then be eluted by a variety of methods, such as by using an excess of the antigen, chaotropic agents, changing the pH, salt concentration, etc. Any of the well-known methods for immobilizing or coupling antigen to a solid phase may be used. For example, when the antigen is a cancer cell, appropriately treated microtiter plate that will bind to cells may be used, such as microtiter plates for cell culture. In the instances where the antigen is a protein, the protein may be covalently attached to a solid phase, for example, SEPHARSE crosslinked agarose beads, by well-known techniques, etc. Alternatively, a labeled antigen may be used to specifically label cells that express an antibody that binds to the antigen and the labeled cells may then be isolated by cell sorting (e.g., by FACS). In certain cases, methods for antibody purification may be adapted to isolate antibody producing cells. Such methods are well known and are described in, for example, J Immunol Methods. 2003 November; 282(1-2):45-52; J Chromatogr A. 2007 Aug. 10; 1160(1-2):44-55; J Biochem Biophys Methods. 2002 May 31; 51 (3):217-31. Cells may also be isolated using magnetic beads or by any other affinity solid phase capture method, protocols for which are known. In some embodiments, antigen-specific antibody producing cells may be obtained from blood by flow cytometry using the methods described in Wrammert (Nature 2008 453: 667-672), Scheid (Nature 2009 458: 636-640), Tiller (J. Immunol. Methods 2008 329 112-124) or Scheid (Proc. Natl. Acad. Sci. 2008 105: 9727-9732), for example, which are incorporated by reference for disclosure of those methods. Exemplary antibody-producing cell enrichment methods include performing flow cytometry (FACS) of cell populations obtained from a spleen, bone marrow, lymph node or other lymph organs, e.g., through incubating the cells with labeled IgG specific to the non-human primate animal and sorting the labeled cells using a FACSVantage SE cell sorter (Becton-Dickinson, San Jose, Calif.). In some embodiments, single or nearly single antibody-producing cells are deposited in microtiter plates. If the FACS system is employed, sorted cells may be deposited after enrichment directly into a microtiter plate.

Enrichment may decrease the size of the cell population by at least 50%, e.g., at least 60%, at least 70%, at least 80%, at least 90%, at least 95% or at least 99% and in certain cases, the plurality of enriched antibody producing cells may be substantially pure, i.e., substantially free of other cells that do not produce an antibody that binds to the antigen, where the term "substantially pure" refers to an isolated population of antibody producing cells, in which cells that express antibodies that specifically bind to the antigen make up at least 5%, 10%, 20%, 30%, at least 40%, at least 50%, at least 60%, at least 70% or more of the total population of cells. The enriched population of antibody producing cells may be employed as a mixture of cells, or alternatively, they may be used as single cells, e.g., by dilution and deposition into individual wells of a microtiter plate.

The enriched population of antibody producing cells may comprise at least 5, at least 10, at least 30, at least 60, at least 100, at least 300, at least 500, at least 1000, at least 5,000, at least 10,000 or at least 100,000, or more antibody producing cells.

Antibody-producing cells may be derived from the blood, lymph nodes or bone marrow, as well as from other tissues. Antibody-producing cells may also be prepared from blood collected with an anticoagulant such as heparin or EDTA. The antibody-producing cells may be further separated from erythrocytes and polymorphs using standard procedures such as centrifugation with Ficoll-Hypaque (Pharmacia, Uppsula, Sweden). Antibody-producing cells may also be prepared from solid tissues such as lymph nodes by dissociation with enzymes such as collagenase and trypsin in the presence of EDTA. In preferred embodiments, antibody-producing cells are derived from blood, e.g., peripheral blood mononuclear cell (PBMC).

The isolated antibody-producing cells may be optionally cultured (i.e., grown in media that supports at least one, at least 5 or at least 10 or more cell divisions of the cell) by methods known to one of skill in the art after they have been deposited (see e.g. WO 01/55216).

In certain embodiments, the antibodies produced by the enriched cells are not well characterized. As such, although the antibody-producing cells are isolated based on the production of antibodies that specifically bind to the antigen, the epitope(s) to which these antibodies bind is unknown, and it is not known if the antibodies have any biological activity (e.g., a neutralizing or blocking activity). Additionally, the nucleic acid sequence or the amino acid sequence of the variable regions of IgH and IgL chains of these antibodies are not known.

Sequences encoding heavy and light chains may be amplified from the cDNA using techniques well known in the art, such as Polymerase Chain Reaction (PCR). See Mullis, U.S. Pat. No. 4,683,195; Mullis et al., U.S. Pat. No. 4,683,195; Polymerase Chain Reaction: Current Communication in Molecular Biology, Cold Springs Harbor Press, Cold. Spring Harbor, N.Y., 1989. Briefly, cDNA segments encoding the variable domain of the antibody are exponentially amplified by performing sequential reactions with a DNA polymerase. The reaction is primed by a 5' primer and a 3' DNA primer. In some embodiments, the 3' antisense primer corresponding to a DNA sequence in the constant (or joining) region of the immunoglobulin chain and the 5' primer (or panel of related primers) corresponding to a DNA sequence in the variable region of the immunoglobulin chain. This combination of oligonucleotide primers has been used in the PCR amplification of murine immunoglobulin cDNAs of unknown sequence (see Sastry et al., Proc Natl. Acad, Sci. 86:5728-5732, 1989 and Orlandi et al., Proc. Natl. Acad. Sci. 86:3833-3837, 1989). Alternatively, an "anchored polymerase chain reaction" may be performed (see Loh et al., Science 243:217-220, 1989). In this procedure, the first strand cDNA is primed with a 3' DNA primer as above, and a poly(dG tail) is then added to the 3' end of the strand with terminal deoxynucleotidyl transferase. The product is then amplified by PCR using the specific 3' DNA primer and another oligonucleotide consisting of a poly(dC) tail attached to a sequence with convenient restriction sites. In many embodiments, however, the entire polynucleotide encoding a heavy or light chain is amplified using primers spanning the start codons and stop codons of both of the immunoglobulin cDNAs, however, depending on the amplification products desired, suitable primers may be used. Suitable restriction sites and other tails may be engineered into the amplification oligonucleotides to facilitate cloning and further processing of the amplification products. Amplification procedures using nested primers may also be used, where such nested primers are well known to one of skill in the art. Exemplary methods for amplifying antibody-encoding nucleic acid are also described in Wrammert (Nature 2008 453: 667-672) and Scheid (Nature 2009 458: 636-640), for example. In this embodiment, the cells may be kept separate from one another (in which case the initial amplification product amplified from a single cell may contain a single species that can be sequenced).

In certain embodiments, at least 1,000 heavy chain sequences and at least 1,000 light chain sequences are obtained.

Once the amino acid sequence of heavy and light chains of the antibodies has been obtained, antibodies can be grouped on the basis of sequence similarity to provide a plurality of groups of antibodies that are related by lineage. Methods for performing clonal analysis of antibody sequences are well known and are described in a number of publications including Magori-Cohen (Bioinformatics 2006 22: e332-40), Manske (Clin. Immunol. 2006 120:106-20), Kleinstein (J. Immunol. 2003 171: 4639-49), Clement (Mol. Ecol. 2000 9: 1657-1659), Mehr (J. Immunol. 2004 172 4790-6), Wrammert (Nature 2008 453: 667-672), Scheid (Nature 2009 458: 636-640), which are incorporated by reference herein for disclosure of those methods. The antibodies placed into lineage groups should all be from a single non-human primate animal.

In some embodiments, the amino acid positions of an antibody are numbered using a suitable numbering system, such as that provided by Chothia (J Mol Biol 1998; 278: 457-79) or Kabat (1991, Sequences of Proteins of Immunological Interest, DHHS, Washington, D.C.). CDR and/or framework residues may be identified using these methods. The numbered sequences may be aligned by eye, or by employing an alignment program such as one of the CLUSTAL suite of programs (Thompson et al Nucleic Acids Research, 22:4673-4680). The variable regions of antibodies within a related group of antibodies have amino acid sequences that are very similar. For example, the $V_H$ or $V_L$ domains of antibodies within a related group of antibodies may have amino acid sequences that are at least about 80% identical (e.g., at least 85% identical, at least 90% identical, at least 95% or at least 98% or at least 99% identical), ignoring any gaps or insertions made to facilitate alignment of the sequences. Antibodies within a related group of antibodies have a domains that are similar to each other, as well as $V_H$ domains that are similar to each other. In other words, in certain embodiments the $V_H$ or $V_L$ domains of two different related antibodies usually contain up to about ten (i.e., one, two, three, four or five or more) amino acid differences. An amino acid difference may be present at any position of the variable domain, including in any CDR or in any framework region. Certain related antibodies have H3 CDRs that are almost identical, as well as L3 CDRs that are almost identical. In these embodiments, any two antibodies that are related will have L3 and H3 CDRs that are each identical in length and have near identical sequences (i.e., that contain 0, 1, 2, 3, 4 or 5 amino acid changes). In other words the L3 CDRs of the two antibodies are identical in length and near identical in sequence and the H3 CDRs of the two antibodies are identical in length and near identical in sequence.

Depending on how many sequences are obtained, in certain embodiments the enriched antibodies may be grouped into at least 5 groups, at least 10 groups, at least 20 groups, at least 50 groups, or at least 100 groups or more, e.g., up to 200 or 500 groups or more. Depending how many sequences are obtained, each group may contain from 2 to several hundred or more antibodies.

Once the antibodies have been grouped, a single antibody from each of at least some of the groups (e.g., at least 10%, at least 20%, at least 50 or at least 80% of the groups) is tested in a first bioassay to identify a first antibody that has a biological activity. The bioassay may determine whether the antibody has a biological effect, e.g., an ability to inhibit an interaction between a receptor and a ligand by either binding to the receptor and blocking binding of the ligand, or by binding to the ligand and neutralizing it, or by promoting or inhibiting a cellular phenotype, e.g., cell growth, cell proliferation, cell migration, cell viability (e.g., apoptosis), cell differentiation, cell adherence, cell shape changes (e.g., tubular cell formation), complement dependent cytotoxicity CDC, antibody-dependent cell-mediated cytotoxicity (ADCC), receptor activation, gene expression changes, changes in post-translational modification (e.g., phosphorylation), changes in protein targeting (e.g., NFκB localization etc.), etc., or inhibition of receptor multimerization (e.g., dimer or trimerization) or receptor-ligand interactions, etc. Such bioassays are well known in the art. The term "bioassay" is intended to exclude assays in which only the ability of an antibody to bind to a target is read. Bioassays useful in this method are numerous, and include but are not limited to cellular assays in which a cellular phenotype is measured, e.g., gene expression assays; and in vivo assays that involve a particular animal (which, in certain embodiments may be an animal model for a condition related to the target). In certain cases, the assay may be a vascularization assay.

Exemplary VEGF bioassays include assays using isolated protein in a cell free systems, in vitro using cultured cells or in vivo assays. Exemplary VEGF assays include, but are not limited to a receptor tyrosine kinase inhibition assay (see, e.g., Cancer Research Jun. 15, 2006; 66:6025-6032), an in vitro HUVEC proliferation assay (FASEB Journal 2006; 20: 2027-2035), an in vivo solid tumor disease assay (U.S. Pat. No. 6,811,779) and an in vivo angiogenesis assay (FASEB Journal 2006; 20: 2027-2035). These assays are well known in the art. The descriptions of these assays are hereby incorporated by reference.

Exemplary TNF-α bioassays include in vitro assays using cell free systems or using cultured cells or in vivo assays. As such, TNF-α assays include in vitro human whole blood assay and cell mediated cytotoxicity assay (U.S. Pat. No. 6,090,382), in vitro tumor human killing assay (see, e.g., published U.S. patent application 20040185047), in vivo tumor regression assay (USP Application 20040002589). Additional TNF-α assays are described in a variety of publications, including US PG Pub Nos. 20040151722, 20050037008, 20040185047, 20040138427, 20030187231, 20030199679, and Balazovich (Blood 1996 88: 690-696).

Exemplary PD-1 and PD-L1 bioassay include in vitro assays using cell free systems or using cultured cells or in vivo assays, such as described in a variety of publications, including US 20100055102 A1 and WO 2012018538 A2.

A subject antibody inhibits at least one activity of its target in the range of about 20% to 100%, e.g., by at least about 20%, at least about 30%, at least about 40%, at least about 50%, at least about 60%, usually up to about 70%, up to about 80%, up to about 90% or more. In certain assays, a subject antibody may inhibit its target with an IC50 of $1 \times 10^{-7}$ M or less (e.g., $1 \times 10^{-7}$ M or less, $1 \times 10^{-8}$ M or less, $1 \times 10^{-9}$ M or less, usually to $1 \times 10^{-12}$ M or $1 \times 10^{-13}$ M). In assays in which a mouse is employed, a subject antibody may have an ED50 of less then 1 μg/mouse (e.g., 10 ng/mouse to about 1 μg/mouse). In certain embodiments, a subject antibody may be contacted with a cell in the presence of a ligand, and a ligand response phenotype of the cell is monitored.

In this embodiment, the antibodies tested in the bioassay may contain naturally paired heavy and light chain variable domains, or non-naturally paired heavy and light chains (i.e., heavy and light chain variable domains from different antibodies of the same lineage group). Since the antibodies are from the same lineage group, it is expected that such antibodies will be functional.

After a first antibody that has a biological activity has been identified, further antibodies that are in the same lineage group as the first antibody are tested in a second bioassay, thereby identifying a second antibody that has the same biological activity as the first antibody. In certain cases at least 10%, at least 20%, at least 50%, or at least 80% of the antibodies in the same lineage group are tested. The first bioassay may be the same as or different to the second bioassay. In certain embodiments, a plurality of antibodies is tested, and the antibody with the best properties is chosen for future use.

In particular embodiments, the further antibodies may contain naturally paired heavy and light chain variable domains, or non-naturally paired heavy and light chain variable domains (i.e., heavy and light chain variable domains from different antibodies of the same lineage group). Since the antibodies are from the same lineage group, it is expected that such antibodies will be functional. In particular embodiments, the pairing of the heavy and light chains may be systematic (e.g., every heavy chain is tested in combination with every light chain) or random (e.g., every heavy chain is tested with randomly selected light chains), for example.

In certain embodiments, particularly if the antigen elicits a strong response in the animal, the method may be practiced in the absence of any antigen-based enrichment of antibody producing cells prior to the first bioassay. In these embodiments, the method may involve: a) obtaining the antibody heavy chain sequences and the antibody light chain sequences from a population of B cells of an animal, wherein said population of B cells is not enriched for B cells that produce antibodies that specifically bind to a target antigen, b) grouping the heavy and light chain sequences on the basis of sequence similarity to provide a plurality of groups of antibodies that are related by lineage; c) testing a single antibody from each of the groups in a first bioassay to identify a first antibody that has a biological activity; and, after the first antibody has been identified; and d) testing further antibodies that are in the same group as the first antibody in a second bioassay, thereby identifying a second antibody that has the biological activity.

Figure 2:
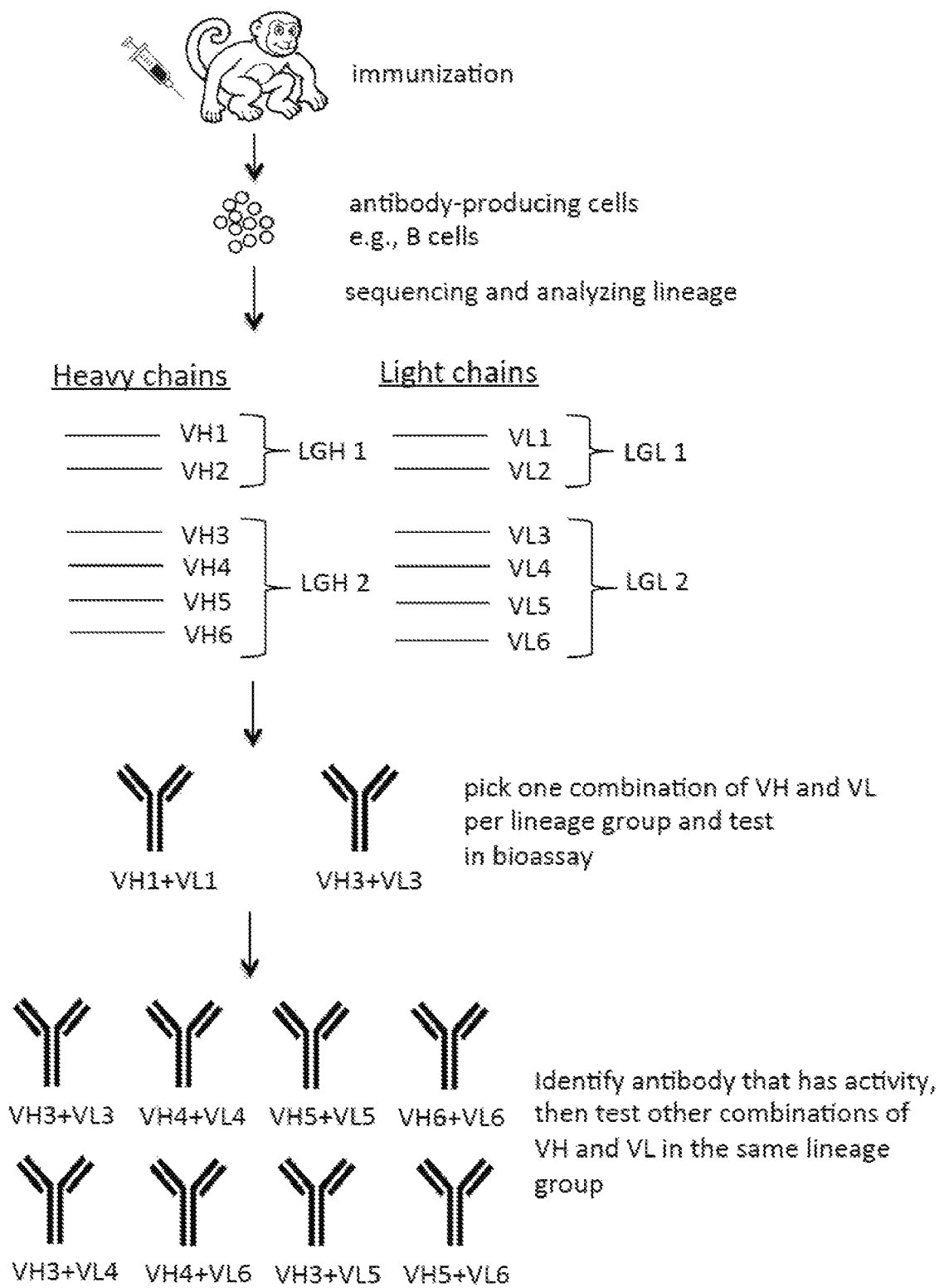
FIG. 2 illustrates a second embodiment of identifying a primate antibody that specifically binds to an antigen.

In certain embodiments, the antibody-producing cells may not need to be enriched or separated into single cells before sequencing (in which case the initial amplification product will contain a mixture of a plurality of different products that can be discriminated by cloning the products or using single molecule sequencing technologies, e.g., high throughput sequencing). One such embodiment of the method is illustrated in FIG. 2. With reference to FIG. 2, the embodiment of the method may involve immunizing a non-human primate animal with a selected antigen. A population of antibody-producing cells is collected from the immunized primate animal. Nucleic acids are prepared from the bulk population of the antibody-producing cells. Nucleic acids encoding the heavy chains and light chains (or in certain cases, variable regions of the heavy chains and light chains) of the antibodies may be amplified. The amino acid sequences of variable region of the heavy chains and light chains of the antibodies produced by the population of antibody-producing cells are obtained by sequencing the nucleic acids encoding the heavy chains and light chains of the antibodies. The sequences are analyzed and put into lineage groups which, as discussed above, are groups of sequences that are derived from antibodies that are produced by cells that share a common B cell ancestor. Such sequences generally are very similar. For example, heavy chain sequences in the same lineage group have H3 CDRs of identical length and near identical sequence, e.g., less than 5 amino acid substitutions. Likewise, light chain sequences in the same lineage group have L3 CDRs of identical length and a near identical sequence, e.g., less than 5 amino acid substitutions. In FIG. 2, six heavy chain variable region sequences, $V_H1$ to $V_H6$, are grouped into two lineage groups, i.e., $V_H1$ and $V_H2$ are in lineage group 1 ($LG_H1$), and $V_H3$, $V_H4$, $V_H5$ and $V_H6$ are in lineage group 2 ($LG_H2$). Independently, six light chain sequences, $V_L1$ to $V_L6$ are grouped into two lineage groups, i.e., $V_L1$ and $V_L2$ are in lineage group 1 ($LG_L1$), and $V_L3$, $V_L4$, $V_L5$ and $V_L6$ are in lineage group 2 ($LG_L2$). After the sequences are put into lineage groups, a single heavy chain from at least one of the lineage group, e.g., $V_H1$ from heavy chain lineage group 1, $V_H3$ from heavy chain lineage group 2 is selected and combined with a single light chain from at least one of the lineage group, e.g., $V_L1$ from light chain lineage group 1, $V_L3$ from light chain lineage group 2, respectively to form antibodies for testing in a bioassay, where the bioassay identifies an antibody with a biological activity (e.g., a blocking or neutralizing activity). Once an antibody having a biological activity has been identified, e.g., an antibody having sequences VH3 paired with VL3, other antibodies contain sequences from the same lineage groups as the identified antibody are tested to identify a second antibody that has the same biological activity as the first antibody. In the example shown in FIG. 1, antibodies having sequences $V_H3$ paired with $V_L3$, $V_H4$ paired with $V_L4$, $V_H5$ paired with $V_L5$, and $V_H6$ paired with $V_L6$, $V_H3$ paired with $V_L4$, $V_H4$ paired with $V_L6$, $V_H3$ paired with $V_L5$ and $V_H5$ paired with $V_L6$ are tested.

In certain embodiments, further analysis of the lineage trees may be needed to decide which heavy chain lineage group pairs with a light chain lineage group. In one embodiment, the size of the lineage group may be used to decide how to pair heavy chain lineage groups with light chain groups. The heavy chain lineage group that has the most members is paired with the light chain lineage group that has the most members. The heavy chain lineage group that has the second most members is paired with the light chain lineage group that has the second most members, and so on.

In certain embodiments, the pairing of heavy chain lineage group with light chain lineage group may be decided based on the heavy chain and light chain sequence obtained from a lead antibody (or antibodies). In one embodiment, a large population of antibody producing cells (e.g., more than 10,000 cells, 20,000 cells, 50,000 cells, 100,000 cells, 200,000 cells, 500,000 cells, 1,000,000 cells or more) is obtained from the immunized non-human primate animal. Nucleic acids are prepared from the bulk population of the antibody-producing cells and a large population (e.g., more than 100,000 sequences, 200,000 sequences, 500,000 sequences, 1,000,000 sequences) of heavy chain sequences and light chain sequences is obtained via high throughput sequencing. The large population of heavy chain and light chain sequences are analyzed to group into lineage groups as described above. In parallel, a small population (e.g., about 5 cell, 10 cells, 20 cells, 50 cells, 100 cells, 200 cells, 500 cells usually not more than 1,000 cells) of antibody producing cells is enriched for binding to specific target and separated into single cells. The heavy chain and light chain sequence for each single cell is obtained by sequencing the nucleic acids encoding the heavy chain and light chain of the antibody. The heavy chain and light chain sequences obtained from the small population of single cells are analyzed to put into the lineage groups obtained from the large population of antibody producing cells. The paring of heavy chain and light chain sequences from each single cell then provides a blueprint for the pairing of heavy chain lineage group and light chain lineage group.

In certain embodiments, the subject method may involve immunizing a non-human primate animal with a selected antigen, and testing a plurality of antibodies produced by a first portion of an antibody producing organ of the animal (e.g., a first portion of the spleen, a first portion of the lymph nodes, a first portion of bone marrow, or a first portion of the peripheral blood mononuclear cell (PBMC) population in the bloodstream of the animal, etc.) in a bioassay to identify a first antibody that has a biological activity. In these embodiments, the first and second portions of an antibody-producing organ need not be spatially separated in the organ. Rather, since a first portion or an organ can be made by, for example, making a single cell suspension of the organ and then removing part of the suspension, the first and second portions of an organ may be interspersed with one another in the organ. For example, antibody A is identified as having a biological activity. The nucleotide sequence encoding the and IgL chain of the antibody is obtained. Based on these sequences, PCR primers that are specific for the heavy and light chains of antibodies that are in the same lineage group as the identified antibody are designed, and used to obtain from the second portion of the antibody producing organ the sequences of further antibodies that are in the same lineage group as the identified antibody. The further antibodies are tested, and a second antibody from the same lineage group and also having the same biological activity as the first antibody is identified.

Many exemplary aspects of this alternative method, e.g., which antigens and bioassays can be employed in the method, etc., are discussed above. In certain embodiments, a lead antibody obtained from a first portion of an antibody-producing organ is identified using a bioassay as disclosed above. In one embodiment, heavy and light chain sequences are directly amplified from PBMCs, and recombinant antibodies are expressed in a different cell (e.g., as described in US20040067496) prior to screening. In another embodiment, a phage display library is constructed from the RNA made from a portion of the spleen of an animal, and the phage display library is screened. The first, biologically active antibody is identified, and the nucleic acid encoding that antibody is sequenced.

In certain embodiments, polynucleotides encoding the variable heavy and variable light domains of lineage-related antibodies may be amplified from the same animal as the first antibody by "CDR-anchored PCR", i.e., using pairs of primers that each contains a primer that is complementary to a CDR-encoding region of the parent antibody cDNA. In these embodiments, the method may include: a) obtaining the nucleotide sequences of: i) a heavy chain-encoding nucleic acid that encodes the variable heavy chain of a first antibody of an immunized animal; and ii) a variable light chain-encoding nucleic acid that encodes the light chain of the first antibody; b) obtaining the amino acid sequence of the variable domains of the heavy and light chains of further antibodies from the immunized animal, using: i) a first primer pair that includes a first primer that is complementary to a CDR-encoding region of the heavy chain-encoding nucleic acid; and ii) a second primer pair that includes a second primer that is complementary to a CDR-encoding region of the light chain-encoding nucleic acid. After the amino acid sequences of the variable domains of the further antibodies have been determined by translation of the obtained nucleotide sequences, the amino acid may be analyzed using the above methods to confirm that they are related by lineage to the first antibody (e.g., analyzed to determine whether the amino acid sequences of the heavy and light chains are at least 80% identical to those of the parent antibody and whether the heavy and light chain CDR3 regions are of identical length of near identical sequence etc. as discussed above).

As would be readily apparent, a variety of techniques are available for amplifying sequences that encode further antibodies from an animal after the nucleotide sequence encoding a first antibody has been obtained from that animal. For example, sequences encoding the heavy and light chains of the second antibody may be amplified using inverse PCR (e.g., using two primers that face away from each other) or by anchored PCR using a specific (where a specific primer may be complementary to a different sequence of the first antibody, e.g., a different CDR sequence) or "universal" primer (where a universal primer is complementary to a sequence that is present in a plurality of different antibody-encoding polynucleotides), where one of the primers is complementary to first CDR-encoding region using cDNA as a template. In certain cases, a universal primer may be complementary to a sequence that is in at least 10% (e.g., at least 20% at least 40% at least 50% or at least 80%) of all heavy or light chain encoding cDNAs obtainable from the animal (e.g., complementary to nucleic acid encoding a conserved sequence that is present in the constant region or secretion signal of the antibodies). In other embodiments, the universal primer may be complementary to flanking sequences in the vector into which cDNA from the animal is cloned or to linkers ligated onto the cDNA, for example.

In one embodiment, two amplification reactions are performed using cDNA as a template, where the first reaction amplifies the heavy chain variable domain-encoding nucleic acid for the second antibody and the second reaction amplifies the light chain variable domain-encoding nucleic acid for the second antibody. In this embodiment: a) the first reaction uses: i) a CDR-specific primer that is complementary to a CDR-encoding region (i.e., the CDR1, CDR2 or CDR3 region) of the heavy chain-encoding nucleic acid of the first antibody and ii) a universal second primer that is complementary to a non-variable domain-encoding region of the antibody heavy chain cDNA, e.g., to a sequence that encodes the constant domain or secretion signal of the heavy chain of the first antibody, as illustrated in the examples section of this disclosure; and b) the second reaction uses i) a CDR-specific primer that is complementary to a CDR-encoding region (i.e., the CDR1, CDR2 or CDR3 region) of the light chain-encoding nucleic acid of the first antibody and ii) a universal second primer that is complementary to a non-variable domain-encoding region of the antibody light chain cDNA, e.g., to a sequence that encodes the constant domain or secretion signal of the light chain of the first antibody.

Several strategies for cloning antibody sequences by PCR are known and may be readily adapted for use in the instant method (e.g., by using a CDR-specific primer in addition to a disclosed primer). Such strategies include those described by: LeBoeuf (Cloning and sequencing of immunoglobulin variable-region genes using degenerate oligodeoxyribonucleotides and polymerase chain reaction. Gene. 1989 82:371-7), Dattamajumdar (Rapid cloning of any rearranged mouse immunoglobulin variable genes Immunogenetics. 1996 43:141-51), Kettleborough (Optimization of primers for cloning libraries of mouse immunoglobulin genes using the polymerase chain reaction Eur. J. Immunol. 1993 23:206-11), Babcook (A novel strategy for generating monoclonal antibodies from single, isolated lymphocytes producing antibodies of defined specificities Proc. Natl. Acad. Sci. 1996 93: 7843-7848) and Williams (Structural diversity in domains of the immunoglobulin superfamily. Cold Spring Harb. Symp. Quant. Biol. 1989 54:637-47) as well as many others. In certain cases, the second primer may be a mixture of different primers or degenerate primers, for example.

The heavy chain CDR-specific primer may be complementary to the sequence that encodes the CDR1, CDR2 or CDR3 region of the heavy chain of the first antibody and, likewise, the light chain CDR-specific primer may be complementary to the sequence that encodes the CDR1, CDR2 or CDR3 region of the light chain of the first antibody. In certain embodiments, a particular CDR-specific primer may be chosen because the CDR sequence to which it binds may be known to be less variable than other CDR sequences.

The above-described CDR-anchored method is effective because most sequence diversity between the variable domains in different families of antibodies that are related by lineage is in the CDR regions (i.e., the CDRs are quite variable between different families of antibodies), whereas the sequence of the CDR regions is relatively constant within the antibodies of a single family of antibodies that are related by lineage. Because the method uses primers that are complementary to sequence that are highly variable between different families of related antibodies, only related antibodies should be successfully amplified by the method.

In this embodiment, an amplification reaction may be performed using cDNA made from a second portion of the antibody-producing organ. For example, the amplification reaction may be done using nucleic acid obtained from single cells (or cultures of the same) or nucleic acid obtained from pooled cells (e.g., pools of different antibody-producing cells that each contain cDNA). Pools may contain cDNA from at least 10, at least 100 or at least 1,000 different antibody cells, for example. Amplification products of the expected size may be sequenced directly or cloned and sequenced using known methods.

Depending on the antigen and number of antibody-producing cells in the second portion of the antibody-producing organ, the heavy and light chain variable sequences for at least 5, at least 10, at least 20, at least 50 or at least 100 or more, e.g., up to 200, up to 500, 1,000, 5,000 or 10,000 or more sequences may be obtained.

The further antibodies are tested in a second bioassay to identify a second antibody that has the same biological activity as the first antibody. As noted above, the first and second bioassays may be the same or different. In certain cases at least 30% (e.g., at least 70%, at least 80%, or at least 90%) of the lineage-related antibodies are tested in the bioassay. In this embodiment, the further antibodies may contain naturally paired heavy and light chain variable domains, or non-naturally paired heavy and light chains (i.e., heavy and light chain variable domains from different antibodies of the same lineage group). Since the antibodies are from the same lineage group, it is expected that such antibodies will be functional. In particular embodiments, the pairing of the heavy and light chains may be systematic (e.g., every heavy chain is tested in combination with every light chain) or random (e.g., every heavy chain is tested with randomly selected light chains), for example.

An antibody produced by the instant methods finds use in diagnostics, in antibody imaging, and in treating diseases treatable by monoclonal antibody-based therapy. In particular, an antibody humanized by the instant methods may be used for passive immunization or the removal of unwanted cells or antigens, such as by complement mediated lysis or antibody mediated cytotoxicity (ADCC), all without substantial immune reactions (e.g., anaphylactic shock) associated with many prior antibodies. For example, the antibodies of the present invention may be used as a treatment for a disease where the surface of an unwanted cell specifically expresses a protein recognized the antibody (e.g. HER2, or any other cancer-specific marker) or the antibodies may be used to neutralize an undesirable toxin, irritant or pathogen. Humanized antibodies are particularly useful for the treatment of many types of cancer, for example colon cancer, lung cancer, breast cancer prostate cancer, etc., where the cancers are associated with expression of a particular cellular marker. Since most, if not all, disease-related cells and pathogens have molecular markers that are potential targets for antibodies, many diseases are potential indications for humanized antibodies. These include autoimmune diseases where a particular type of immune cells attack self-antigens, such as insulin-dependent diabetes mellitus, systemic lupus erythematosus, pernicious anemia, allergy and rheumatoid arthritis; transplantation related immune activation, such as graft rejection and graft-vs-host disease; other immune system diseases such as septic shock; infectious diseases, such as viral infection or bacteria infection; cardiovascular diseases such as thrombosis and neurological diseases such as Alzheimer's disease.

An antibody of particular interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a monoclonal antibody of interest will cause a subject animal to be more similar to an equivalent animal that is not suffering from the disease or condition. Monoclonal antibodies that have therapeutic value that have been identified using the methods and compositions of the invention are termed "therapeutic" antibodies.

Methods for Generating Humanized Antibodies

In another aspect, the present disclosure relates to methods for generating humanized antibodies.

In certain embodiments, the method for producing a humanized antibody that binds to an antigen, comprises: a) identify an antibody that binds to the antigen according to the method as described above; b) grafting a sequence that comprises a CDR region from said antibody identified in step a) into a human antibody framework to generate a humanized antibody; and c) testing said humanized antibody generated in step b) for binding to the antigen.

As a first step in the method, a primate antibody that binds to the antigen is identified using the method as described above. The amino acid sequence of the primate antibody framework region is then compared with antibody framework regions of human antibodies to find a human antibody framework substantially identical to the primate antibody framework, e.g., the human antibody framework is at least 50%, 60%, 70%, 80%, 90%, 95%, 99% identical to the framework of said antibody identified in step a). In certain embodiments, the human antibody framework is identical to the framework of said antibody identified in step a).

After the human antibody framework that is substantially identical to the identified primate antibody is found, the CDR sequences (i.e., H1 CDR, H2 CDR and H3 CDR, L1 CDR, L2 CDR, L3 CDR) of the identified primate antibody are grafted to the found human antibody framework to generate a humanized antibody.

The method of grafting CDR sequences to a human antibody framework is known in the art. In certain embodiments, a nucleotide sequence that encodes the CDR sequence is isolated and inserted into a nucleotide sequence encoding the human antibody framework. Typically, nucleotide sequences that encode CDR1, CDR2 and CDR3 of the identified primate antibody are isolated and inserted into the nucleotide sequence encoding the human antibody framework. In certain embodiments, when the human antibody framework is virtually identical, e.g., at least 90%, 95%, 99% identical to the identified primate antibody, the nucleotide sequence encoding the primate antibody is mutagenized to substitute amino acid residues in the primate framework that are different from those in the human antibody framework with the corresponding amino acid residues in the human antibody framework, thus generating a humanized antibody with human antibody framework. In certain embodiments, the primate antibody framework is identical to the human antibody framework and the primate antibody can be regarded herein as a humanized antibody.

Methods of identifying a Primate T-Cell Receptor that Binds to an Antigen

In an aspect, the present invention relates to a method of identifying a primate T-cell receptor that binds to an antigen. In certain embodiments, the method may comprise the steps of: a) obtaining: a plurality of T-cell receptor (TCR) α-chain sequences and a plurality of TCR β-chain sequences from a population of T cells of a primate that has been immunized by the antigen; b) grouping said obtained plurality of TCR α-chain sequences into a plurality of α-chain groups and, independently, grouping said obtained plurality of TCR β-chain sequences into a plurality of β-chain groups, wherein: TCR α-chain sequences that comprise CDR3 regions that are of the same length and contain up to five amino acid substitutions relative to one another are grouped together; and TCR β-chain sequences that comprise CDR3 regions that are of the same length and contain up to five amino acid substitutions relative to one another are grouped together; c) selecting an α-chain group and an β-chain group from the groups grouped in step b); d) pairing a α-chain sequence and a β-chain sequence from the groups selected in step c); and e) testing a TCR comprising the α-chain and β-chain sequences paired in d) for binding to the antigen.

Figure 3:
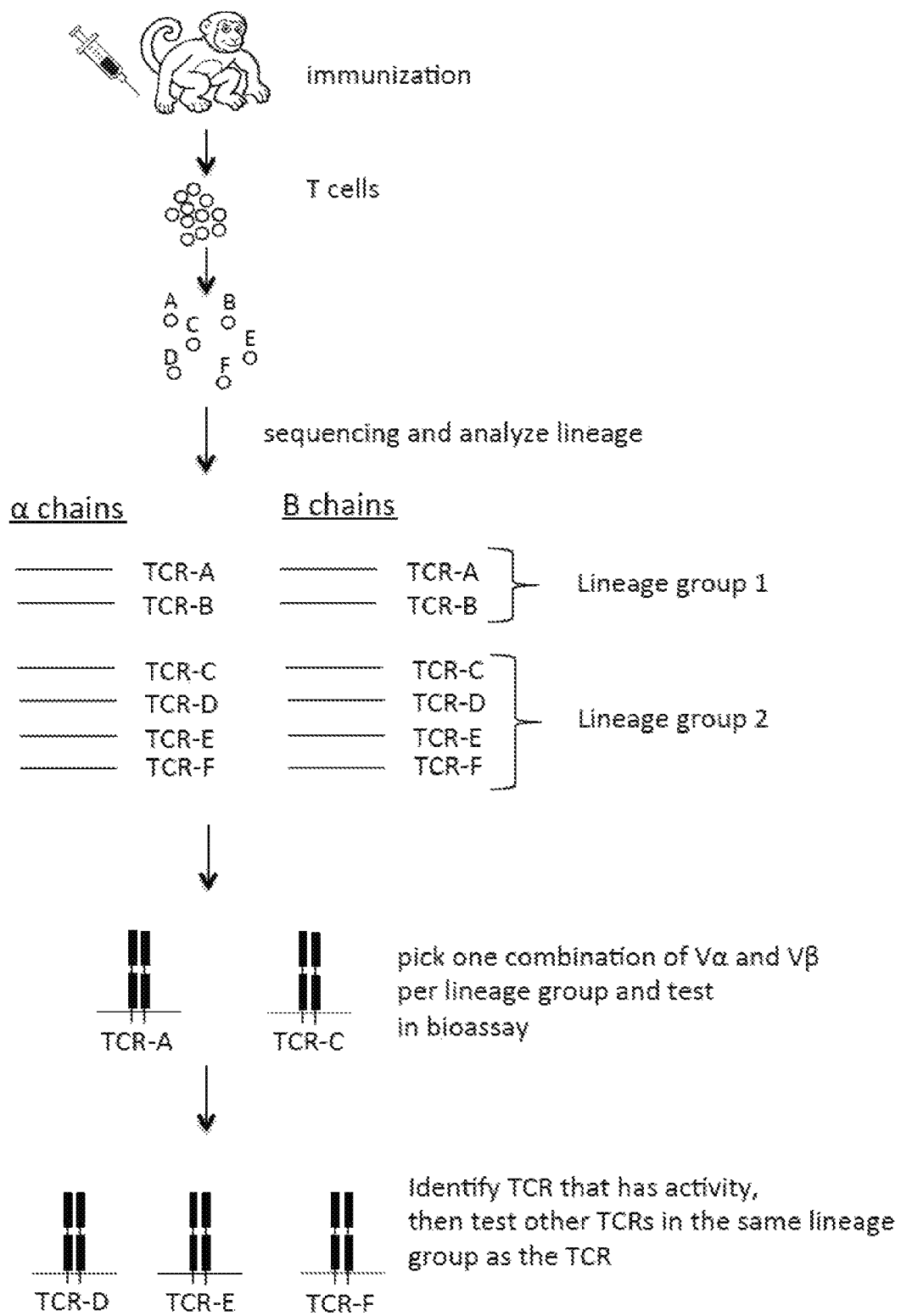
FIG. 3 illustrates an embodiment of identifying a primate TCR that specifically binds to an antigen.

One embodiment of the subject method is illustrated in FIG. 3. With reference to FIG. 3, the embodiment of the method may involve immunizing a non-human primate animal with a selected antigen. In FIG. 3, six different T cells A-F that produce antibodies that bind to a target antigen are enriched from a larger population of antibody producing cells. However, in many embodiments, there may be several hundred, several thousand or several million T cells. Each of these cells produces a natural TCR that contains a naturally paired α-chain and β-chain. The amino acid sequences of the α-chain and β-chain of the TCR produced by the enriched T cells are obtained by sequencing the nucleic acids encoding the α-chain and β-chain of the TCRs (in certain cases, only the nucleic acids encoding the variable region of the α-chain and β-chain of the TCRs are sequenced), and the sequences are analyzed and put into lineage groups which, as discussed above, are groups of TCRs that are produced by cells that share a common T cell ancestor. Such antibodies generally have very similar sequences, and have α-chain CDR3s of identical length and near identical sequence as well as β-chain CDR3s of identical length and a near identical sequence. In the embodiment shown in FIG. 3, the six T cells produce TCRs (TCR-A to TCR-F) that are in two lineage groups (i.e., lineage groups 1 and 2, where TCR-A and TCR-B are in lineage group 1 and TCR-C, TCR-D, TCR-E and TCR-F are in lineage group 2). After the TCRs have been placed into lineage groups, a single TCR (or, in certain cases, multiple TCRs from each lineage group) from at least one of the lineage group, e.g., TCR-A from lineage group 1 and TCR-C from lineage group 2, is selected for testing in a bioassay, where a bioassay identifies a TCR with a biological activity (e.g., T cell activation assay). Once a TCR having a biological activity has been identified, e.g., TCR-C, other TCRs from the same lineage group as the identified TCR are tested to identify a second TCR that has the same biological activity as the first TCR. In the example shown in FIG. 3, TCR-D, E and F, which belong to the same lineage group as TCR C, are tested.

Many non-human primate animals, including without limitation, gorillas, chimpanzees, orangutans, gibbons, crab-eating macaques, rhesus macaques, pig-tailed macaques, may be used as a source of T cells. In certain embodiments, the non-human primate animals used to provide T cells are rhesus macaques, crab-eating macaques and pigtail macaques. Procedures for immunizing animals are well known in the art, and are described in Harlow et al., ("Antibodies: A Laboratory Manual", First Edition (1988) Cold Spring Harbor, N.Y.).

Suitable antigens include extracellularly-exposed fragments of Her2, GD2, PD-1 (programmed cell death 1), PD-L1 (programmed death-ligand 1), EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL—related ligand), CA125 (carcinoma antigen 125), CEA (carcinoembryonic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine A11), HER2/neu, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFβR (Beta platelet-derived growth factor receptor), PMSA, renal carcinoma antigen G250, RSV, E-Selectin, TGFbeta1, TGFbeta2, TNFalpha, TRAIL-R1, VAP-1 (vascular adhesion protein 1) or TNFα, or the like. In many embodiments, a peptide having the amino acid sequence corresponding to a portion of an extracellular domain of one of the above-listed proteins is employed as an antigen.

In certain embodiments, an affinity purification method is utilized to isolate T cells that produce TCR that bind to an antigen. The antigen with which the animal was immunized may be immobilized on a solid phase and used to selectively retain T cells that express a TCR on their surface that binds to the antigen, while other cells are washed away. The retained cells may then be eluted by a variety of methods, such as by using an excess of the antigen, chaotropic agents, changing the pH, salt concentration, etc. Any of the well-known methods for immobilizing or coupling antigen to a solid phase may be used. For example, when the antigen is a cancer cell, appropriately treated microtiter plate that will bind to cells may be used, such as microtiter plates for cell culture. In the instances where the antigen is a protein, the protein may be covalently attached to a solid phase, for example, SEPHARSE crosslinked agarose beads, by well-known techniques, etc. Alternatively, a labeled antigen may be used to specifically label cells that express an antibody that binds to the antigen and the labeled cells may then be isolated by cell sorting (e.g., by FACS). Cells may also be isolated using magnetic beads or by any other affinity solid phase capture method, protocols for which are known. Exemplary T cell enrichment methods include performing flow cytometry (FACS) of cell populations obtained from a bone marrow, lymph node or other lymph organs. In some embodiments, single or nearly single T cells are deposited in microtiter plates. If the FACS system is employed, sorted cells may be deposited after enrichment directly into a microtiter plate.

Enrichment may decrease the size of the cell population by at least 50%, e.g., at least 60%, at least 70%, at least 80%, at least 90%, at least 95% or at least 99% and in certain cases, the plurality of enriched T cells may be substantially pure, i.e., substantially free of other cells that do not produce a TCR that binds to the antigen, where the term "substantially pure" refers to an isolated population of T cells, in which cells that express TCRs that specifically bind to the antigen make up at least 5%, 10%, 20%, 30%, at least 40%, at least 50%, at least 60%, at least 70% or more of the total population of cells. The enriched population of T cells may be employed as a mixture of cells, or alternatively, they may be used as single cells, e.g., by dilution and deposition into individual wells of a microtiter plate.

The enriched population of T cells may comprise at least 5, at least 10, at least 30, at least 60, at least 100, at least 300, at least 500, at least 1000, at least 5,000, at least 10,000 or at least 100,000, or more T cells.

T cells may be derived from the blood, lymph nodes or bone marrow, as well as from other tissues. T cells may also be prepared from blood collected with an anticoagulant such as heparin or EDTA. The T cells may be further separated from erythrocytes and polymorphs using standard procedures such as centrifugation with Ficoll-Hypaque (Pharmacia, Uppsula, Sweden). T cells may also be prepared from solid tissues such as lymph nodes by dissociation with enzymes such as collagenase and trypsin in the presence of EDTA. In preferred embodiments, T cells are derived from blood, e.g., peripheral blood mononuclear cell (PBMC).

The isolated T cells may be optionally cultured (i.e., grown in media that supports at least one, at least 5 or at least 10 or more cell divisions of the cell) by methods known to one of skill in the art after they have been deposited.

In certain embodiments, the TCRs produced by the enriched cells are not well characterized. As such, although the T cells are isolated based on the production of TCRs that specifically bind to the antigen, the epitope(s) to which these TCRs bind is unknown, and it is not known if the TCRs have any biological activity (e.g., inducing T cell activation). Additionally, the nucleic acid sequence or the amino acid sequence of the variable regions of α-chain and β-chain of these TCRs are not known.

Sequences encoding α-chain and β-chain may be amplified from the cDNA using techniques well known in the art, such as Polymerase Chain Reaction (pot). See Mullis, U.S. Pat. No. 4,683,195; Mullis et al., U.S. Pat. No. 4,683,195; Polymerase Chain Reaction: Current Communication in Molecular Biology, Cold Springs Harbor Press, Cold Spring Harbor, N.Y., 1989. Briefly, cDNA segments encoding the variable domain of the TCR are exponentially amplified by performing sequential reactions with a DNA polymerase. The reaction is primed by a 5' primer and a 3' DNA primer. In some embodiments, the 3' antisense primer corresponding to a DNA sequence in the constant (or joining) region of the immunoglobulin chain and the 5' primer (or panel of related primers) corresponding to a DNA sequence in the variable region of the α-chain or β-chain. Alternatively, an "anchored polymerase chain reaction" may be performed (see Loh et al., Science 243:217-220, 1989). In this procedure, the first strand cDNA is primed with a 3' DNA primer as above, and a poly(dG tail) is then added to the 3' end of the strand with terminal deoxynucleotidyl transferase. The product is then amplified by PCR using the specific 3' DNA primer and another oligonucleotide consisting of a poly(dC) tail attached to a sequence with convenient restriction sites. In many embodiments, however, the entire polynucleotide encoding a α-chain or β-chain is amplified using primers spanning the start codons and stop codons of both of the α-chain and β-chain cDNAs, however, depending on the amplification products desired, suitable primers may be used. Suitable restriction sites and other tails may be engineered into the amplification oligonucleotides to facilitate cloning and further processing of the amplification products. Amplification procedures using nested primers may also be used, where such nested primers are well known to one of skill in the art. In certain embodiments, the cells may be kept separate from one another (in which case the initial amplification product amplified from a single cell may contain a single species that can be sequenced).

In certain embodiments, at least 1,000 α-chain sequences and at least 1,000 β-chain sequences are obtained.

Once the amino acid sequences of et-chains and β-chains of the TCRs have been obtained, TCRs can be grouped on the basis of sequence similarity to provide a plurality of groups of TCRs that are related by lineage. Methods for performing clonal analysis of TCR sequences are well known and are described in a number of publications including Magori-Cohen (Bioinformatics 2006 22: e332-40), Manske (Clin. Immunol. 2006 120:106-20), Kleinstein (J. Immunol. 2003 171: 4639-49), Clement (Mol. Ecol. 2000 9: 1657-1659), Mehr (J. Immunol, 2004 172 4790-6), Wrammert (Nature 2008 453: 667-672), Scheid (Nature 2009 458: 636-640), which are incorporated by reference herein for disclosure of those methods. The TCRs placed into lineage groups should all be from a single non-human primate animal.

The variable regions of TCRs within a related group of TCRs have amino acid sequences that are very similar. For example, the variable regions of TCRs within a related group of TCRs may have amino acid sequences that are at least about 80% identical (e.g., at least 85% identical, at least 90% identical, at least 95% or at least 98% or at least 99% identical), ignoring any gaps or insertions made to facilitate alignment of the sequences. TCRs within a related group have a variable domain of α-chain that are similar to each other, as well as variable domains of β-chain that are similar to each other. In other words, in certain embodiments the vatiable domains of two different related TCRs usually contain up to about ten (i.e., one, two, three, four or five or more) amino acid differences. An amino acid difference may be present at any position of the variable domain, including in any CDR or in any framework region. Certain related TCRs have α-chain CDR3s that are almost identical, as well as β-chain CDR3s that are almost identical. In these embodiments, any two TCRs that are related will have α-chain CDR3s and β-chain CDR3s that are each identical in length and have near identical sequences (i.e., that contain 0, 1, 2, 3, 4 or 5 amino acid changes). In other words the β-chain CDR3s of the two TCRs are identical in length and near identical in sequence and the α-chain CDR3s of the two TCRs are identical in length and near identical in sequence.

Depending on how many sequences are obtained, in certain embodiments the enriched TCRs may be grouped into at least 5 groups, at least 10 groups, at least 20 groups, at least 50 groups, or at least 100 groups or more, e.g., up to 200 or 500 groups or more. Depending how many sequences are obtained, each group may contain from 2 to several hundred or more TCRs.

Once the TCRs have been grouped, a single TCR from each of at least some of the groups (e.g., at least 10%, at least 20%, at least 50 or at least 80% of the groups) is tested in a first bioassay to identify a first TCR that has a biological activity. The bioassay may determine whether the TCR has a biological effect, e.g., an ability to activate immune response or by promoting or inhibiting a cellular phenotype, e.g., cell growth, cell proliferation, cell migration, cell viability (e.g., apoptosis), cell differentiation, cell adherence, cell shape changes (e.g., tubular cell formation), complement dependent cytotoxicity CDC, antibody-dependent cell-mediated cytotoxicity (ADCC), receptor activation, gene expression changes, changes in post-translational modification (e.g., phosphorylation), changes in protein targeting (e.g., NFκB localization etc.), etc., or inhibition of receptor multimerization (e.g., dimer or trimerization) or receptor-ligand interactions, etc. Such bioassays are well known in the art. The term "bioassay" is intended to exclude assays in which only the ability of a TCR to bind to a target is read. Bioassays useful in this method are numerous, and include but are not limited to cellular assays in which a cellular phenotype is measured, e.g., gene expression assays; and in vivo assays that involve a particular animal (which, in certain embodiments may be an animal model for a condition related to the target). In certain cases, the assay may be a vascularization assay.

In certain embodiments, the TCRs tested in the bioassay may contain naturally paired α-chain and β-chain variable domains, or non-naturally paired α-chain and β-chain (i.e., α-chain and β-chain variable domains from different TCRs of the same lineage group). Since the TCRs are from the same lineage group, it is expected that such TCRs will be functional.

After a first TCR that has a biological activity has been identified, further TCRs that are in the same lineage group as the first TCR are tested in a second bioassay, thereby identifying a second TCR that has the same biological activity as the first TCR. In certain cases at least 10%, at least 20%, at least 50%, or at least 80% of the TCRs in the same lineage group are tested. The first bioassay may be the same as or different to the second bioassay. In certain embodiments, a plurality of TCRs is tested, and the TCR with the best properties is chosen for future use.

In particular embodiments, the further TCRs may contain naturally paired α-chain and β-chain variable domains, or non-naturally paired α-chain and β-chain variable domains (i.e., α-chain and β-chain variable domains from different TCRs of the same lineage group). Since the TCRs are from the same lineage group, it is expected that such TCRs will be functional. In particular embodiments, the pairing of the α-chain and β-chain may be systematic (e.g., every α-chain is tested in combination with β-chain) or random (e.g., every α-chain is tested with randomly selected and β-chain), for example.

In certain embodiments, particularly if the antigen elicits a strong response in the animal, the method may be practiced in the absence of any antigen-based enrichment of T cells prior to the first bioassay. In these embodiments, the method may involve: a) obtaining the TCR α-chain sequences and the β-chain sequences from a population of T cells of an animal, wherein said population of T cells is not enriched for T cells that produce TCRs that specifically bind to a target antigen, b) grouping the α-chain and β-chain sequences on the basis of sequence similarity to provide a plurality of groups of TCRs that are related by lineage; c) testing a single TCR from each of the groups in a first bioassay to identify a first TCR that has a biological activity; and, after the first TCR has been identified; and d) testing further TCRs that are in the same group as the first TCR in a second bioassay, thereby identifying a second TCR that has the biological activity.

Figure 4:
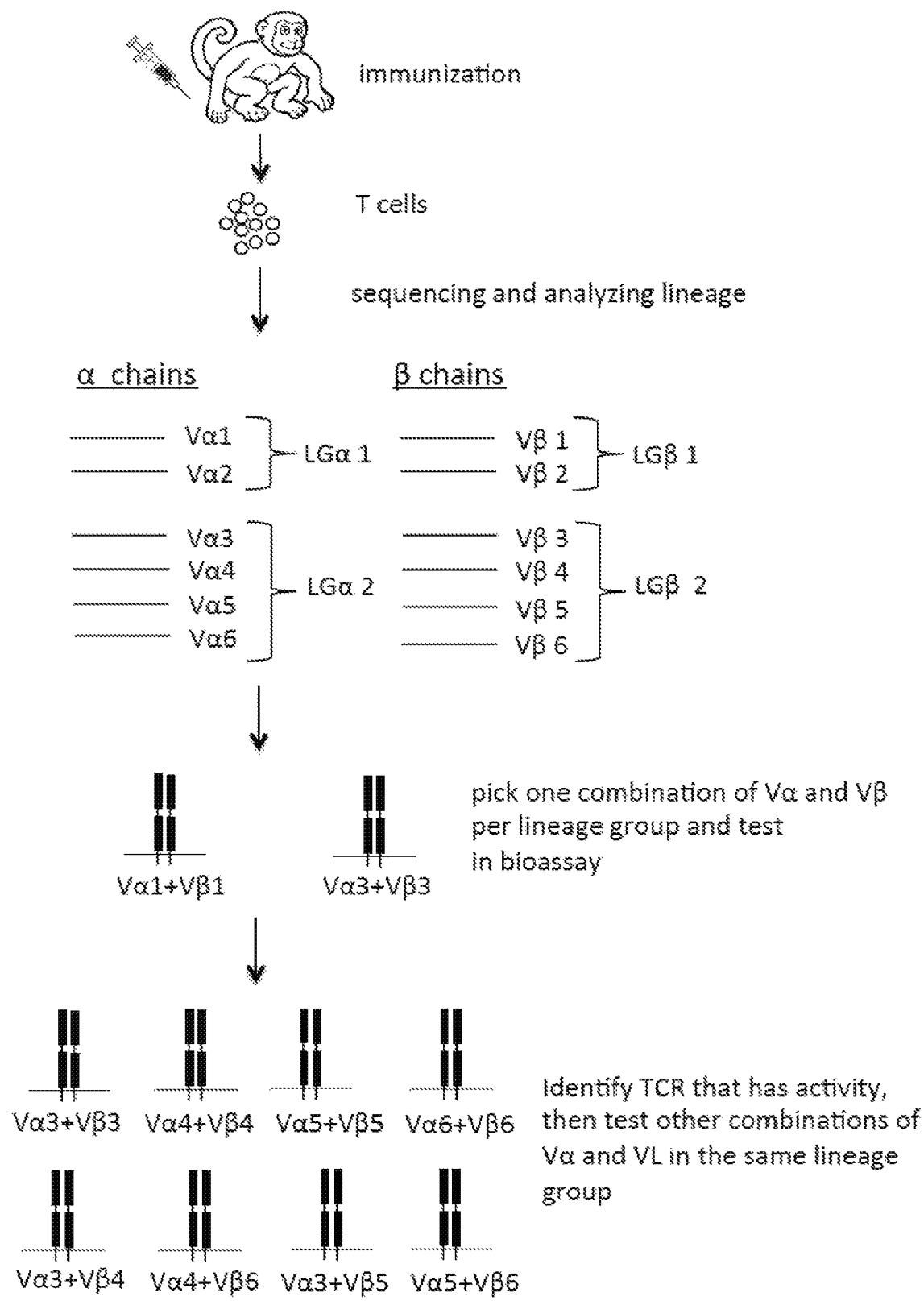
FIG. 4 illustrates a second embodiment of identifying a primate TCR that specifically binds to an antigen.

In certain embodiments, the T cells may not need to be enriched or separated into single cells before sequencing (in which case the initial amplification product will contain a mixture of a plurality of different products that can be discriminated by cloning the products or using single molecule sequencing technologies, e.g., high throughput sequencing). One such embodiment of the method is illustrated in FIG. 4. With reference to FIG. 4, the embodiment of the method may involve immunizing a non-human primate animal with a selected antigen. A population of T cells is collected from the immunized primate animal. Nucleic acids are prepared from the bulk population of the T cells. Nucleic acids encoding the α-chain and β-chain (or in certain cases, variable regions of the α-chain and β-chain) of the TCR may be amplified. The amino acid sequences of variable region of the α-chain and β-chain of the TCRs produced by the population of T cells are obtained by sequencing the nucleic acids encoding the α-chain and β-chain of the TCRs. The sequences are analyzed and put into lineage groups which, as discussed above, are groups of sequences that are derived from TCRs that are produced by cells that share a common T cell ancestor. Such sequences generally are very similar. For example, α-chain sequences in the same lineage group have CDR3s of identical length and near identical sequence, e.g., less than 5 amino acid substitutions. Likewise, β-chain sequences in the same lineage group have CDR3s of identical length and a near identical sequence, e.g., less than 5 amino acid substitutions. In FIG. 4, six α-chain variable region sequences, Vα1 to Vα6, are grouped into two lineage groups, i.e., Vα1 and Vα2 are in lineage group 1 (LGα1), and Vα3, Vα4, Vα5 and Vα6 are in lineage group 2 (LGα2). Independently, six β-chain sequences, Vβ1 to Vβ6 are grouped into two lineage groups, i.e., Vβ1 and Vβ2 are in lineage group 1 (LGβ1), and Vβ3, Vβ4, Vβ5 and Vβ6 are in lineage group 2 (LGβ32). After the sequences are put into lineage groups, a single heavy chain from at least one of the lineage group, e.g., Vα1 from heavy chain lineage group 1, Vα3 from α-chain lineage group 2 is selected and combined with a single β-chain from at least one of the lineage group, e.g., Vβ1 from β-chain lineage group 1, Vβ3 from β-chain lineage group 2, respectively to form TCRs for testing in a bioassay, where the bioassay identifies an TCR with a biological activity. Once a TCR having a biological activity has been identified, e.g., an TCR having sequences Vα3 paired with Vβ3, other TCRs contain sequences from the same lineage groups as the identified TCR are tested to identify a second. TCR that has the same biological activity as the first TCR. In the example shown in FIG. 4, TCRs having sequences Vα3 paired with Vβ3, Vα4 paired with Vβ4, Vα5 paired with Vβ5, and Vα6 paired with Vβ6, Vα3 paired with Vβ4, Vα4 paired with Vβ6, Vα3 paired with Vβ5 and Vα5 paired with Vβ6 are tested.

In certain embodiments, further analysis of the lineage trees may be needed to decide which α-chain lineage group pairs with a β-chain lineage group. In one embodiment, the size of the lineage group may be used to decide how to pair α-chain lineage groups with β-chain groups. The α-chain lineage group that has the most members is paired with the β-chain lineage group that has the most members. The α-chain lineage group that has the second most members is paired with the β-chain lineage group that has the second most members, and so on.

In certain embodiments, the pairing of a chain lineage group with β-chain lineage group may be decided based on the α-chain and β-chain sequence obtained from a lead TCR (or TCRs). In one embodiment, a large population of T cells (e.g., more than 10,000 cells, 20,000 cells, 50,000 cells, 100,000 cells, 200,000 cells, 500,000 cells, 1,000,000 cells or more) is obtained from the immunized non-human primate animal. Nucleic acids are prepared from the bulk population of the T cells and a large population (e.g., more than 100,000 sequences, 200,000 sequences, 500,000 sequences, 1,000,000 sequences) of α-chain sequences and β-chain sequences is obtained via high throughput sequencing. The large population of α-chain and β-chain sequences are analyzed to group into lineage groups as described above. In parallel, a small population (e.g., about 5 cell, 10 cells, 20 cells, 50 cells, 100 cells, 200 cells, 500 cells usually not more than 1,000 cells) of T cells is enriched for binding to specific target and separated into single cells. The α-chain and β-chain sequence for each single cell is obtained by sequencing the nucleic acids encoding the α-chain and chain of the antibody. The α-chain and β-chain sequences obtained from the small population of single cells are analyzed to put into the lineage groups obtained from the large population of T cells. The paring of α-chain and β-chain sequences from each single cell then provides a blueprint for the pairing of α-chain lineage group and β-chain lineage group.

In certain embodiments, the subject method may involve immunizing a non-human primate animal with a selected antigen, and testing a plurality of TCRs produced by a first portion of a T cell producing organ of the animal (e.g., a first portion of the lymph nodes, a first portion of bone marrow, or a first portion of the peripheral blood mononuclear cell (PBMC) population in the bloodstream of the animal, etc.) in a bioassay to identify a first TCR that has a biological activity. In these embodiments, the first and second portions of an T cell producing organ need not be spatially separated in the organ. Rather, since a first portion or an organ can be made by, for example, making a single cell suspension of the organ and then removing part of the suspension, the first and second portions of an organ may be interspersed with one another in the organ. For example, TCR A is identified as having a biological activity. The nucleotide sequence encoding the α-chain and β-chain of the TCR is obtained. Based on these sequences, PCR primers that are specific for the α-chain and β-chain of TCRs that are in the same lineage group as the identified TCR are designed, and used to obtain from the second portion of the T cell producing organ the sequences of further TCRs that are in the same lineage group as the identified TCR. The further TCRs are tested, and a second TCR from the same lineage group and also having the same biological activity as the first TCR is identified.

Many exemplary aspects of this alternative method, e.g., which antigens and bioassays can be employed in the method, etc., are discussed above. In certain embodiments, a lead TCR obtained from a first portion of a T cell producing organ is identified using a bioassay as disclosed above. In one embodiment, α-chain and β-chain sequences are directly amplified from PBMCs, and recombinant antibodies are expressed in a different cell (e.g., as described in US20040067496) prior to screening. In another embodiment, a phage display library is constructed from the RNA made from a portion of the lymph node of an animal, and the phage display library is screened. The first, biologically active TCR is identified, and the nucleic acid encoding that TCR is sequenced.

In certain embodiments, polynucleotides encoding the variable α-chain and chain domains of lineage-related. TCRs may be amplified from the same animal as the first TCR by "CDR-anchored PCR", i.e., using pairs of primers that each contains a primer that is complementary to a CDR-encoding region of the parent antibody cDNA. In these embodiments, the method may include: a) obtaining the nucleotide sequences of: i) a α-chain-encoding nucleic acid that encodes the variable α-chain of a first TCR of an immunized animal; and ii) a variable β-chain-encoding nucleic acid that encodes the β-chain of the first TCR; b) obtaining the amino acid sequence of the variable domains of the α-chain and β-chain of further TCRs from the immunized animal, using: i) a first primer pair that includes a first primer that is complementary to a CDR-encoding region of the α-chain-encoding nucleic acid; and ii) a second primer pair that includes a second primer that is complementary to a CDR-encoding region of the β-chain-encoding nucleic acid. After the amino acid sequences of the variable domains of the further TCRs have been determined by translation of the obtained nucleotide sequences, the amino acid may be analyzed using the above methods to confirm that they are related by lineage to the first TCR (e.g., analyzed to determine whether the amino acid sequences of the α-chain and β-chain are at least 80% identical to those of the parent TCR and whether the α-chain and β-chain CDR3 regions are of identical length of near identical sequence etc. as discussed above).

As would be readily apparent, a variety of techniques are available for amplifying sequences that encode further TCRs from an animal after the nucleotide sequence encoding a first TCR has been obtained from that animal. For example, sequences encoding the α-chain and β-chain of the second TCR may be amplified using inverse PCR (e.g., using two primers that face away from each other) or by anchored. PCR using a specific (where a specific primer may be complementary to a different sequence of the first TCR, e.g., a different CDR sequence) or "universal" primer (where a universal primer is complementary to a sequence that is present in a plurality of different TCR-encoding polynucleotides), where one of the primers is complementary to first CDR-encoding region using cDNA as a template. In certain cases, a universal primer may be complementary to a sequence that is in at least 10% (e.g., at least 20% at least 40% at least 50% or at least 80%) of all α-chain and β-chain encoding cDNAs obtainable from the animal (e.g., complementary to nucleic acid encoding a conserved sequence that is present in the constant region of the TCR). In other embodiments, the universal primer may be complementary to flanking sequences in the vector into which cDNA from the animal is cloned or to linkers ligated onto the cDNA, for example.

In one embodiment, two amplification reactions are performed using cDNA as a template, where the first reaction amplifies the α-chain variable domain-encoding nucleic acid for the second TCR and the second reaction amplifies the β-chain variable domain-encoding nucleic acid for the second TCR. In this embodiment: a) the first reaction uses: CDR-specific primer that is complementary to a CDR-encoding region (i.e., the CDR1, CDR2 or CDR3 region) of the α-chain-encoding nucleic acid of the first TCR and ii) a universal second primer that is complementary to a non-variable domain-encoding region of the TCR α-chain cDNA, e.g., to a sequence that encodes the constant domain or secretion signal of the α-chain of the first TCR, as illustrated in the examples section of this disclosure; and b) the second reaction uses i) a CDR-specific primer that is complementary to a CDR-encoding region (i.e., the CDR1, CDR2 or CDR3 region) of the β-chain-encoding nucleic acid of the first TCR and ii) a universal second primer that is complementary to a non-variable domain-encoding region of the TCR β-chain cDNA, e.g., to a sequence that encodes the constant domain or secretion signal of the β-chain of the first TCR.

Several strategies for cloning TCR sequences by PCR are known and may be readily adapted for use in the instant method (e.g., by using a CDR-specific primer in addition to a disclosed primer). In certain cases, the second primer may be a mixture of different primers or degenerate primers, for example.

The α-chain CDR-specific primer may be complementary to the sequence that encodes the CDR1, CDR2 or CDR3 region of the α-chain of the first TCR and, likewise, the β-chain CDR-specific primer may be complementary to the sequence that encodes the CDR1, CDR2 or CDR3 region of the β-chain of the first TCR. In certain embodiments, a particular CDR-specific primer may be chosen because the CDR sequence to which it binds may be known to be less variable than other CDR sequences.

The above-described CDR-anchored method is effective because most sequence diversity between the variable domains in different families of antibodies that are related by lineage is in the CDR regions (i.e., the CDRs are quite variable between different families of TCRs), whereas the sequence of the CDR regions is relatively constant within the TCRs of a single family of TCRs that are related by lineage. Because the method uses primers that are complementary to sequence that are highly variable between different families of related TCRs, only related TCRs should be successfully amplified by the method.

In this embodiment, an amplification reaction may be performed using cDNA made from a second portion of the T-cell-producing organ. For example, the amplification reaction may be done using nucleic acid obtained from single cells (or cultures of the same) or nucleic acid obtained from pooled cells (e.g., pools of different T cells that each contain cDNA). Pools may contain cDNA from at least 10, at least 100 or at least 1,000 different T cells, for example. Amplification products of the expected size may be sequenced directly or cloned and sequenced using known methods.

Depending on the antigen and number of T cells in the second portion of the T-cell-producing organ, the α-chain and β-chain variable sequences for at least 5, at least 10, at least 20, at least 50 or at least 100 or more, e.g., up to 200, up to 500, 1,000, 5,000 or 10,000 or more sequences may be obtained.

The further TCRs are tested in a second bioassay to identify a second TCR that has the same biological activity as the first TCR. As noted above, the first and second bioassays may be the same or different. In certain cases at least 30% (e.g., at least 70%, at least 80%, or at least 90%) of the lineage-related TCRs are tested in the bioassay. In this embodiment, the further TCRs may contain naturally paired α-chain and β-chain variable domains, or non-naturally paired α-chain and β-chain (i.e., α-chain and β-chain variable domains from different TCRs of the same lineage group). Since the TCRs are from the same lineage group, it is expected that such TCRs will be functional. In particular embodiments, the pairing of the α-chain and β-chain may be systematic (e.g., every α-chain is tested in combination with every β-chain) or random (e.g., every α-chain is tested with randomly selected β-chain), for example.

A TCR of particular interest is one that modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the TCR. In general, a TCR of interest will cause a subject animal to be more similar to an equivalent animal that is not suffering from the disease or condition. TCRs that have therapeutic value that have been identified using the methods and compositions of the invention are termed "therapeutic" TCRs.

Numbered Embodiments

1. A method comprising steps of:
  a). obtaining a population of antibody-producing B cells from a primate that has been immunized by an antigen;
  b). obtaining from the population of antibody-producing B cells:
    (i) a plurality of antibody heavy chain sequences and
    (ii) a plurality of antibody light chain sequences;

c). grouping said obtained plurality of antibody heavy chain sequences into at least one heavy chain group, wherein said antibody heavy chain sequences in the heavy chain group are related in lineage;

d). grouping said obtained plurality of antibody light chain sequences into at least one light chain group, wherein said antibody light chain sequences in the light chain group are related in lineage;

e). selecting said heavy chain group and said light chain group;

f). pairing a heavy chain sequence from said heavy chain group and a light chain sequence from said light chain group; and g). testing a candidate antibody comprising the heavy and light chain sequences for binding to the antigen.

2. The method of embodiment 1, wherein the CDR3 regions of said antibody heavy chain sequences in the heavy chain group contain up to five amino acid differences relative to one another, and the CDR3 regions of said antibody light chain sequences in the light chain group contain up to five amino acid differences relative to one another.

3. The method of embodiment 1, wherein the antigen is a human antigen.

4. The method of embodiment 1, wherein the antibody heavy chain sequences are antibody heavy chain variable domain sequences and the antibody light chain sequences are antibody light chain variable domain sequences.

5. The method of embodiment 1, wherein the primate is an old world monkey, an orangutan, a gorilla or a chimpanzee.

6. The method of embodiment 1, wherein the primate is a crab-eating macaque, a rhesus macaque or a pig-tailed macaque.

7. The method of embodiment 1, wherein the CDR3 region of said antibody heavy chain sequences in the heavy chain group contain 0, 1 or 2 amino acid differences relative to one another; and wherein the CDR3 region of the antibody light chain sequences in the light chain group contain 0, 1 or 2 amino acid differences relative to one another.

8. The method of embodiment 1, wherein step b) is done by sequencing cDNAs encoding the heavy and light chain sequences from single B cells, or cultures of the same.

9. The method of embodiment 1, wherein step b) is done by sequencing cDNAs encoding the heavy and light chain sequences made from a plurality of B cells.

10. The method of embodiment 1, wherein the population of antibody-producing B cells are enriched by binding to the antigen.

11. The method of embodiment 1, wherein the heavy chain group and the light chain group both contain at least 2 members.

12. The method of embodiment 1, wherein the step g) comprises testing the candidate antibody in a blocking assay, a neutralization assay, an agonist assay or an antagonist assay.

13. The method of embodiment 1, wherein the step g) comprises testing the candidate antibody in an ELISA.

14. The method of embodiment 1, wherein the step b) comprises obtaining at least 100 different antibody heavy chain sequences and at least 100 different antibody light chain sequences.

15. The method of embodiment 1, wherein the antibody-producing B cells are obtained from bone marrow, spleen, lymph node or peripheral blood.

16. The method of embodiment 1, further comprising:

h) aligning the heavy chain sequence with a human heavy chain sequence, wherein said human heavy chain sequence is most homologous to the heavy chain sequence;

i) aligning the light chain sequence with a human light chain sequence, wherein said human light chain sequence is most homologous to the light chain sequence;

j) substituting at least one amino acid residues in the heavy chain or light chain sequence with the corresponding amino acid of the human heavy chain or human light chain sequence, thereby producing a humanized antibody.

17. A method for identifying a T-cell receptor (TCR) that binds to an antigen, comprising steps of:

a) obtaining a population of T cells from a primate that has been immunized by the antigen;

b) obtaining from the population of T cells
(i) a plurality of TCR α-chain sequences and
(ii) a plurality of TCR β-chain sequences;

c) grouping said obtained plurality of TCR α-chain sequences into at least one TCR α-chain group, wherein the TCR α-chain sequences in the TCR α-chain group are related in lineage;

d) grouping said obtained plurality of TCRβ-chain sequences into at least one TCR β-chain group, wherein the TCR β-chain sequences in the TCR β-chain group are related in lineage;

e) selecting the TCR α-chain group and the TCR β-chain group;

f) pairing a TCR α-chain sequence from the TCR α-chain group and a TCR β-chain sequence from the TCR β-chain group; and g) testing a candidate TCR comprising the TCR α-chain sequence and the TCR β-chain sequence for binding to the antigen.

18. The method of embodiment 17, wherein the CDR3 regions of said TCR α-chain sequences in the TCR α-chain group contain up to five amino acid differences relative to one another, and the CDR3 regions of said TCR β-chain sequence in the TCR β-chain group contain up to five amino acid differences relative to one another.

19. The method of embodiment 17, wherein the antigen is a human antigen.

20. The method of embodiment 17, wherein the TCR α-chain sequences are TCR α-chain variable domain sequences and the TCR β-chain sequences are TCR β-chain variable domain sequences.

21. The method of embodiment 17, wherein the primate is an old world monkey, an orangutan, a gorilla or a chimpanzee.

22. The method of embodiment 17, wherein the primate is a crab-eating macaque, a rhesus macaque or a pig-tailed macaque.

23. The method of embodiment 17, wherein the CDR3 regions of the TCR α-chain sequences in the TCR α-chain group are of the same length and contain 0, 1 or 2 amino acid substitutions relative to one another; and wherein the CDR3 regions of the TCR β-chain sequences in the TCR β-chain group are of the same length and contain 0, 1 or 2 amino acid substitutions relative to one another.

24. The method of embodiment 17, wherein step b) is done by sequencing cDNAs encoding the TCR α-chain and TCR β-chain sequences from single T cells, or cultures of the same.

25. The method of embodiment 17, wherein step b) is done by sequencing cDNAs encoding the TCR α-chain and TCR β-chain sequences made from a plurality of T cells.

26. The method of embodiment 17, wherein the T cells are enriched by binding to the antigen.

27. The method of embodiment 17, wherein the TCR α-chain group and the TCR β-chain group both contain at least 2 members.

28. The method of embodiment 17, wherein the step g) comprises testing the candidate TCR in a blocking assay, a neutralization assay an agonist assay or an antagonist assay.

29. The method of embodiment 17, wherein the step g) comprises testing the candidate TCR in an ELISA.

30. The method of embodiment 17, wherein step b) comprises obtaining at least 100 different TCR α-chain variable domain sequences and at least 100 different TCR β-chain variable domain sequences.

31. The method of embodiment 17, wherein the T cells are obtained from bone marrow, bone thymus, lymph node or peripheral blood.

32. The method for embodiment 17, further comprising:
   h) aligning the TCR α-chain sequence with a human TCR α-chain sequence, wherein said human TCR α-chain sequence is most homologous to said TCR α-chain sequence;
   i) aligning the TCR β-chain sequence with a human TCR β-chain sequence, wherein said human TCR β-chain sequence is most homologous to said TCR chain sequence; and
   j) substituting at least one amino acid residues in the human TCR α-chain sequence or human TCR β-chain sequence, thereby producing a humanized TCR.

The following examples are presented to illustrate the present invention. They are not intended to limiting in any manner.

EXAMPLE 1

The following is an example of identification of antibodies specifically block PD-1 and PD-LA binding.

Immunization and Collection of Monkey Blood

Two crab-eating macaques were immunized with injection of 1 mg antigen (recombinant human PD-L1 protein linked to mouse Fc fragment (hPD-L1-mFc) in complete Freund's adjuvant), and with boost of 1 mg antigen at day 20, 40 and 60. The PBMC was collected on day 0 (from 10 ml blood), 19 (from 10 ml blood), 39 (from 10 ml blood), 59 (from 12 ml blood) and 65 (from 12 ml blood).

PD-L1 Antibody Titer Detection

The immune response was detected by measuring the titer of antibodies against antigen by ELISA using the following protocol.

Coating: Dilute hPD-L1-mFc to 2 ug/ml in coating buffer (PBS). Coat plate with 50 ul/well. Incubate plate overnight at 4° C.

Blocking: Bring plate and assay diluent to RT. Wash plate 3 times with at least 250 ul/well washing buffer. Blot plate on paper to remove any residual buffer. Block wells with 200 ul/well of assay diluent (2% BSA in PBS). Incubate at RT for 2 hours.

Samples and Controls preparation: Dilute sample in 1:1000, 1:2000, 1:4000, 1:8000, 1:16000, 1:32000, 1:64000, 1:128000, 1:256000 with assay diluent. Wash plate 3 times with at least 250 ul/well washing buffer. Add 50 ul/well of prepared samples and controls in duplicate in the assay plate. Incubate assay plate at RT for 2 hrs.

Secondary Antibody: HRP Anti-Human IgG (BD, Cat #555788). Wash plate 3 times with at least 250 ul/well washing buffer. Dilute the secondary antibody in 1:2500 with assay diluent. Add 50 ul/well of the secondary antibody, and incubate at RT for 1 hr.

Substrate: Wash plate 5 times with at least 250 ul/well washing buffer. Allow about 1-2 min soaking time. Blot plate on paper to remove any residual buffer. Add 50 ul/well of TMB, and incubate at RT in dark for 5-10 min. Add 50 ul/well stop solution. Read plate at 450 nm.

Results: The results are show below. The titer of S05 is in the range of $1.2$-$1.5 \times 10^5$, and the titer of Z05 is in the range of $6$-$9 \times 10^4$.

| | S05-Day0 | S05-Day20 | S05-Day40 | S05-Day60 | S05-Day65 |
|---|---|---|---|---|---|
| 1:1000 | 0.08225 | 0.08895 | 0.14725 | 0.70155 | 1.0583 |
| 1:2000 | 0.07615 | 0.08325 | 0.1144 | 0.32855 | 0.7609 |
| 1:4000 | 0.07895 | 0.07915 | 0.09755 | 0.23645 | 0.4103 |
| 1:8000 | 0.0752 | 0.07495 | 0.10205 | 0.14995 | 0.29355 |
| 1:16000 | 0.07405 | 0.07655 | 0.0821 | 0.10755 | 0.1787 |
| 1:32000 | 0.08255 | 0.07165 | 0.08125 | 0.09185 | 0.1357 |
| 1:64000 | 0.0754 | 0.076 | 0.09355 | 0.07785 | 0.1054 |
| 1:128000 | 0.08915 | 0.077 | 0.07815 | 0.09 | 0.0897 |
| 1:256000 | 0.07515 | 0.0865 | 0.07825 | 0.0752 | 0.082 |

| | Z05-Day0 | Z05-Day20 | Z05-Day40 | Z05-Day60 | Z05-Day65 |
|---|---|---|---|---|---|
| 1:1000 | 0.06505 | 0.08035 | 0.13245 | 0.3553 | 0.42745 |
| 1:2000 | 0.0627 | 0.07985 | 0.12545 | 0.16825 | 0.2703 |
| 1:4000 | 0.06345 | 0.07525 | 0.0995 | 0.12795 | 0.17965 |
| 1:8000 | 0.06755 | 0.0758 | 0.08965 | 0.10705 | 0.1395 |
| 1:16000 | 0.06905 | 0.0755 | 0.0851 | 0.08945 | 0.09915 |
| 1:32000 | 0.0712 | 0.0719 | 0.0766 | 0.0832 | 0.0882 |
| 1:64000 | 0.07195 | 0.0721 | 0.0731 | 0.07535 | 0.08005 |
| 1:128000 | 0.086 | 0.0732 | 0.0746 | 0.0915 | 0.0856 |
| 1:256000 | 0.0715 | 0.07145 | 0.07235 | 0.07195 | 0.0772 |

PBMC Preparation and Storage

Prepare a PBMC suspension from whole peripheral blood by density gradient centrifugation (Sigma-HISTOPAQUE-1077, Cat #10771-6×100 ml) using the following protocol: Extract same volume of HISTOPAQUE-1077 into a new sterile tube. Carefully layer the diluted blood over HISTOPAQUE-1077. Make sure the interface is clear. Don't mix. Centrifuge at 1500 rpm (Radium of the horizontal rotor is 15 cm, appro. 400 g), RT for 30 min. Carefully aspirate the mononuclear layer (the second layer from the top) and transfer it into a new sterile centrifuge tube. Add an equal volume of PBS for washing. Wash 3× with 10 mL PBS. Spin down at 250×g (a speed sufficient to sediment the cells without damage), for 10 min PBMC Storage Condition-1: 10% DMSO+90% FBS, liquid nitrogen; PBMC Storage Condition-2: Resuspend the PBMC at $10 \times 10^6$ cells/ml in RNAPROTECT Cell Reagent (Qiagen; Cat #76526) (reagent providing immediate stabilization of RNA) and stored at −80 degree.

Total RNA Extraction

RNA was isolation with RNEASY Plus Mini Kit (Qiagen, Cat #:74134) using the following protocol: Pellet the appropriate number of cells (less than $1 \times 10^7$ cells) by centrifuging for 5 min at 300×g in a centrifuge tube. Disrupt the cells by adding 600 ul Buffer RLT Plus, and mix them by vortexing or pipetting. Transfer the homogenized lysates to a gDNA Eliminator spin column placed in a 2 ml collection tube. Centrifuge for 30 s at $\geq 8000 \times g$ ($\geq 210{,}000$ rpm). Discard the column, and save the flow-through. Add 600 ul of 70% ethanol to the flow-throughs, and mix well by pipetting.

Transfer up to 700 ul of the sample, including any precipitate, to an RNEASY spin column. Close the lid gently, and centrifuge for 15 s at ≥8000×g (≥10,000 rpm). Discard the flow-through. (If the sample volume exceeds 700 ul, centrifuge successive aliquots in the same RNEASY spin column) Add 700 ul Buffer RW1 to the RNEASY spin column. Close the lid gently, and centrifuge for 15 s at ≥8000×g (≥10,000 rpm). Discard the flow-through. Add 500 ul Buffer RPE to the RNEASY spin column. Close the lid gently, and centrifuge for 15 s at ≥8000×g rpm). Discard the flow-through. Add 500 ul Buffer RPE to the RNEASY spin column. Close the lid gently, and centrifuge for 2 min at ≥8000×g (≥10,000 rpm). Discard the flow-through. Place the RNEASY spin column in a new 1.5 ml collection tube. Add 50 ul Rnase-free water directly to the spin column membrane. Close the lid gently, and centrifuge for 1 min at ≥8000×g (≥10,000 rpm) to elute the RNA. Save them at −80° C.

Antibody Gene Amplification Using First Round PCR Primers List cDNA synthesis was performed with gene-specific primers (GSPs). (cDNA Synthesis Kit; invitrogen, Cat #18080-051). The GSPs used for PCR amplification of heavy chain variable region was as follows:

```
gamma-PCR1
                                  (SEQ ID NO: 85)
5'-GGACAGCCKGGAAGGTTGC-3'
(K = G or T)
```

The GSPs used for PCR amplification of light chain variable region was as follows:

```
kappa-PCR1
                                  (SEQ ID NO: 95)
5'GAGGCAGTTCCAGATTTCAA-3'
```

The first and second round PCR primer list came from WeiXu Meng's paper (mAbs: 2015. Vol. 7:707-718)

First Round PCR Primer List-VH Amplification

| Component | Amount |
|---|---|
| ExTaq (Takara, Cat#DRR001A) | 0.25 ul |
| 10 × Ex Taq Buffer | 5 ul |
| dNTP mix (10 mM) | 4 ul |
| VH cDNA | 2 ul |
| forward primers (10 uM) | 4 ul |
| gamma-PCR1 (10 uM) | 4 ul |
| ddH$_2$O | 30.75 ul |

PCR Reaction Condition:

| | | |
|---|---|---|
| 94° C. | 3 min | |
| 94° C. | 0.5 min | |
| 60° C. | 1 min | ] 35 cycles |
| 72° C. | 1 min | |
| 72° C. | 5 min | |
| 4° C. | forever | |

First Round PCR Primer List-Kappa V$_L$ Amplification

| Component | Amount |
|---|---|
| ExTaq (Takara, Cat#DRR001A) | 0.25 ul |
| 10 × Ex Taq Buffer | 5 ul |
| dNTP mix (10 mM) | 4 ul |
| KVL cDNA | 2 ul |
| forward primers (10 uM) | 4 ul |
| gamma-PCR1 (10 uM) | 4 ul |

PCR Reaction Condition:

| | | |
|---|---|---|
| 94° C. | 3 min | |
| 94° C. | 0.5 min | |
| 58° C. | 1 min | ] 35 cycles |
| 72° C. | 1 min | |
| 72° C. | 5 min | |
| 4° C. | forever | |

TABLE 1

First round PCR primer list

| | | SEQ ID NO | Primer name | Primer |
|---|---|---|---|---|
| 1st round heavy chain primer | 5' primer | 75 | LDRVH1A | 5'TCTSTCTCCACAGGCGCCCACTC |
| | | 76 | LDRVH1B | 5'TCCTCTMCRYAGGTGCCMASTC |
| | | 77 | LDRVH1C | 5'TCCTCTCCGCAGGGGCCCACTC |
| | | 78 | LDRVH2 | 5'GTCCCGTCCTGGGTCTTGTC |
| | | 79 | LDRVH3A | 5'CTATTTTARRAGGTGTCCAGTG |
| | | 80 | LDRVH3B | 5'CTCTTTTGAAAGGTGTCCAGTG |
| | | 81 | LDRVH3C | 5'CTATWYTAAAAGGTGTCCAGTC |
| | | 82 | LDRVH4 | 5'AGCTCCCAGATGGGTCYTGTCC |
| | | 83 | LDRVH5 | 5'TCTCCCCCACAGGAGTCTGTGC |
| | | 84 | LDRVH6 | 5'GGCCTCCCATGGGGTGTC |
| | 3' primer | 85 | gamma-PCR1 | 5'GGACAGCCKGGAAGGTGTGC |
| 1st round kappa chain primer | 5' primer | 86 | LDRVκ1 | 5'TCCAATYTCAGGTGCCARATGT |
| | | 87 | LDRVκ2 | 5'ATTTCAGGATCCAGTGGGGAT |
| | | 88 | LDRVκ3A | 5'TCCAATTTCAGATACCACYGGA |
| | | 89 | LDRVκ3B | 5'TCCAATCTCAGRTACCRCCGGA |
| | | 90 | LDRVκ4 | 5'TGGGTCTCGGTGCCCGTCAGG |
| | | 91 | LDRVκ5 | 5'TGGATCTCTGGTGCCTGTGGG |
| | | 92 | LDRVκ6 | 5'TGGATCTCTGATGCCAGGGCA |
| | | 93 | LDRVκ7 | 5'TGTGCTCCAGGCTGCAATGGG |
| | 3' primer | 94 | kappa-PCR1 | 5'GAGGCAGTTCCAGATTTCAA |

Result of Heavy Chain Variable Region Gene Amplification with First Round PCR Primer Set Using the cDNA from the PBMC of cyno S05 as the template, we amplified the genes encoding the variable region of the heavy chain. After running agarose gel, the PCR products with desired size were cut, purified and cloned into pMD19-T (Takara; Cat #6013) for sequencing, we found the PCR product containing lots of non-specific bands when using LDRVH1A, LDRVH1B and LDRVH1C (see the Table1 and Table2) as 5' primers.

TABLE 2

| S05-VH | 1stPCR | Sequencing |
| --- | --- | --- |
| LDR H1A | Lots of non-specific bands, need to optimize PCR condition | N\A |
| LDR H1B | Lots of non-specific bands, need to optimize PCR condition | N\A |
| LDR H1C | Lots of non-specific bands, need to optimize PCR condition | N\A |
| LDR H2 | Target band (500-600 bp in size) was cut from Agarose gel, inserted to TA vector and transformed to *E. coli*. 10 single clones were pick up for DNA sequencing | Four out of 9 are consistant with antibody sequence |
| LDR H3A | Target band (500-600 bp in size) was cut from Agarose gel, inserted to TA vector and transformed to *E. coli*. 10 single clones were pick up for DNA sequencing | Seven out of 9 are consistant with antibody sequence |
| LDR H3B | Target band (500-600 bp in size) was cut from Agarose gel, inserted to TA vector and transformed to *E. coli*. 10 single clones were pick up for DNA sequencing | Nine out of 9 are consistant with antibody sequence |
| LDR H3C | Target band (500-600 bp in size) was cut from Agarose gel, inserted to TA vector and transformed to *E. coli*. 10 single clones were pick up for DNA sequencing | Six out of 9 are consistant with antibody sequence |
| LDR H4 | Target band (500-600 bp in size) was cut from Agarose gel, inserted to TA vector and transformed to *E. coli*. 10 single clones were pick up for DNA sequencing | Eight out of 9 are consistant with antibody sequence |
| LDR H5 | Target band (500-600 bp in size) was cut from Agarose gel, inserted to TA vector and transformed to *E. coli*. 10 single clones were pick up for DNA sequencing | One out of 10 are consistant with antibody sequence |
| LDR H6 | Target band (500-600 bp in size) was cut from Agarose gel, inserted to TA vector and transformed to *E. coli*. 10 single clones were pick up for DNA sequencing | Two out of 10 are consistant with antibody sequence |

The alignment results of heavy chairs variable region are shown in FIG. 5A-5C.

Result of Light Chain Variable Region Gene Amplification with First Round PCR Primer Set Using the cDNA from the PBMC of cyno S05 as the template, we tried to amplify the genes encoding the variable region of the light chain. After running agarose gel, the PCR products with desired size were cut, purified and cloned into pMD19-T (Takara; Cat #6013) for sequencing, we found the PCR product containing lots of non-specific bands when using LDRVk2, LDRVk5 and LDRVk6 (see the table1 and table4) as 5' primers.

TABLE 3

| S05-KVL | 1stPCR | Sequencing |
| --- | --- | --- |
| LDR L1 | Target band (400-500 bp in size) was cut from Agarose gel, inserted to TA vector and transformed to *E. coli*. 10 single clones were pick up for DNA sequencing | Nine out of 10 are consistant with antibody sequence |
| LDR L2 | N\A | N\A |
| LDR L3A | Target band (400-500 bp in size) was cut from Agarose gel, inserted to TA vector and transformed to *E. coli*. 10 single clones were pick up for DNA sequencing | Seven out of 10 are consistant with antibody sequence |
| LDR L3B | Target band (400-500 bp in size) was cut from Agarose gel, inserted to TA vector and transformed to *E. coli*. 10 single clones were pick up for DNA sequencing | Nine out of 10 are consistant with antibody sequence |
| LDR L4 | Target band (400-500 bp in size) was cut from Agarose gel, inserted to TA vector and transformed to *E. coli*. 10 single clones were pick up for DNA sequencing | None out of 10 are consistant with antibody sequence |
| LDR L5 | N\A | N\A |
| LDR L6 | N\A | N\A |
| LDR L7 | Target band (400-500 bp in size) was cut from Agarose gel, inserted to TA vector and transformed to *E. coli*. 10 single clones were pick up for DNA sequencing | None out of 10 are consistant with antibody sequence |

The alignment results of light chain variable region are shown in FIG. 6.

Antibody Gene Amplification Using Second Round PCR Primer List

TABLE 4

Second round PCR primer list

| | | SEQ ID NO | Primer name | Primer |
|---|---|---|---|---|
| 2nd round heavy chain primer | 5' primer | 95 | FRVH1A IF5 | 5'ACAGGTGTCCACTCGGACCTCCAGTGGTRCAGTC |
| | | 96 | FRVH1B IF5 | 5'ACAGGTGTCCACTCGCAGGWGCAGCTGGTGCAGTC |
| | | 97 | FRVH2 IF5 | 5'ACAGGTGTCCACTCGCAGGTGACCTTGAAGGAGTCTG |
| | | 98 | FRVH3 IF5 | 5'ACAGGTGTCCACTCGGARGRGCAGYTGGTGGAGTCTG |
| | | 99 | FRVH4A IF5 | 5'ACAGGTGTCCACTCGCAGSTGCAGCTGCAGGAGTCGG |
| | | 100 | FRVH4B IF5 | 5'ACAGGTGTCCACTCGCAGCTGCAGCTGCAGCTGCAGG |
| | | 101 | FRVH5 IF5 | 5'ACAGGTGTCCACTCGGAGGTGCAGCTGGTGCAGTCTG |
| | | 102 | FRVH6 IF5 | 5'ACAGGTGTCCACTCGCAGGTGCAGCTGCAGGAGTCAG |
| | 3' primer | 103 | FRVH1 IF3 | 5'GATGGGCCCTTGGTGGATGCTGAGGAGACGGTGACCAGGGC |
| | | 104 | FRVH2 IF3 | 5'GATGGGCCCTTGGTGGATGCTGAGGAGATGGTGATTGGGGT |
| | | 105 | FRVH3 IF3 | 5'GATGGGCCCTTGGTGGATGCTGAAGAGACGGTGACCCTGAG |
| | | 106 | FRVH4/5 IF3 | 5'GATGGGCCCTTGGTGGATGCTGAGGAGACGGTGACCAGGAC |
| | | 107 | FRVH6 IF3 | 5'GATGGGCCCTTGGTGGATGCTGAGGAGACGGTGACCAGAAC |
| | | 108 | FRVH7 IF3 | 5'GATGGGCCCTTGGTGGATGCTGAGGAGACGGTGACGACGA |
| 2nd round kappa chain primer | 5' primer | 109 | FRVκ1 IF5 | 5'CTTACAGACGCTCGCTGCGACATYCAGATGWCCCAGTCTC |
| | | 110 | FRVκ2A IF5 | 5'CTTACAGACGCTCGCTGCGATAYTGTGATGAYCCAGACTC |
| | | 111 | FRVκ2B IF5 | 5'CTTACAGACGCTCGCTGCGATGTTGYRATGACTCAGTCTC |
| | | 112 | FRVκ3A IF5 | 5'CTTACAGACGCTCGCTGCGAAATWGTRATGACGCAGTCTC |
| | | 113 | FRVκ3B IF5 | 5'CTTACAGACGCTCGCTGCCAAGTTATATTGACTCAGTCTC |
| | | 114 | FRVκ4 IF5 | 5'CTTACAGACGCTCGCTGCCTGGATCTCTGGTGTCTGTGG |
| | | 115 | FRVκ5 IF5 | 5'CTTACAGACGCTCGCTGCCCTTTGGATCTCTGMTGCCAGG |
| | | 116 | FRVκ6 IF5 | 5'CTTACAGACGCTCGCTGCTGGGTTCCAGTCTCCAAGGG |
| | | 117 | FRVκ7 IF5 | 5'CTTACAGACGCTCGCTGCTGTGCTCCAGGCTGCAATGG |
| | 3' primer | 118 | FRVκ1 IF3 | 5'ATGGTGCAGCCACCGTACGTTTGATCTCCAGCTT |
| | | 119 | FRVκ2 IF3 | 5'ATGGTGCAGCCACCGTACGTTTGATTTCCACCTT |
| | | 120 | FRVκ3 IF3 | 5'ATGGTGCAGCCACCGTACGTTTGATCTCCACTTT |
| | | 121 | FRVκ4 IF3 | 5'ATGGTGCAGCCACCGTACGTTTGATATCCAGTTT |
| | | 122 | FRVκ5 IF3 | 5'ATGGTGCAGCCACCGTACGTTTAATCTCCAGTCG |

Second Round PCR Primer List-VH1 Amplification

| Component | Amount |
|---|---|
| ExTaq (Takara, Cat#DRR001A) | 0.25 ul |
| 10 × Ex Taq Buffer | 5 ul |
| dNTP mix (10 mM) | 4 ul |
| VH cDNA | 2 ul |
| forward primers (10 uM) | 4 ul |
| FRVH1 1F3 (10 uM) | 4 ul |
| ddH$_2$O | 30.75 ul |

PCR Reaction Condition:

| 94° C. | 3 min | |
|---|---|---|
| 94° C. | 0.5 min | |
| 61° C. | 1 min | ] 35 cycles |
| 72° C. | 1 min | |
| 72° C. | 5 min | |
| 4° C. | forever | |

Second Round PCR Primer List-Kappa VL2 Amplification

| Component | Amount |
|---|---|
| ExTaq (Takara, Cat#DRR001A) | 0.25 ul |
| 10 × Ex Taq Buffer | 5 ul |
| dNTP mix (10 mM) | 4 ul |
| KVL cDNA | 2 ul |
| forward primers (10 uM) | 4 ul |
| FRVk2 1F3 (10uM) | 4 ul |

PCR reaction condition:

| 94° C. | 3 min | |
|---|---|---|
| 94° C. | 0.5 min | |
| 59° C. | 1 min | ] 35 cycles |
| 72° C. | 1 min | |
| 72° C. | 5 min | |
| 4° C. | forever | |

Result of Heavy Chain Variable Region Gene Amplification with Second Round PCR Primer Set As we were unable to amplify the DNA encoding the variable region of heavy chain by primer RhLDRVH1A, RhLDRVH1B and RhLDRVH1C, we then tried the primer FRVH1 (a mixture of primer Rh FRVH1A IF5 and Rh FRVH1B IF5 at 1:1 ratio, see the Table4 and Table5). We found that the antibody genes could be amplified efficiently with nice sequence diversity by the primers.

TABLE 5

| S05-VH | 2ndPCR | Sequencing |
| --- | --- | --- |
| FRV H1 | Target band (350-450 bp in size) was cut from Agarose gel, inserted to TA vector and transformed to E. coli. 12 single clones were pick up for DNA sequencing | Eleven out of 12 are consistant with antibody sequence(two of them are the same AA sequences) |

The alignment results of heavy chain variable region from the second round PCR are shown in FIG. 7.

Result of Light Chain Variable Region Gene Amplification with Second Round PCR Primer Set As we were unable to amplify the DNA encoding the variable region of light chain by primer LDRVk2, LDRVk5 and LDRVk6, we then tried the primer FRVk L2 (a mixture of primer LDRVk2A IF5 and LDRVk2B IF5 at 1:1 ratio, see the Table 4 and Table 6). We found that the antibody genes could be amplified efficiently with nice sequence diversity by the primer.

TABLE 6

| S05-KVL | 2ndPCR | Sequencing |
| --- | --- | --- |
| FRVk L2 | Target band (300-400 bp in size) was cut from Agarose gel, inserted to TA vector and transformed to E. coli. 6 single clones were pick up for DNA sequencing | Five out of six are consistant with antibody sequence(two of them AA sequence are psudogene) |

The alignment results of light chain variable region from the second round PCR are shown in FIG. 8.

Phylogenetic Analysis

Figure 9:
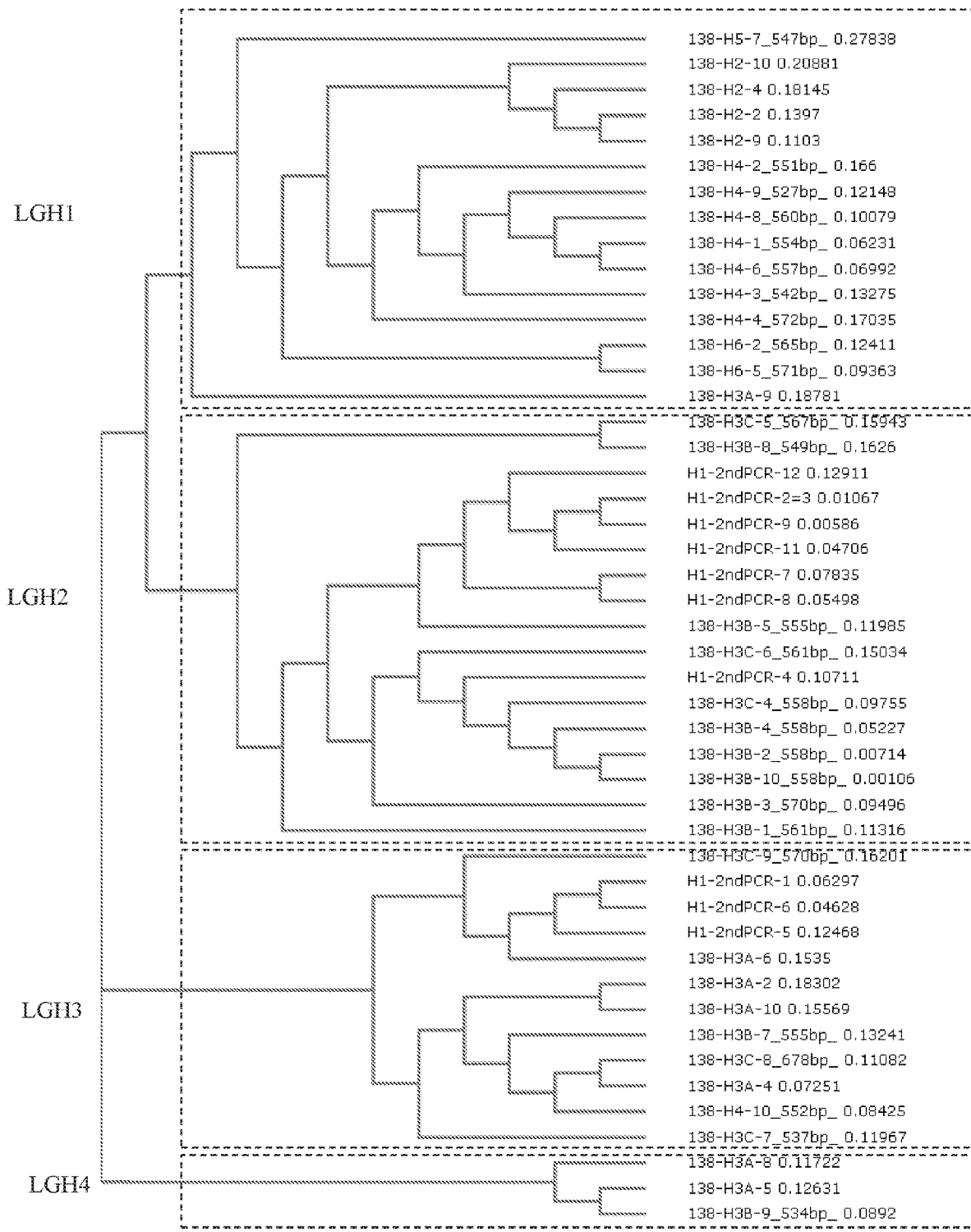
FIG. 9 shows the phylogenic tree of the sequences of the heavy chain variable region sequences generated in a monkey immunized with PD-L1.
Figure 10:
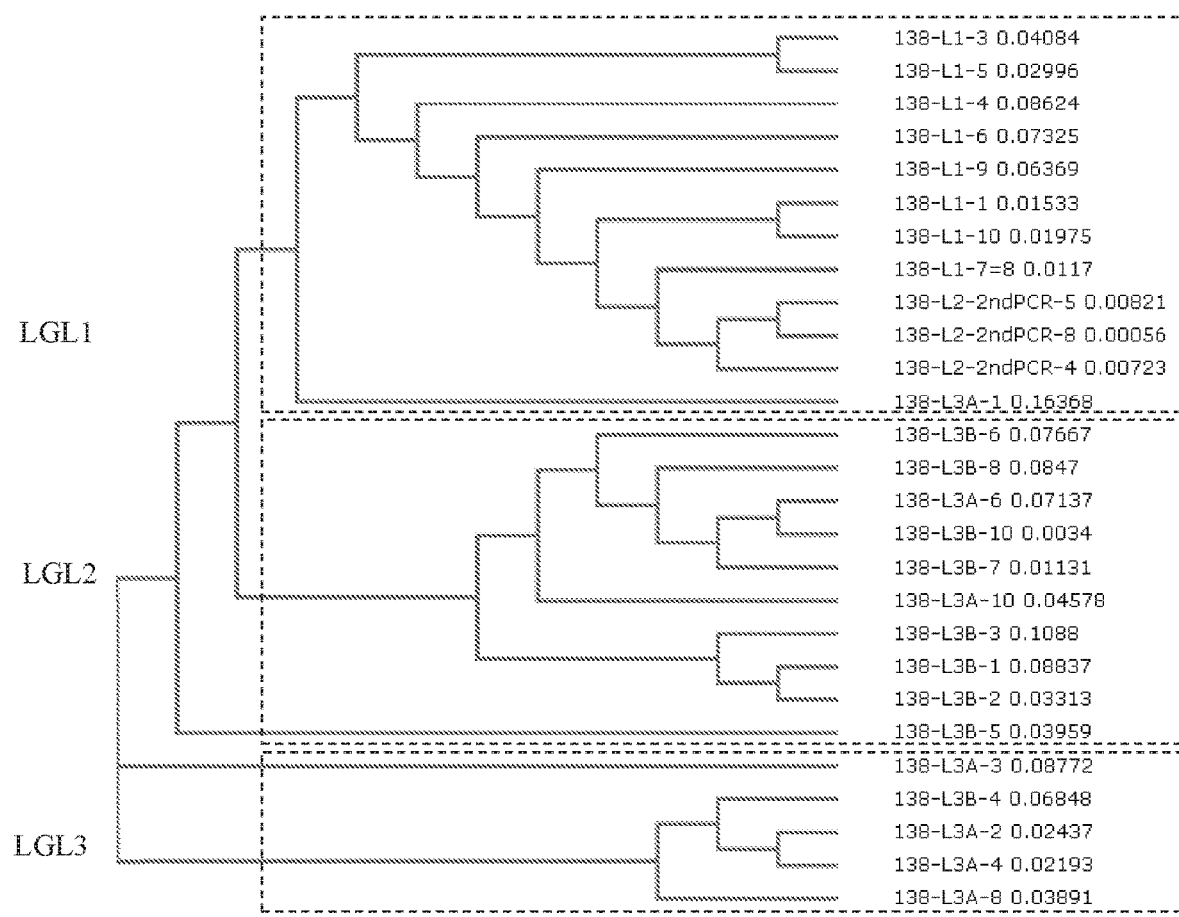
FIG. 10 shows the phylogenic tree of the sequences of the light chain variable region sequences generated in a monkey immunized with PD-L1.

FIGS. 9 and 10 show the phylogenetic tree of the sequences of heavy chain and light chain variable region. The heavy chain variable region can be grouped into at least four lineages while the light chain variable region can be grouped into at least three lineages.

Identification of Antibodies with Blocking Activity

One heavy chain variable region gene from each lineage group (LGH1, LGH2, LGH3, LGH4) is paired with one light chain variable region genes from each lineage group (LGL1, LGL2, and LGL3) to generate the candidate antibody genes. The candidate antibody genes are expressed in in 24-well and are tested for their binding activity against the antigen. Antibodies binding to the antigen are tested for their activity in blocking PD-1 and PD-L1 binding interaction by FACS. Antibodies having blocking activity in FACS assay are then detected for their blocking activity in mixed lymphocyte reaction assay.

EXAMPLE 2

The following is an example of identification of T-cell receptors (TCR) specifically block PD-1 and PD-L1 binding.

Briefly, two crab-eating macaques are immunized with injection of 1 mg antigen (human PD-L1 protein), and with boost of 1 mg antigen at day 20, 40 and 60. The immune response is detected by measuring the titer of antibodies against antigen at day 45 and 65 by ELISA. The PBMC is then collected on day 0, 19, 39, 59 and 69, from which T cells are enriched with PD-L1 binding capability by sorting FACS or magnetic beads. Total RNA from the T cells is then isolated, from which cDNA is prepared. The TCR α-chain and β-chain variable region genes are cloned by PCR, which are subject to deep sequencing to determine the variable region gene sequences. The variable region gene sequences are grouped into different lineages according to their length and variations in CDR3. TCR α-chain variable region genes are then paired with β-chain variable region genes to generate the candidate TCR genes, wherein only one α-chain/β-chain variable region gene is selected from each candidate group. The candidate TCR genes are expressed in small scale (in 24-well or 6-well plates) and are tested for their binding activity against the antigen. TCRs binding to the antigen are tested for their activity in blocking PD-1 and PD-L1 binding interaction by FACS. TCRs having blocking activity in FACS assay are then detected for their blocking activity in mixed lymphocyte reaction assay.

The previous description provides exemplary embodiments only, and is not intended to limit the scope, applicability, or configuration of the disclosure. Rather, the previous description of the exemplary embodiments will provide those skilled in the art with an enabling description for implementing one or more exemplary embodiments. It is understood that various changes may be made in the function and arrangement of elements without departing from the spirit and scope of the invention. Several embodiments were described herein, and while various features are ascribed to different embodiments, it should be appreciated that the features described with respect to one embodiment may be incorporated within other embodiments as well. By the same token, however, no single feature or features of any described embodiment should be considered essential to every embodiment of the invention, as other embodiments of the invention may omit such features.

Specific details are given in the previous description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have also included additional steps or operations not discussed or included in a figure.

Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

While detailed descriptions of one or more embodiments have been give above, various alternatives, modifications, and equivalents will be apparent to those skilled in the art without varying from the spirit of the invention. Moreover, except where clearly inappropriate or otherwise expressly noted, it should be assumed that the features, devices, and/or components of different embodiments may be substituted and/or combined. Thus, the above description should not be taken as limiting the scope of the invention. Lastly, one or more elements of one or more embodiments may be combined with one or more elements of one or more other embodiments without departing from the scope of the invention.

What is claimed is:

1. A method comprising the steps of:
   a) obtaining a population of T cells from a non-human primate that has been immunized by an antigen, wherein the T cells are enriched by binding to the antigen;
   b) preparing cDNA from the population of T cells without separating the population of T cells into single cells;
   c) sequencing the cDNA to obtain:
      (c1) a plurality of T-cell receptor (TCR) α-chain sequences and
      (c2) a plurality of TCR β-chain sequences,
      wherein each of the TCR α-chain sequences comprises an α-chain framework, CDR-α1, CDR-α2 and CDR-α3, and wherein each of the TCR β-chain sequences comprises a β-chain framework, CDR-β1, CDR-β2 and CDR-β3;
   d) grouping said obtained plurality of TCR α-chain sequences into a plurality of α-chain groups, wherein the CDR-α3 of said α-chain sequences in each α-chain group contain 0, 1 or 2 amino acid differences relative to one another;
   e) grouping said obtained plurality of TCR β-chain sequences into a plurality of β-chain groups, wherein the CDR-β3 of said β-chain sequences in each β-chain group contain 0, 1 or 2 amino acid differences relative to one another;
   f) ranking the plurality of α-chain groups according to the number of TCR α-chain sequences in each α-chain group, wherein
      a first α-chain group has the most members of TCR α-chain sequences and a second α-chain group has the second most members of TCR α-chain sequences, and so on for the plurality of α-chain groups;
   g) ranking the plurality of β-chain groups according to the number of TCR β-chain sequences in each β-chain group, wherein
      a first β-chain group has the most members of TCR β-chain sequences and a second β-chain group has the second most members of TCR β-chain sequences, and so on for the plurality of β-chain groups;
   h) pairing the first α-chain group with the first β-chain group;
   i) pairing a first TCR α-chain sequence from the first α-chain group and a first TCR β-chain sequence from the first β-chain group, wherein
the first TCR α-chain sequence comprises an α-chain framework, CDR-α1, CDR-α2 and CDR-α3, and
the first TCR β-chain sequence comprises a β-chain framework, CDR-β1, CDR-β2 and CDR-β3; and
j) testing a first candidate TCR comprising the first TCR α-chain sequence from the first α-chain group and the first TCR β-chain sequence from the first β-chain group for binding to the antigen bound to a major histocompatibility complex (MHC) molecule.

2. The method of claim 1, wherein the antigen is a human antigen.

3. The method of claim 1, wherein the non-human primate is an old-world monkey, an orangutan, a gorilla or a chimpanzee.

4. The method of claim 1, wherein the non-human primate is a crab-eating macaque, a rhesus macaque or a pig-tailed macaque.

5. The method of claim 1, wherein the α-chain groups and the β-chain groups contain at least 2 members.

6. The method of claim 1, wherein the step j) comprises testing the candidate TCR in an agonist assay.

7. The method of claim 1, wherein the plurality of TCR α-chain sequences comprises at least 100 different TCR α-chain sequences and the plurality of TCR β-chain sequences comprises at least 100 different TCR β-chain sequences.

8. The method of claim 1, wherein the T cells are obtained from bone marrow, thymus, lymph node or peripheral blood.

9. The method of claim 1, further comprising:
k) aligning the first TCR α-chain sequence with a human TCR α-chain sequence comprising a human α-chain framework, wherein the human α-chain framework is at least 90% identical to the first α-chain framework of the first TCR α-chain sequence;
l) aligning the first TCR β-chain sequence with a human TCR β-chain sequence comprising a human β-chain framework, wherein the human β-chain framework is at least 90% identical to the first β-chain framework of the first TCR β-chain sequence; and
m) substituting at least one amino acid residue in the first TCR α-chain sequence with the corresponding amino acid of the human TCR α-chain sequence or at least one amino acid residue in the first TCR β-chain sequence with the corresponding amino acid of the human TCR β-chain sequence, thereby producing a humanized TCR.

10. The method of claim 5, further comprising:
n) pairing a second TCR α-chain sequence from the first α-chain group and a second TCR β-chain sequence from the first β-chain group,
wherein
the second TCR α-chain sequence comprises an α-chain framework, a CDR-α1, a CDR-α2 and a CDR-α3, and
the second TCR β-chain sequence comprises a β-chain framework, a CDR-β1, a CDR-β2 and a CDR-β3; and
o) testing a second TCR comprising the second TCR α-chain sequence from the first α-chain group and the second TCR β-chain sequence from the first β-chain group for binding to the antigen bound to the MHC molecule.

11. The method of claim 1, wherein in step c) the cDNA is sequenced using high throughput sequencing technology.

12. The method of claim 1, further comprising
pairing the second α-chain group with the second β-chain group;
pairing a TCR α-chain sequence from the second α-chain group and a TCR β-chain sequence from the second β-chain group, wherein
the TCR α-chain sequence from the second α-chain group comprises an α-chain framework, a CDR-α1, a CDR-α2 and a CDR-α3, and the TCR β-chain sequence from the second β-chain group comprises a β-chain framework, a CDR-β1, a CDR-β2 and a CDR-β3; and
testing a second candidate TCR comprising the TCR α-chain sequence from the second α-chain group and the TCR β-chain sequence from the second β-chain group for binding to the antigen bound to the MHC molecule.

* * * * *

SEQUENCE LISTING

```
<160> NUMBER OF SEQ ID NOS: 122

<210> SEQ ID NO 1
<211> LENGTH: 118
<212> TYPE: PRT
<213> ORGANISM: Artificial Sequence
<220> FEATURE:
<223> OTHER INFORMATION: Synthetic

<400> SEQUENCE: 1

Ser Leu Gln Leu Val Gln Ser Gly Ala Glu Val Lys Arg Pro Gly Glu
1               5                   10                  15

Ser Leu Lys Ile Ser Cys Lys Thr Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ala Ile Asp Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Thr Tyr Tyr Cys
                85                  90                  95

Ala Lys Asp Arg Tyr Gly Thr Tyr Phe Tyr Tyr Trp Gly Gln Gly Val
            100                 105                 110

Leu Val Thr Val Ser Ser
        115

<210> SEQ ID NO 2
<211> LENGTH: 125
<212> TYPE: PRT
<213> ORGANISM: Artificial Sequence
<220> FEATURE:
<223> OTHER INFORMATION: Synthetic

<400> SEQUENCE: 2

Glu Val Gln Leu Ala Glu Ser Gly Gly Gly Leu Val Gln Pro Gly Gly
1               5                   10                  15

Ser Leu Arg Leu Ser Cys Ala Ala Ser Gly Phe Ile Phe Asp Asp Tyr
            20                  25                  30

Ala Met Ser Trp Val Arg Gln Ala Pro Gly Lys Gly Leu Glu Trp Val
        35                  40                  45

Ser Arg Val Thr Trp Asn Ser Tyr Thr Thr Ser Tyr Ala Asp Ser Val
    50                  55                  60

Lys Gly Arg Phe Thr Ile Ser Arg Glu Asn Ala Ala Asn Ser Leu Tyr
65                  70                  75                  80

Leu Gln Met Asn Arg Leu Asn Pro Glu Asp Thr Gly Leu Tyr Tyr Cys
                85                  90                  95

Ala Arg Asp Gly Asp Glu His Cys Thr Gly Ile Gly Cys Tyr Leu Ile
            100                 105                 110

Asp Ser Trp Gly Gln Gly Val Leu Val Thr Val Ser Ser
```

<210> SEQ ID NO 3
<211> LENGTH: 121
<212> TYPE: PRT
<213> ORGANISM: Artificial Sequence
<220> FEATURE:
<223> OTHER INFORMATION: Synthetic

<400> SEQUENCE: 3

Glu Val His Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Met Ser Trp Ile Arg Gln Ala Pro Gly Lys Gly Leu Glu Trp Val
        35                  40                  45

Ala Arg Ile Lys Arg Glu Ala Asp Gly Gly Thr Ala Asp Tyr Ala Ala
    50                  55                  60

Thr Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Arg Gly Thr Gly Thr Thr Ile Leu Tyr Trp Gly
            100                 105                 110

Gln Gly Val Leu Val Thr Val Ser Ser
        115                 120

<210> SEQ ID NO 4
<211> LENGTH: 123
<212> TYPE: PRT
<213> ORGANISM: Artificial Sequence
<220> FEATURE:
<223> OTHER INFORMATION: Synthetic

<400> SEQUENCE: 4

Glu Val Arg Leu Val Glu Ser Gly Gly Gly Leu Val Gln Pro Gly Gly
1               5                   10                  15

Ser Leu Arg Leu Ser Cys Ala Ala Ser Gly Phe Asn Phe Ser Asp Tyr
            20                  25                  30

Tyr Ile Tyr Trp Val Arg Gln Ala Pro Gly Met Gly Leu Glu Trp Val
        35                  40                  45

Gly Phe Val Arg Lys Pro Ala Tyr Gly Gly Thr Ser Glu Tyr Ala Ala
    50                  55                  60

Ser Val Lys Gly Arg Phe Ile Leu Ser Arg Asp Asp Ser Lys Asp Val
65                  70                  75                  80

Ala Tyr Leu Gln Met Gly Ser Leu Lys Ile Glu Asp Thr Ala Val Tyr
                85                  90                  95

Tyr Cys Ser Met Ala Tyr Ser Ser Ala Trp Asp Ile Ser Phe Glu Phe
            100                 105                 110

Trp Gly Gln Gly Ala Leu Val Thr Val Ser Ser
        115                 120

<210> SEQ ID NO 5
<211> LENGTH: 123
<212> TYPE: PRT
<213> ORGANISM: Artificial Sequence
<220> FEATURE:
<223> OTHER INFORMATION: Synthetic

<400> SEQUENCE: 5

```
Glu Val Gln Leu Val Glu Ser Gly Gly Ala Leu Ala Gln Pro Gly Gly
1               5                   10                  15

Ser Leu Arg Leu Ser Cys Ala Ala Ser Gly Phe Thr Phe Thr Asp Tyr
            20                  25                  30

Tyr Met Asp Trp Val Arg Gln Ala Pro Gly Lys Gly Leu Glu Trp Val
        35                  40                  45

Ser Arg Ile Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Gln Thr Glu Asp Thr Ala Val Tyr
                85                  90                  95

Tyr Cys Ala Arg Thr Ala Ala Tyr Ser Gly Lys His Phe Ser Asp Tyr
                100                 105                 110

Trp Gly Gln Gly Val Leu Val Thr Val Ser Ser
            115                 120
```

```
<210> SEQ ID NO 6
<211> LENGTH: 126
<212> TYPE: PRT
<213> ORGANISM: Artificial Sequence
<220> FEATURE:
<223> OTHER INFORMATION: Synthetic

<400> SEQUENCE: 6

Glu Val Arg Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Val Asn Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Ser Leu Gln Met Asn Ser Leu Lys Thr Glu Asp Thr Ala Val Tyr
                85                  90                  95

Tyr Cys Thr Arg Gly Gly Ile Ala Val Val Ser Pro Thr Pro Tyr
                100                 105                 110

Phe Tyr Tyr Trp Gly Gln Gly Ala Leu Val Thr Val Ser Ser
            115                 120                 125
```

```
<210> SEQ ID NO 7
<211> LENGTH: 122
<212> TYPE: PRT
<213> ORGANISM: Artificial Sequence
<220> FEATURE:
<223> OTHER INFORMATION: Synthetic

<400> SEQUENCE: 7

Glu Val Gln Leu Ile Asp Ser Gly Gly Gly Leu Val Gln Pro Gly Gly
1               5                   10                  15

Ser Leu Arg Leu Ser Cys Ala Ala Ser Gly Phe Arg Leu Thr Asp Tyr
            20                  25                  30

Ala Ile Tyr Trp Val Arg Gln Ala Pro Gly Lys Gly Leu Glu Trp Leu
        35                  40                  45

Gly Phe Ile Arg Ser Lys Ala Tyr Asp Gly Thr Ala Glu Tyr Ala Ala
```

```
                    50                  55                  60
Ser Val Lys Gly Arg Phe Thr Phe Ser Arg Asp Asp Ser Lys Asp Thr
 65                  70                  75                  80

Ala Phe Leu Gln Met Ser Ser Leu Lys Thr Glu Asp Ser Ala Val Tyr
                     85                  90                  95

Tyr Cys Thr Arg Gly Asn Trp Asn Tyr Val Asp Trp Phe Asp Val Trp
                    100                 105                 110

Gly Pro Gly Val Leu Val Thr Val Ser Ser
            115                 120

<210> SEQ ID NO 8
<211> LENGTH: 122
<212> TYPE: PRT
<213> ORGANISM: Artificial Sequence
<220> FEATURE:
<223> OTHER INFORMATION: Synthetic

<400> SEQUENCE: 8

Glu Val Arg Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Tyr Met Ser Trp Val Arg Gln Ala Pro Gly Lys Gly Leu Glu Trp Val
             35                  40                  45

Gly Phe Ile Arg Asn Lys Ala Asn Gly Gly Thr Ala Glu Tyr Ala Ala
         50                  55                  60

Ser Val Lys Gly Arg Phe Ala Ile Ser Arg Asp Asp Ser Lys Asn Thr
 65                  70                  75                  80

Thr Tyr Leu Gln Leu Ser Ser Leu Lys Thr Glu Asp Ser Ala Val Tyr
                     85                  90                  95

Phe Cys Thr Arg Gly Asn Trp Asn Tyr Val Asn Trp Phe Asp Val Trp
                    100                 105                 110

Gly Pro Gly Val Met Val Thr Val Ser Ser
            115                 120

<210> SEQ ID NO 9
<211> LENGTH: 122
<212> TYPE: PRT
<213> ORGANISM: Artificial Sequence
<220> FEATURE:
<223> OTHER INFORMATION: Synthetic

<400> SEQUENCE: 9

Glu Val His Leu Val Glu Ser Gly Gly Asp Leu Val His Pro Gly Gly
  1               5                  10                  15

Ser Leu Arg Leu Ser Cys Ala Ala Ser Gly Phe Pro Phe Ser Asp Tyr
                 20                  25                  30

Thr Ile Tyr Trp Val Arg Gln Ala Pro Arg Lys Gly Leu Glu Trp Val
             35                  40                  45

Gly Phe Ile Arg Thr Lys Ala Phe Asp Gly Thr Ala Asp Tyr Ala Ala
         50                  55                  60

Ser Val Lys Gly Arg Phe Thr Leu Ser Arg Asp Asp Ser Lys Asn Thr
 65                  70                  75                  80

Ala Tyr Leu Gln Leu Ser Ser Leu Lys Thr Glu Asp Ser Ala Val Tyr
                     85                  90                  95

Phe Cys Thr Arg Ala Asn Trp Asn Tyr Val Asn Trp Phe Asp Val Trp
                    100                 105                 110
```

```
Gly Pro Gly Val Leu Val Thr Val Ser Ser
        115                 120
```

<210> SEQ ID NO 10
<211> LENGTH: 122
<212> TYPE: PRT
<213> ORGANISM: Artificial Sequence
<220> FEATURE:
<223> OTHER INFORMATION: Synthetic

<400> SEQUENCE: 10

```
Glu Val His Leu Val Glu Ser Gly Gly Asp Leu Val His Pro Gly Gly
1               5                   10                  15

Ser Leu Arg Leu Ser Cys Ala Ala Ser Gly Phe Pro Phe Ser Asp Tyr
            20                  25                  30

Thr Ile Tyr Trp Val Arg Gln Ala Pro Arg Lys Gly Leu Glu Trp Val
        35                  40                  45

Gly Phe Ile Arg Thr Lys Ala Phe Asp Gly Thr Ala Asp Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Leu Ser Ser Leu Lys Thr Glu Asp Ser Ala Val Tyr
                85                  90                  95

Phe Cys Thr Arg Ala Asn Trp Asn Tyr Val Asn Trp Phe Asp Val Trp
            100                 105                 110

Gly Pro Gly Val Leu Val Thr Val Ser Ser
        115                 120
```

<210> SEQ ID NO 11
<211> LENGTH: 123
<212> TYPE: PRT
<213> ORGANISM: Artificial Sequence
<220> FEATURE:
<223> OTHER INFORMATION: Synthetic

<400> SEQUENCE: 11

```
Glu Val Gln Leu Val Glu Ser Gly Gly Gly Leu Val Trp Pro Gly Gly
1               5                   10                  15

Ser Leu Thr Leu Ser Cys Ala Ala Ser Gly Phe Ile Phe Ser Asp Tyr
            20                  25                  30

Gly Phe Asn Trp Val Arg Gln Ala Pro Gly Lys Gly Leu Glu Trp Ile
        35                  40                  45

Ser Tyr Ile Ser Pro Tyr Ser Ser Phe Ile Tyr Tyr Ser Asp Ser Val
    50                  55                  60

Lys Gly Arg Phe Thr Ile Ser Arg Asp Ser Ala Thr Asp Ser Val Ser
65                  70                  75                  80

Leu Leu Met Asp Gly Leu Arg Pro Asp Asp Thr Ala Val Tyr Tyr Cys
                85                  90                  95

Ala Lys Ser Arg Leu Ser Trp Asn Asp Gly Arg Tyr Gly Leu Asp Ser
            100                 105                 110

Trp Gly Gln Gly Ala Val Val Thr Val Ser Ser
        115                 120
```

<210> SEQ ID NO 12
<211> LENGTH: 124
<212> TYPE: PRT
<213> ORGANISM: Artificial Sequence
<220> FEATURE:
<223> OTHER INFORMATION: Synthetic

<400> SEQUENCE: 12

Glu Val Gln Leu Val Glu Thr Gly Gly Gly Leu Val Gln Ser Gly Gly
1               5                   10                  15

Ser Leu Arg Leu Ser Cys Glu Ala Ser Gly Phe Leu Phe Arg Ser Arg
            20                  25                  30

Gly Met Asn Trp Val Arg Gln Ala Pro Gly Lys Gly Leu Glu Trp Val
        35                  40                  45

Ser Gly Ile Ser Phe Asp Gly Arg Pro Ile Tyr Tyr Ala Asp Ala Val
    50                  55                  60

Arg Gly Arg Phe Thr Ile Ser Arg Asp Asn Ser Arg Asn Thr Leu Tyr
65                  70                  75                  80

Leu Glu Met Gln Ser Leu Glu Ile Glu Asp Thr Ala Val Tyr Tyr Cys
                85                  90                  95

Val Lys Gln Asn Gly Asp Thr Val Gly Thr Val Asp Gly Tyr Phe Asp
            100                 105                 110

Leu Trp Gly Gln Gly Ala Leu Val Asn Val Phe Ser
            115                 120

<210> SEQ ID NO 13
<211> LENGTH: 121
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ile Lys Tyr
            20                  25                  30

Gly Ile Asn Trp Val Arg Gln Ala Pro Gly Lys Gly Leu Glu Trp Val
        35                  40                  45

Ala Phe Ile Thr Tyr Glu Gly Ser Lys Lys Tyr Tyr Ala Asp Ala Val
    50                  55                  60

Thr Asp Arg Phe Thr Ile Ser Arg Asp Asn Ser Asn Asn Ile Leu Tyr
65                  70                  75                  80

Leu Gln Met Asn Asn Leu Lys Val Glu Asp Ser Ala Val Tyr Phe Cys
                85                  90                  95

Ala Arg Asp Arg Asp Tyr Phe Asp Ser Gly Tyr Trp Ala Tyr Trp Gly
            100                 105                 110

Gln Gly Val Leu Val Thr Val Ser Ser
        115                 120

<210> SEQ ID NO 14
<211> LENGTH: 124
<212> TYPE: PRT
<213> ORGANISM: Artificial Sequence
<220> FEATURE:
<223> OTHER INFORMATION: Synthetic

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Thr Tyr
            20                  25                  30

Gly Ile His Trp Val Arg Gln Ala Pro Gly Lys Gly Leu Glu Trp Val
        35                  40                  45

```
Ala Phe Ile Ser Ser Asp Gly Ser Lys Lys Tyr Tyr Val Asp Ser Met
 50                  55                  60

Lys Asp Arg Phe Thr Ile Ser Lys Asp Asn Ser Lys Asn Met Val Tyr
 65                  70                  75                  80

Leu Gln Leu Asn Asn Leu Lys Met Glu Asp Thr Ala Val Tyr Tyr Cys
                 85                  90                  95

Val Arg Pro Lys Met Arg Ile Ala Ala Val Leu Tyr Tyr Gly Leu Asp
            100                 105                 110

Ser Trp Gly Gln Gly Val Val Val Thr Val Ser Ser
            115                 120
```

```
<210> SEQ ID NO 15
<211> LENGTH: 120
<212> TYPE: PRT
<213> ORGANISM: Artificial Sequence
<220> FEATURE:
<223> OTHER INFORMATION: Synthetic

<400> SEQUENCE: 15

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
             20                  25                  30

Ser Met Tyr Trp Val Arg Gln Ala Pro Gly Lys Gly Leu Glu Trp Val
         35                  40                  45

Ala Leu Ile Ser Tyr Asp Gly Ser Lys Lys Tyr Tyr Ala Asp Ser Met
 50                  55                  60

Lys Gly Arg Phe Thr Ile Ser Arg Asp Asn Ser Lys Asn Met Leu Tyr
 65                  70                  75                  80

Leu Gln Lys Asn Asn Leu Lys Leu Glu Asp Thr Ala Val Tyr Tyr Cys
                 85                  90                  95

Ala Ser Arg Ser Tyr Ser Tyr Ser Phe Gly Leu Asp Ser Trp Gly Gln
            100                 105                 110

Gly Val Val Val Thr Val Ser Ser
            115                 120
```

```
<210> SEQ ID NO 16
<211> LENGTH: 120
<212> TYPE: PRT
<213> ORGANISM: Artificial Sequence
<220> FEATURE:
<223> OTHER INFORMATION: Synthetic

<400> SEQUENCE: 16

Glu Val Gln Leu Val Glu Ser Gly Gly Gly Leu Val Gln Pro Gly Gly
 1               5                   10                  15

Ser Leu Arg Leu Ser Cys Thr Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Arg Lys Tyr Tyr Ala Asp Ser Val
 50                  55                  60

Lys Asp Arg Phe Thr Ile Ser Arg Asp Asn Ser Lys Asn Met Leu Tyr
 65                  70                  75                  80

Leu Gln Met Thr Thr Leu Lys Leu Glu Asp Thr Ala Val Tyr Tyr Cys
                 85                  90                  95

Ala Arg Glu Ser Val Thr Leu Ser Tyr Tyr Phe Tyr Asn Trp Gly Gln
            100                 105                 110
```

```
Gly Val Leu Val Thr Val Ser Ser
        115                 120
```

<210> SEQ ID NO 17
<211> LENGTH: 118
<212> TYPE: PRT
<213> ORGANISM: Artificial Sequence
<220> FEATURE:
<223> OTHER INFORMATION: Synthetic

<400> SEQUENCE: 17

```
Glu Gln Leu Val Glu Ser Gly Gly Gly Leu Val Gln Pro Gly Ala Ser
1               5                   10                  15

Leu Arg Leu Ser Cys Ala Ala Ser Glu Phe Thr Phe Ser Leu Tyr Asp
            20                  25                  30

Met His Trp Val Arg Gln Ala Pro Gly Lys Gly Leu Glu Trp Ile Ser
        35                  40                  45

Gly Ile Asn Ile Gly Asp Gly Thr Tyr Tyr Ser Asp Ser Val Thr Gly
    50                  55                  60

Arg Ser Ile Ile Ser Arg Asp Asn Ala Lys Asn Ser Leu Tyr Leu Gln
65                  70                  75                  80

Val Asn Ser Leu Arg Thr Glu Asp Thr Gly Val Tyr Tyr Cys Thr Arg
                85                  90                  95

Thr Lys Gly Tyr Thr Ile Tyr Gly Leu Asp Ser Trp Gly Gln Gly Ala
            100                 105                 110

Val Val Thr Val Ser Ser
        115
```

<210> SEQ ID NO 18
<211> LENGTH: 126
<212> TYPE: PRT
<213> ORGANISM: Artificial Sequence
<220> FEATURE:
<223> OTHER INFORMATION: Synthetic

<400> SEQUENCE: 18

```
Asp Val Gln Leu Val Glu Ser Gly Gly Gly Leu Val Lys Pro Gly Gly
1               5                   10                  15

Phe Leu Arg Val Ser Cys Glu Gly Ser Gly Phe Thr Phe Ser His His
            20                  25                  30

Glu Met His Trp Val Arg Gln Ala Pro Gly Lys Gly Leu Glu Trp Val
        35                  40                  45

Ser Val Ile Ser Lys Thr Gly Asp Val Thr Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Thr Ala Glu Asp Thr Ala Val Tyr Phe Cys
                85                  90                  95

Thr Arg Val Ser Ile Ser Ile Leu Arg Val Asp Ile Lys Pro Val Tyr
            100                 105                 110

Phe Asp Val Trp Gly Pro Gly Val Leu Val Thr Val Ser Ser
        115                 120                 125
```

<210> SEQ ID NO 19
<211> LENGTH: 119
<212> TYPE: PRT
<213> ORGANISM: Artificial Sequence
<220> FEATURE:
<223> OTHER INFORMATION: Synthetic

<400> SEQUENCE: 19

Glu Val Gln Leu Met Glu Ser Gly Gly Gly Leu Ala Lys Pro Gly Gly
1               5                   10                  15

Ser Leu Arg Leu Ser Cys Ala Ala Ser Gly Phe Ile Phe Ser Asp His
            20                  25                  30

Tyr Met Asp Trp Val Arg Gln Ala Pro Gly Lys Gly Leu Asp Trp Val
        35                  40                  45

Ser Arg Ile Asp Asn Ala Gly His Ser Thr Trp Tyr Ala Asp Ser Ala
    50                  55                  60

Lys Asp Arg Phe Thr Met Ser Arg Asp Asn Thr Lys Asn Thr Leu Phe
65                  70                  75                  80

Leu Gln Met Asp Ser Leu Arg Gly Glu Asp Thr Ala Val Tyr Tyr Cys
                85                  90                  95

Ala Ala Ala Tyr Asp Arg Gln Tyr Ala Ile Asp His Trp Gly Gln Gly
            100                 105                 110

Val Leu Val Ile Val Ser Ser
        115

<210> SEQ ID NO 20
<211> LENGTH: 124
<212> TYPE: PRT
<213> ORGANISM: Artificial Sequence
<220> FEATURE:
<223> OTHER INFORMATION: Synthetic

<400> SEQUENCE: 20

Asp Met Gln Leu Val Glu Thr Gly Gly Gly Leu Val Gln Pro Gly Gly
1               5                   10                  15

Ser Leu Arg Leu Ser Cys Ala Ala Ser Gly Leu Ser Phe Ser Thr Tyr
            20                  25                  30

Gly Leu Asn Trp Val Arg Gln Ala Pro Gly Lys Gly Leu Glu Trp Val
        35                  40                  45

Ser Gly Leu Ser Tyr Ser Arg Gly Ser Thr Tyr Tyr Ala Asp Ser Val
    50                  55                  60

Lys Gly Arg Phe Thr Ile Ser Arg Asp Thr Ser Lys Asn Met Leu Thr
65                  70                  75                  80

Leu Gln Met Asn Ser Leu Arg Ile Glu Asp Thr Ala Val Tyr Tyr Cys
                85                  90                  95

Ala Lys Val Gly Gly Pro Thr Glu Ile Thr Pro Val Tyr Tyr Phe Tyr
            100                 105                 110

Tyr Trp Gly Pro Gly Val Gln Val Ile Val Ser Ser
        115                 120

<210> SEQ ID NO 21
<211> LENGTH: 115
<212> TYPE: PRT
<213> ORGANISM: Artificial Sequence
<220> FEATURE:
<223> OTHER INFORMATION: Synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Asn Lys Tyr
            20                  25                  30

Gly Met Thr Trp Val Arg Gln Ala Pro Gly Lys Gly Leu Glu Trp Val
        35                  40                  45

Ser Ser Ile Asn Asp Gly Gly Asp Ser Thr Phe Tyr Ala Glu Ser Val
            50                  55                  60

Lys Gly Arg Phe Val Ile Ser Arg Asp Asn Ser Lys Asn Met Leu Ser
 65                  70                  75                  80

Leu Gln Met Asn Ser Leu Thr Ile Ala Asp Thr Ala Val Tyr Tyr Cys
                85                  90                  95

Ala Thr Gly Ser Asn Tyr Asp Tyr Trp Gly Gln Gly Val Leu Val Ser
            100                 105                 110

Val Ser Ser
        115

<210> SEQ ID NO 22
<211> LENGTH: 120
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Ala Lys Pro Gly Gly
 1               5                  10                  15

Ser Leu Arg Leu Thr Cys Val Ala Ser Gly Phe Thr Phe Ser Asn Tyr
                20                  25                  30

Ala Met His Trp Val Arg Gln Ala Pro Gly Lys Gly Leu Asp Trp Val
            35                  40                  45

Ser Gly Ile Asn Ser Gly Gly Ser Thr Tyr Tyr Ala Asp Ser Val Lys
        50                  55                  60

Gly Arg Phe Thr Ile Ser Arg Asp Asn Ser Asn Asn Thr Leu Ser Leu
 65                  70                  75                  80

Gln Met Asp Ser Leu Arg Thr Glu Asp Met Ala Val Tyr Tyr Cys Ala
                85                  90                  95

Lys Asp Pro Glu Trp Ile Thr Ala Tyr Gly Leu Asp Ser Trp Gly Gln
            100                 105                 110

Gly Ala Val Val Thr Val Ser Ser
        115                 120

<210> SEQ ID NO 23
<211> LENGTH: 116
<212> TYPE: PRT
<213> ORGANISM: Artificial Sequence
<220> FEATURE:
<223> OTHER INFORMATION: Synthetic

<400> SEQUENCE: 23

Glu Glu Leu Leu Met Asp Leu Gly Gly Gly Leu Ala Gln Pro Gly Gly
 1               5                  10                  15

Ser Leu Arg Ile Ser Cys Ala Ala Ser Arg Phe Thr Phe Asn Tyr Tyr
                20                  25                  30

Gly Met Asn Trp Val Arg Gln Ala Pro Gly Lys Gly Leu Glu Trp Ile
            35                  40                  45

Ser Gly Ile Asn Gly Gly Gly Asp Thr Thr Tyr Tyr Ala Asp Ser Val
        50                  55                  60

Arg Gly Arg Phe Thr Ile Ser Arg Asp Asn Glu Asn Thr Leu Ser
 65                  70                  75                  80

Leu Gln Met Asn Ser Leu Arg Val Glu Asp Thr Ala Val Tyr Tyr Cys
                85                  90                  95

Ala Lys Arg Gly Leu Ala Leu Asp Val Trp Gly Arg Gly Ile Leu Val

Thr Val Ser Ser
        115

<210> SEQ ID NO 24
<211> LENGTH: 116
<212> TYPE: PRT
<213> ORGANISM: Artificial Sequence
<220> FEATURE:
<223> OTHER INFORMATION: Synthetic

<400> SEQUENCE: 24

Glu Val Gln Leu Val Glu Thr Gly Gly Gly Leu Ala Lys Pro Gly Gly
1               5                   10                  15

Ser Leu Arg Leu Ser Cys Ala Ala Ser Gly Leu Thr Phe Ser Thr Tyr
            20                  25                  30

Ser Met His Trp Val Arg Gln Ala Pro Gly Lys Gly Leu Glu Trp Ile
        35                  40                  45

Ser Ala Ile Asn Ser Gly Gly Gly Ser Ile Trp Tyr Ile Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Pro Glu Asp Thr Ala Val Tyr Tyr Cys
                85                  90                  95

Ala Lys Gly Gly Leu Ala Leu Asp Val Trp Gly Arg Gly Val Leu Val
            100                 105                 110

Thr Val Ser Ser
        115

<210> SEQ ID NO 25
<211> LENGTH: 132
<212> TYPE: PRT
<213> ORGANISM: Artificial Sequence
<220> FEATURE:
<223> OTHER INFORMATION: Synthetic

<400> SEQUENCE: 25

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Ser
            20                  25                  30

Gly Leu Gly Val Gly Trp Ile His Gln Ser Pro Gly Arg Thr Leu Glu
        35                  40                  45

Trp Leu Gly Thr Ile Phe Trp Asp Gly Asp Arg Asn Tyr Asn Thr Ser
    50                  55                  60

Leu Gly Asn Arg Ile Thr Ile Ser Lys Asp Thr Ser Thr Asn Gln Val
65                  70                  75                  80

Val Leu Thr Leu Thr Asp Val Asp Pro Leu Asp Thr Gly Thr Tyr Tyr
                85                  90                  95

Cys Ala Arg Gly Ser Gly Pro Leu Lys Trp Ile Pro Lys Leu Arg Asn
            100                 105                 110

Tyr Gln Lys Cys Pro Ala Phe His Leu Trp Gly Pro Gly Leu Ser Val
        115                 120                 125

Thr Val Ser Ser
        130

<210> SEQ ID NO 26
<211> LENGTH: 131

<212> TYPE: PRT
<213> ORGANISM: Artificial Sequence
<220> FEATURE:
<223> OTHER INFORMATION: Synthetic

<400> SEQUENCE: 26

Gln Ile Thr Leu Lys Glu Ser Gly Pro Ala Leu Ile Asn Pro Thr Gln
1               5                   10                  15

Thr Leu Thr Leu Thr Cys Thr Phe Ser Gly Phe Ser Phe Ser Asp Ser
            20                  25                  30

Gly Thr Gly Val Ala Trp Ile Arg Gln Pro Pro Gly Lys Ala Leu Glu
        35                  40                  45

Trp Leu Thr Ser Ile Tyr Trp Asn Asp Gly Lys Tyr Trp Ser Pro Ser
    50                  55                  60

Leu Glu Asn Arg Leu Ser Val Phe Lys Asp Pro Ser Lys Asn Gln Val
65                  70                  75                  80

Val Leu Arg Met Thr Asn Met Asp Pro Glu Asp Thr Ala Thr Tyr Tyr
                85                  90                  95

Cys Ala Trp Leu Gln Leu Thr Arg Val Thr Ile Ser Gly Val Val Lys
            100                 105                 110

Tyr Gly Gln Gly Arg Phe Glu Val Trp Gly Gln Gly Ala Val Val Thr
        115                 120                 125

Val Ser Ser
    130

<210> SEQ ID NO 27
<211> LENGTH: 124
<212> TYPE: PRT
<213> ORGANISM: Artificial Sequence
<220> FEATURE:
<223> OTHER INFORMATION: Synthetic

<400> SEQUENCE: 27

Gln Ile Thr Leu Lys Glu Ser Gly Pro Thr Leu Val Arg Pro Thr Gln
1               5                   10                  15

Thr Leu Thr Leu Thr Cys Thr Phe Ser Gly Phe Ser Ile Thr Thr Ser
            20                  25                  30

Lys Thr Gly Val Gly Trp Ile Arg Gln Pro Pro Gly Lys Ala Leu Glu
        35                  40                  45

Trp Leu Gly Asn Ile Tyr Trp Asn Gly Asp Lys Ser Tyr Thr Pro Ser
    50                  55                  60

Leu Lys Arg Gly Leu Thr Ile Ser Lys Asp Thr Thr Lys Asn Gln Val
65                  70                  75                  80

Leu Leu Thr Leu Thr Asn Leu Ala Pro Val Asp Thr Ala Thr Tyr Tyr
                85                  90                  95

Cys Ala Arg Leu Tyr Val Met Asn Val Leu Thr Ala Gly Gly Phe Tyr
            100                 105                 110

Tyr Trp Gly Gln Gly Ile Leu Val Thr Val Ser Ser
        115                 120

<210> SEQ ID NO 28
<211> LENGTH: 124
<212> TYPE: PRT
<213> ORGANISM: Artificial Sequence
<220> FEATURE:
<223> OTHER INFORMATION: Synthetic

<400> SEQUENCE: 28

Gln Val Thr Leu Lys Glu Ser Gly Pro Ala Leu Val Lys Pro Thr Gln

```
                1               5                   10                  15
            Thr Leu Thr Leu Thr Cys Thr Phe Ser Gly Phe Ser Leu Ser Thr Ser
                            20                  25                  30

Gly Met Gly Val Gly Trp Ile Arg Gln Pro Pro Gly Lys Ala Leu Glu
                        35                  40                  45

Trp Leu Ala Leu Ile Tyr Trp Asp Asp Lys Arg Tyr Ser Thr Ser
                50                  55                  60

Leu Lys Ser Arg Leu Thr Ile Ser Lys Asp Thr Ser Lys Asn Gln Val
             65                  70                  75                  80

Val Leu Thr Met Thr Asn Met Asp Pro Val Asp Thr Ala Thr Tyr Tyr
                            85                  90                  95

Cys Ala Arg Gly Asp Trp Gly Thr Val Gly Thr Val Asp Tyr Phe Tyr
                            100                 105                 110

Tyr Trp Gly Gln Gly Val Leu Val Thr Val Ser Ser
                        115                 120
```

<210> SEQ ID NO 29
<211> LENGTH: 124
<212> TYPE: PRT
<213> ORGANISM: Artificial Sequence
<220> FEATURE:
<223> OTHER INFORMATION: Synthetic

<400> SEQUENCE: 29

```
            Gln Val Arg Leu Gln Glu Ser Gly Pro Gly Leu Val Lys Pro Ser Gln
             1               5                   10                  15

Thr Leu Ser Leu Thr Cys Ala Ile Ser Gly Asp Thr Val Ser Arg Tyr
                            20                  25                  30

Ser Ala Thr Trp Asn Trp Val Arg Gln Ser Pro Ser Arg Gly Leu Glu
                        35                  40                  45

Trp Leu Gly Arg Thr Tyr Phe Arg Ser Lys Trp Tyr Ser Asp Tyr Ala
                50                  55                  60

Gln Ser Val Glu Asn Arg Ile Thr Ile Gly Ser Asp Thr Ser Arg Asn
             65                  70                  75                  80

Gln Phe Ser Leu Glu Val Asn Ser Val Ser Pro Glu Asp Thr Ala Val
                            85                  90                  95

Tyr Phe Cys Thr Arg Val Gln Trp Gly His Leu Met Arg Trp Phe Asp
                            100                 105                 110

Val Trp Gly Pro Gly Ile Leu Val Thr Val Ala Ser
                        115                 120
```

<210> SEQ ID NO 30
<211> LENGTH: 126
<212> TYPE: PRT
<213> ORGANISM: Artificial Sequence
<220> FEATURE:
<223> OTHER INFORMATION: Synthetic

<400> SEQUENCE: 30

```
            Gln Val Gln Leu Gln Glu Ser Gly Pro Gly Leu Val Lys Pro Ser Gln
             1               5                   10                  15

Thr Leu Ser Leu Thr Cys Ala Ile Ser Gly Asp Ser Val Ser Ser Asn
                            20                  25                  30

Ser Ala Thr Trp Asn Trp Ile Arg Gln Ser Pro Ser Arg Gly Leu Glu
                        35                  40                  45

Trp Leu Gly Arg Thr Tyr Tyr Arg Ser Lys Trp Tyr Asn Asp Tyr Ala
                50                  55                  60
```

```
Gln Ser Val Gln Asn Arg Ile Thr Ile Asn Pro Asp Thr Ser Lys Asn
 65                  70                  75                  80

Gln Phe Ser Leu Gln Leu Asn Ser Val Thr Pro Glu Asp Met Ala Val
                 85                  90                  95

Tyr Tyr Cys Ala Arg Gly Gly Ala Leu Met Asp Val Trp Gly Ser Trp
            100                 105                 110

Phe Asp Val Trp Gly Pro Gly Val Leu Val Thr Val Ser Ser
            115                 120                 125
```

<210> SEQ ID NO 31
<211> LENGTH: 120
<212> TYPE: PRT
<213> ORGANISM: Artificial Sequence
<220> FEATURE:
<223> OTHER INFORMATION: Synthetic

<400> SEQUENCE: 31

```
Gln Val Gln Leu Gln Glu Ser Gly Pro Gly Leu Val Arg Pro Ser Glu
 1               5                  10                  15

Thr Leu Ser Leu Thr Cys Ala Val Ser Gly Asp Ser Val Ser Ser Ile
             20                  25                  30

Asn Trp Trp Ser Trp Ile Arg Gln Ser Pro Gly Lys Gly Leu Asp Trp
         35                  40                  45

Ile Gly Ser Leu Ser Gly Ser Gly Gly Thr Ile Tyr Leu Asn Pro Ser
 50                  55                  60

Leu Lys Ser Arg Val Asn Leu Ser Ile Asp Thr Ser Arg Asn His Leu
 65                  70                  75                  80

Ser Phe Asn Leu Thr Ser Val Thr Ser Ala Asp Thr Ala Val Tyr Tyr
                 85                  90                  95

Cys Ala Arg His Glu Ile Val Gly Asn Ala Leu Tyr Phe Trp Gly Gln
            100                 105                 110

Gly Val Leu Val Thr Val Ser Ser
            115                 120
```

<210> SEQ ID NO 32
<211> LENGTH: 127
<212> TYPE: PRT
<213> ORGANISM: Artificial Sequence
<220> FEATURE:
<223> OTHER INFORMATION: Synthetic

<400> SEQUENCE: 32

```
Gln Val Gln Leu Gln Glu Ser Gly Pro Ala Val Val Lys Pro Ser Glu
 1               5                  10                  15

Thr Leu Ser Leu Thr Cys Val Val Ser Gly Gly Ser Ile Ser Gly Gly
             20                  25                  30

Tyr Gly Trp Ser Trp Ile Arg Gln Ala Pro Arg Lys Gly Leu Glu Trp
         35                  40                  45

Ile Gly Ser Ile Tyr Gly Leu Ser Gly Gly Thr Phe Tyr Asn Pro Ser
 50                  55                  60

Leu Lys Ser Arg Ile Thr Ile Ser Lys Asp Thr Ser Lys Thr Gln Val
 65                  70                  75                  80

Ser Leu Lys Leu Ser Pro Val Thr Val Ala Asp Thr Ala Val Tyr Tyr
                 85                  90                  95

Cys Ala Arg Gln Phe Arg Tyr Asn Ser Gly Trp Ala Pro Glu Asn Tyr
            100                 105                 110

Gly Leu Asp Phe Trp Gly Gln Gly Ala Val Val Thr Val Ser Ser
            115                 120                 125
```

<210> SEQ ID NO 33
<211> LENGTH: 112
<212> TYPE: PRT
<213> ORGANISM: Artificial Sequence
<220> FEATURE:
<223> OTHER INFORMATION: Synthetic

<400> SEQUENCE: 33

Gln Val Gln Leu Gln Glu Ser Gly Pro Gly Leu Val Lys Pro Leu Glu
1               5                   10                  15

Thr Leu Ser Leu Thr Cys Gly Val Ser Gly Gly Ser Ile Ser Ser Asn
            20                  25                  30

His Trp Ser Trp Ile Arg Gln Ala Pro Gly Lys Gly Leu Glu Trp Ile
        35                  40                  45

Gly Leu Phe Thr Tyr Ser Gly Ser Ala Asn Tyr Asn Ser Tyr Leu Lys
    50                  55                  60

Ser Arg Val Thr Leu Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Val Gly Glu Pro Trp Gly Gln Gly Leu Arg Val Thr Val Ser Ser
            100                 105                 110

<210> SEQ ID NO 34
<211> LENGTH: 117
<212> TYPE: PRT
<213> ORGANISM: Artificial Sequence
<220> FEATURE:
<223> OTHER INFORMATION: Synthetic

<400> SEQUENCE: 34

Gln Val Gln Met Gln Glu Ser Gly Pro Gly Leu Val Lys Pro Ser Glu
1               5                   10                  15

Thr Leu Ser Val Thr Cys Ala Phe Ser Gly Asp Ser Ile Ser Asn Tyr
            20                  25                  30

Tyr Trp Ser Trp Phe Arg Gln Ser Pro Gly Lys Gly Leu Glu Trp Ile
        35                  40                  45

Gly Tyr Ile Tyr Gly Ser Asp Arg Thr Ile Lys Tyr Asn Pro Ser Leu
    50                  55                  60

Lys Ser Arg Ala Thr Leu Ser Val Asp Thr Ser Lys Asn Gln Phe Ser
65                  70                  75                  80

Leu Lys Leu Asp Ser Val Thr Ala Ala Asp Thr Ala Val Tyr Tyr Cys
                85                  90                  95

Ala Arg Asp Arg Met Trp Gly Val Tyr Tyr Trp Gly Pro Gly Val Leu
            100                 105                 110

Val Thr Val Ser Ser
115

<210> SEQ ID NO 35
<211> LENGTH: 123
<212> TYPE: PRT
<213> ORGANISM: Artificial Sequence
<220> FEATURE:
<223> OTHER INFORMATION: Synthetic

<400> SEQUENCE: 35

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Asp Ser Ile Ser Asn Tyr
            20                  25                  30

Tyr Trp Thr Trp Ile Arg Gln Pro Pro Gly Lys Gly Leu Glu Trp Ile
        35                  40                  45

Gly Tyr Ile Tyr Gly Ser Gly Ser Thr Tyr Tyr Asn Pro Ser Leu Lys
    50                  55                  60

Ser Arg Val Thr Ile Ser Lys Asp Thr Ser Lys Asn Gln Tyr Ser Leu
65                  70                  75                  80

Lys Val Asn Ser Ala Thr Ala Ala Asp Thr Ala Ala Tyr Tyr Cys Ala
                85                  90                  95

Arg Glu Gly Gly Val Ala Ala Asp Leu Gly Gly Asn Trp Leu Asp Val
            100                 105                 110

Trp Gly Pro Gly Val Arg Val Thr Val Ser Ser
        115                 120

<210> SEQ ID NO 36
<211> LENGTH: 121
<212> TYPE: PRT
<213> ORGANISM: Artificial Sequence
<220> FEATURE:
<223> OTHER INFORMATION: Synthetic

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Ile Ser Gly Tyr
            20                  25                  30

Tyr Trp Asn Trp Ile Arg Gln Pro Pro Gly Lys Gly Leu Glu Trp Ile
        35                  40                  45

Gly Tyr Ile Gly Gly Ser Ser Gly Ser Thr Asp Tyr Asn Pro Ser Leu
    50                  55                  60

Lys Ser Arg Val Thr Ile Ser Thr Asp Thr Ser Lys Asn Gln Phe Ser
65                  70                  75                  80

Leu Lys Leu Thr Ser Val Thr Ala Ala Asp Thr Ala Ile Tyr Tyr Cys
                85                  90                  95

Ala Arg His Ser Asp Thr Val Gly Gly Tyr Ser Leu Asp Val Trp Gly
            100                 105                 110

Arg Gly Val Leu Val Thr Val Ser Ser
        115                 120

<210> SEQ ID NO 37
<211> LENGTH: 122
<212> TYPE: PRT
<213> ORGANISM: Artificial Sequence
<220> FEATURE:
<223> OTHER INFORMATION: Synthetic

<400> SEQUENCE: 37

Gln Val Gln Leu Gln Asp Ser Gly Pro Gly Leu Val Lys Pro Ser Glu
1               5                   10                  15

Thr Leu Ser Leu Thr Cys Ala Val Ser Gly Gly Ser Ile Ser Gly Tyr
            20                  25                  30

Tyr Trp Asn Trp Ile Arg Gln Pro Pro Gly Lys Gly Leu Glu Trp Ile
        35                  40                  45

Gly Tyr Ile Gly Gly Ser Ser Gly Ser Thr Asp Tyr Ile Pro Ser Leu
    50                  55                  60

Lys Ser Arg Val Thr Leu Ser Val Asp Thr Ser Lys Asn Gln Phe Ser
65                  70                  75                  80
```

```
Leu Lys Leu Ser Ser Val Thr Ala Ala Asp Thr Ala Val Tyr Tyr Cys
                85                  90                  95

Ala Arg Asn Gly Arg Thr Ala Ala Thr Asp Tyr Gly Leu Asp Ser Trp
            100                 105                 110

Gly Gln Gly Val Val Thr Val Ser Ser
        115                 120
```

<210> SEQ ID NO 38
<211> LENGTH: 113
<212> TYPE: PRT
<213> ORGANISM: Artificial Sequence
<220> FEATURE:
<223> OTHER INFORMATION: Synthetic

<400> SEQUENCE: 38

```
Asp Val Val Met Thr Gln Ser Pro Leu Ser Leu Pro Ile Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu Ser Trp Tyr Gln Gln Lys Pro Gly Gln Pro
        35                  40                  45

Pro Arg Leu Leu Ile Tyr Gln Val Ser Asn Arg Tyr Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Asp Asp Val Gly Val Tyr Tyr Cys Gly Gln Gly
                85                  90                  95

Ala His Leu Pro Arg Thr Phe Gly Gln Gly Thr Lys Val Glu Ile Lys
            100                 105                 110

Arg
```

<210> SEQ ID NO 39
<211> LENGTH: 113
<212> TYPE: PRT
<213> ORGANISM: Artificial Sequence
<220> FEATURE:
<223> OTHER INFORMATION: Synthetic

<400> SEQUENCE: 39

```
Asp Val Val Met Thr Gln Ser Pro Leu Ser Leu Pro Ile Thr Pro Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Tyr Gln Gln Lys Pro Gly Gln Pro
        35                  40                  45

Pro Arg Leu Leu Ile Tyr Lys Val Ser Asn Arg Tyr Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Lys Val Pro Leu Thr Phe Gly Gly Gly Thr Lys Val Glu Ile Lys
            100                 105                 110

Arg
```

<210> SEQ ID NO 40
<211> LENGTH: 113

```
<212> TYPE: PRT
<213> ORGANISM: Artificial Sequence
<220> FEATURE:
<223> OTHER INFORMATION: Synthetic

<400> SEQUENCE: 40

Asp Ile Val Met Thr Gln Thr Pro Leu Ser Leu Pro Val Thr Leu Gly
1               5                   10                  15

Glu Pro Ala Ser Ile Ser Cys Arg Ser Ser Gln Ser Leu Val Tyr Ser
            20                  25                  30

Asp Gly Lys Thr Tyr Leu Asp Trp Tyr Leu Gln Lys Pro Gly Gln Ser
        35                  40                  45

Pro Gln Leu Leu Met Tyr Leu Val Ser Lys Arg Ala Ser Gly Val Pro
    50                  55                  60

Asp Lys Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Arg Ser Pro Leu Thr Phe Gly Gly Gly Thr Lys Val Glu Ile Lys
            100                 105                 110

Arg

<210> SEQ ID NO 41
<211> LENGTH: 114
<212> TYPE: PRT
<213> ORGANISM: Artificial Sequence
<220> FEATURE:
<223> OTHER INFORMATION: Synthetic

<400> SEQUENCE: 41

Asp Ile Val Met Thr Gln Ala Pro Val Ser Leu Pro Val Ile Pro Gly
1               5                   10                  15

Glu Ser Ala Ser Ile Ser Cys Arg Ser Ser Gln Ser Leu Phe Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Glu Val Ser Asn Arg Ala Ser Gly Val
    50                  55                  60

Pro Asp Arg Phe Ser Gly Ser Gly Ser Asp Thr Asp Phe Thr Leu Lys
65                  70                  75                  80

Ile Arg Arg Val Glu Ala Glu Asp Ala Gly Val Tyr Tyr Cys Met Gln
                85                  90                  95

Gly Val Glu Phe Pro Tyr Ser Phe Gly Gln Gly Thr Lys Val Glu Phe
            100                 105                 110

Lys Arg

<210> SEQ ID NO 42
<211> LENGTH: 114
<212> TYPE: PRT
<213> ORGANISM: Artificial Sequence
<220> FEATURE:
<223> OTHER INFORMATION: Synthetic

<400> SEQUENCE: 42

Asp Ile Val Thr Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30
```

Glu Asp Gly Lys Thr Phe Leu Asp Trp Tyr Leu Gln Lys Pro Gly Gln
            35                  40                  45

Ser Pro Gln Leu Leu Ile Tyr Glu Val Ser Asn Arg Ala Ser Gly Val
 50                  55                  60

Pro Asp Arg Phe Ser Gly Ser Gly Ser Asp Thr Asp Phe Thr Leu Lys
65                  70                  75                  80

Ile Ser Arg Val Glu Ala Glu Asp Val Gly Val Tyr Tyr Cys Met Gln
                85                  90                  95

Ser Met Lys Phe Pro Phe Thr Phe Gly Pro Gly Thr Lys Leu Asp Ile
            100                 105                 110

Lys Arg

<210> SEQ ID NO 43
<211> LENGTH: 115
<212> TYPE: PRT
<213> ORGANISM: Artificial Sequence
<220> FEATURE:
<223> OTHER INFORMATION: Synthetic

<400> SEQUENCE: 43

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
            35                  40                  45

Ser Pro Gln Leu Leu Ile Tyr Glu Val Ser Asn Arg Ala Ser Gly Val
 50                  55                  60

Pro Asp Arg Phe Ser Gly Ser Gly Ser Asp Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Ile Glu Phe Pro Leu Tyr Ser Phe Gly Gln Gly Thr Lys Val Glu
            100                 105                 110

Ile Lys Arg
        115

<210> SEQ ID NO 44
<211> LENGTH: 114
<212> TYPE: PRT
<213> ORGANISM: Artificial Sequence
<220> FEATURE:
<223> OTHER INFORMATION: Synthetic

<400> SEQUENCE: 44

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Glu Trp Tyr Leu Gln Lys Pro Gly Gln
            35                  40                  45

Ser Pro Gln Pro Leu Ile Tyr Glu Val Ser Asn Arg Ala Ser Gly Val
 50                  55                  60

Pro Asp Arg Phe Ser Gly Ser Gly Ser Asp Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Ile Glu Tyr Pro Trp Thr Phe Gly Gln Gly Thr Lys Val Glu Ile
            100                 105                 110

Lys Arg

<210> SEQ ID NO 45
<211> LENGTH: 114
<212> TYPE: PRT
<213> ORGANISM: Artificial Sequence
<220> FEATURE:
<223> OTHER INFORMATION: Synthetic

<400> SEQUENCE: 45

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Phe Leu Ile Tyr Glu Val Ser Asn Arg Ala Ser Gly Val
    50                  55                  60

Pro Asp Arg Phe Ser Gly Ser Gly Pro Asp Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Ile Glu Phe Pro Trp Thr Phe Gly Gln Gly Thr Lys Val Glu Ile
            100                 105                 110

Lys Arg

<210> SEQ ID NO 46
<211> LENGTH: 108
<212> TYPE: PRT
<213> ORGANISM: Artificial Sequence
<220> FEATURE:
<223> OTHER INFORMATION: Synthetic'

<400> SEQUENCE: 46

Gln Ile Ile Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ser Trp Tyr Gln Gln Lys Pro Gly Gln Ala Pro Arg Leu Leu Ile
        35                  40                  45

Trp Gly Ala Thr Arg Arg Ala Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Ile Tyr Tyr Cys Gln Lys Tyr Asp Asn Ser Pro Tyr
                85                  90                  95

Ser Phe Gly Gln Gly Thr Lys Val Glu Ile Asn Arg
            100                 105

<210> SEQ ID NO 47
<211> LENGTH: 107
<212> TYPE: PRT
<213> ORGANISM: Artificial Sequence
<220> FEATURE:
<223> OTHER INFORMATION: Synthetic

<400> SEQUENCE: 47

```
Gln Val Ile Leu Thr Gln Ser Pro Ala Thr Leu Ser Leu Ser Pro Gly
1               5                   10                  15

Asp Arg Ala Thr Leu Ser Cys Arg Ala Ser Gln Ser Val Asp Arg Ser
            20                  25                  30

Leu Ala Trp Tyr Gln Gln Pro Gly Gln Ala Pro Arg Leu Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Leu Tyr Tyr Cys Gln Lys Tyr Thr Thr Ser Trp Thr
                85                  90                  95

Phe Gly Gln Gly Thr Lys Val Glu Leu Lys Arg
            100                 105
```

<210> SEQ ID NO 48
<211> LENGTH: 108
<212> TYPE: PRT
<213> ORGANISM: Artificial Sequence
<220> FEATURE:
<223> OTHER INFORMATION: Synthetic

<400> SEQUENCE: 48

```
Gln Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Lys Tyr Ser Ser Pro Pro His
                85                  90                  95

Ser Phe Gly Gln Gly Thr Lys Val Glu Ile Lys Arg
            100                 105
```

<210> SEQ ID NO 49
<211> LENGTH: 108
<212> TYPE: PRT
<213> ORGANISM: Artificial Sequence
<220> FEATURE:
<223> OTHER INFORMATION: Synthetic

<400> SEQUENCE: 49

```
Gln Ala Ile Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ala Ser Ser
            20                  25                  30

Leu Ala Trp Tyr Gln Gln Lys Ala Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Glu Phe Ile Leu Thr Ile Ser Ser Leu Glu Pro
65                  70                  75                  80

Glu Asp Phe Ala Val Tyr Tyr Cys Gln Lys Tyr Ser Ser Ser Pro Phe
                85                  90                  95
```

```
Thr Phe Gly Pro Gly Thr Arg Leu Asp Ile Lys Arg
            100                 105
```

<210> SEQ ID NO 50
<211> LENGTH: 108
<212> TYPE: PRT
<213> ORGANISM: Artificial Sequence
<220> FEATURE:
<223> OTHER INFORMATION: Synthetic

<400> SEQUENCE: 50

```
Gln Val Ile Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Lys Tyr Ser Asn Ser Pro Leu
                85                  90                  95

Thr Phe Gly Gly Gly Thr Lys Val Glu Ile Lys Arg
            100                 105
```

<210> SEQ ID NO 51
<211> LENGTH: 107
<212> TYPE: PRT
<213> ORGANISM: Artificial Sequence
<220> FEATURE:
<223> OTHER INFORMATION: Synthetic

<400> SEQUENCE: 51

```
Gln Val Ile Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Phe Ala Val Tyr Tyr Cys Gln Lys Tyr Ser Ser Ser Pro Thr
                85                  90                  95

Phe Gly Gln Gly Thr Lys Val Glu Ile Lys Arg
            100                 105
```

<210> SEQ ID NO 52
<211> LENGTH: 107
<212> TYPE: PRT
<213> ORGANISM: Artificial Sequence
<220> FEATURE:
<223> OTHER INFORMATION: Synthetic

<400> SEQUENCE: 52

```
Gln Ile Val Leu Thr Gln Ser Pro Ala Thr Leu Ser Leu Ser Pro Gly
1               5                   10                  15
```

Glu Arg Ala Thr Leu Ser Cys Arg Ala Ser Gln Asn Val Gly Asp Tyr
            20                  25                  30

Leu Ala Trp Tyr His Gln Lys Pro Gly Gln Ala Pro Arg Leu Leu Ile
        35                  40                  45

His Ser Val Ser Thr Arg Ala Thr Gly Ile Pro Asp Lys Phe Ile Gly
    50                  55                  60

Ser Gly Ser Gly Thr Gln Phe Thr Leu Thr Ile Ser Arg Leu Glu Ser
65                  70                  75                  80

Glu Asp Val Gly Val Tyr His Cys Tyr Gln Tyr Tyr Asn Asn Tyr Ser
                85                  90                  95

Phe Gly Gln Gly Thr Lys Val Glu Ile Lys Arg
            100                 105

<210> SEQ ID NO 53
<211> LENGTH: 107
<212> TYPE: PRT
<213> ORGANISM: Artificial Sequence
<220> FEATURE:
<223> OTHER INFORMATION: Synthetic

<400> SEQUENCE: 53

Gln Val Ile Leu Thr Gln Ser Pro Ala Thr Leu Ser Leu Ser Pro Gly
1               5                   10                  15

Glu Arg Ala Thr Leu Ser Cys Arg Ala Gly Gln Thr Val Ser Thr Phe
            20                  25                  30

Leu Ala Trp Tyr Gln Gln Lys Pro Gly Gln Ala Pro Arg Leu Leu Val
        35                  40                  45

His Ser Ala Ser Lys Arg Ala Ala Gly Thr Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Val Gly Ile Tyr His Cys Tyr Gln Tyr Tyr Asp Lys Trp Thr
                85                  90                  95

Phe Gly Gln Gly Thr Lys Val Glu Ile Lys Arg
            100                 105

<210> SEQ ID NO 54
<211> LENGTH: 107
<212> TYPE: PRT
<213> ORGANISM: Artificial Sequence
<220> FEATURE:
<223> OTHER INFORMATION: Synthetic

<400> SEQUENCE: 54

Gln Val Ile Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

His Ser Ala Ser Ser Arg Ala Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Val Gly Val Tyr His Cys Tyr Gln Tyr Tyr Thr Gly Tyr Ser
                85                  90                  95

Phe Gly Gln Gly Thr Lys Val Glu Ile Lys Arg
            100                 105

<210> SEQ ID NO 55
<211> LENGTH: 107
<212> TYPE: PRT
<213> ORGANISM: Artificial Sequence
<220> FEATURE:
<223> OTHER INFORMATION: Synthetic

<400> SEQUENCE: 55

Glu Val Val Met Thr Gln Ser Pro Ala Thr Leu Ser Leu Ser Pro Gly
1               5                   10                  15

Glu Thr Ala Thr Ile Ser Cys Arg Thr Ser Gln Ser Ile Ser Ala Lys
            20                  25                  30

Leu Ala Trp Tyr Gln His Lys Pro Gly Gln Ala Pro Arg Val Val Ile
        35                  40                  45

Tyr Ser Ala Ser Lys Arg Ala Thr Gly Ile Pro Gly Arg Phe Ser Gly
    50                  55                  60

Arg Gly Ser Glu Thr Asp Phe Thr Leu Thr Ile Ser Ser Leu Glu Pro
65                  70                  75                  80

Glu Asp Phe Ala Val Tyr Phe Cys Gln Glu Thr Arg Asn Phe Trp Thr
                85                  90                  95

Phe Gly Gln Gly Thr Lys Val Glu Val Lys Arg
            100                 105

<210> SEQ ID NO 56
<211> LENGTH: 108
<212> TYPE: PRT
<213> ORGANISM: Artificial Sequence
<220> FEATURE:
<223> OTHER INFORMATION: Synthetic

<400> SEQUENCE: 56

Glu Ile Leu Met Thr Gln Ser Pro Ala Thr Leu Val Leu Ser Pro Gly
1               5                   10                  15

Leu Arg Ala Thr Leu Ser Cys Arg Ala Ser Gln Asn Val Ser Asn Tyr
            20                  25                  30

Leu Ala Trp Tyr His Lys Lys Pro Gly Gln Ala Pro Arg Leu Leu Ile
        35                  40                  45

Tyr Gly Ala Ser Asn Arg Ala Thr Gly Ile Pro Asp Arg Phe Ser Gly
    50                  55                  60

Ser Gly Ser Gly Thr Glu Phe Thr Leu Thr Ile Ser Ser Leu Glu Pro
65                  70                  75                  80

Glu Asp Val Gly Val Tyr Phe Cys Leu Gln Ser Ser Asn Trp Pro Leu
                85                  90                  95

Thr Phe Gly Gly Gly Thr Lys Val Glu Ile Lys Arg
            100                 105

<210> SEQ ID NO 57
<211> LENGTH: 107
<212> TYPE: PRT
<213> ORGANISM: Artificial Sequence
<220> FEATURE:
<223> OTHER INFORMATION: Synthetic

<400> SEQUENCE: 57

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

```
Leu Ala Trp Tyr Gln Gln Lys Pro Gly Gln Ala Pro Arg Leu Leu Ile
             35                  40                  45

Tyr Asp Ala Ser Ser Arg Ala Thr Gly Ile Pro Asp Arg Phe Ser Gly
 50                  55                  60

Ser Gly Ser Gly Thr Glu Phe Thr Leu Thr Ile Ser Ser Leu Glu Pro
 65                  70                  75                  80

Glu Asp Val Ala Val Tyr Phe Cys Gln Gln Glu Ser Asn Trp Trp Thr
                 85                  90                  95

Phe Gly Gln Gly Thr Lys Val Glu Ile Lys Arg
            100                 105
```

<210> SEQ ID NO 58
<211> LENGTH: 108
<212> TYPE: PRT
<213> ORGANISM: Artificial Sequence
<220> FEATURE:
<223> OTHER INFORMATION: Synthetic

<400> SEQUENCE: 58

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Arg Val Gly Ser Asn
             20                  25                  30

Leu Asp Trp Tyr Gln Gln Lys Pro Gly Gln Pro Pro Arg Leu Leu Ile
         35                      40                  45

Tyr Tyr Thr Ser Asn Arg Ala Thr Gly Ile Pro Glu Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Val Gly Val Tyr Tyr Cys Gln Gln Glu Asn Asn Trp Pro Leu
                 85                  90                  95

Thr Phe Gly Gly Gly Thr Lys Val Glu Ile Lys Arg
            100                 105
```

<210> SEQ ID NO 59
<211> LENGTH: 108
<212> TYPE: PRT
<213> ORGANISM: Artificial Sequence
<220> FEATURE:
<223> OTHER INFORMATION: Synthetic

<400> SEQUENCE: 59

```
Glu Ile Val Met Thr Gln Ser Pro Ala Thr Leu Ser Leu Ser Pro Gly
  1               5                  10                  15

Glu Arg Ala Thr Leu Ser Cys Arg Ala Ser Gln Ser Val Gly Ser Ser
             20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Val Ala Val Tyr Tyr Cys Leu Gln Arg Ser Asn Trp Pro Leu
                 85                  90                  95

Thr Phe Gly Gly Gly Thr Lys Val Glu Ile Lys Arg
            100                 105
```

<210> SEQ ID NO 60

<211> LENGTH: 108
<212> TYPE: PRT
<213> ORGANISM: Artificial Sequence
<220> FEATURE:
<223> OTHER INFORMATION: Synthetic

<400> SEQUENCE: 60

```
Glu Ile Glu Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Tyr Ala Thr Asn Arg Ala Thr Gly Ile Pro Asp Arg Phe Ser Gly
50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Gln Glu Ser Asn Trp Pro Leu
                85                  90                  95

Thr Phe Gly Gly Gly Thr Lys Val Glu Ile Lys Arg
            100                 105
```

<210> SEQ ID NO 61
<211> LENGTH: 108
<212> TYPE: PRT
<213> ORGANISM: Artificial Sequence
<220> FEATURE:
<223> OTHER INFORMATION: Synthetic

<400> SEQUENCE: 61

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Asn
            20                  25                  30

Leu Ala Trp Tyr Gln Gln Lys Pro Gly Gln Ala Pro Arg Leu Leu Ile
        35                  40                  45

Tyr Tyr Ala Ser Asn Arg Ala Thr Gly Ile Pro Asp Arg Phe Ser Gly
50                  55                  60

Ser Gly Ser Gly Thr Asp Phe Thr Leu Thr Ile Ser Ser Leu Glu Pro
65                  70                  75                  80

Glu Asp Val Gly Val Tyr Tyr Cys Gln Gln Glu Ser Asn Trp Pro Arg
                85                  90                  95

Thr Phe Gly Gln Gly Thr Lys Val Glu Ile Lys Arg
            100                 105
```

<210> SEQ ID NO 62
<211> LENGTH: 119
<212> TYPE: PRT
<213> ORGANISM: Artificial Sequence
<220> FEATURE:
<223> OTHER INFORMATION: Synthetic

<400> SEQUENCE: 62

```
Gln Glu Gln Leu Val Gln Ser Gly Gly Gly Leu Val Gln Pro Gly Gly
1               5                   10                  15

Ser Leu Arg Val Ser Cys Ala Ala Ser Gly Phe Thr Phe Ser Asp Tyr
            20                  25                  30

Val Ile Tyr Trp Val Arg Gln Thr Pro Gly Lys Gly Leu Glu Trp Val
        35                  40                  45
```

```
Gly Leu Ile Arg Arg Lys Ala Asn Gly Gly Thr Ala Glu Tyr Ala Ala
    50                  55                  60

Pro Val Lys Gly Arg Phe Thr Ile Ser Arg Asp Asp Ser Lys Asn Ile
 65                  70                  75                  80

Val Tyr Leu Gln Met Asn Ser Leu Lys Thr Glu Asp Thr Ala Val Tyr
                85                  90                  95

Phe Cys Thr Thr Asp Ile Arg Gly Trp Phe Asp Val Trp Gly Pro Gly
                100                 105                 110

Ala Leu Val Thr Val Ser Ser
        115
```

<210> SEQ ID NO 63
<211> LENGTH: 123
<212> TYPE: PRT
<213> ORGANISM: Artificial Sequence
<220> FEATURE:
<223> OTHER INFORMATION: Synthetic

<400> SEQUENCE: 63

```
Gln Val Gln Leu Val Gln Ser Gly Gly Gly Asp Trp Val Gln Pro Gly Gly
  1               5                  10                  15

Ser Leu Arg Leu Ser Cys Ala Ala Ser Gly Phe Ala Phe Asn Asn Ala
                20                  25                  30

Trp Met Asn Trp Val Arg Gln Ala Pro Gly Lys Gly Leu Val Trp Val
            35                  40                  45

Ala Arg Ile Lys Ser Lys Gly Asn Gly Glu Thr Pro Asp Tyr Ala Ser
    50                  55                  60

Ser Val Ile Gly Arg Phe Thr Ile Ser Arg Asp Asp Ser Lys Ser Thr
 65                  70                  75                  80

Leu Tyr Leu Gln Met Asn Asn Leu Lys Ile Asp Asp Thr Ala Val Tyr
                85                  90                  95

Tyr Cys Thr Thr Thr Pro Gly Gly Trp Thr His Ser Ser Phe Asn Val
                100                 105                 110

Trp Gly Pro Gly Ala Leu Val Thr Val Ser Ser
        115                 120
```

<210> SEQ ID NO 64
<211> LENGTH: 121
<212> TYPE: PRT
<213> ORGANISM: Artificial Sequence
<220> FEATURE:
<223> OTHER INFORMATION: Synthetic

<400> SEQUENCE: 64

```
Gln Val Gln Leu Val Gln Ser Gly Gly Gly Leu Val Gln Pro Gly Gly
  1               5                  10                  15

Ser Leu Arg Leu Ser Cys Ala Ala Ser Gly Phe Thr Phe Ser Asn Ala
                20                  25                  30

Trp Met Asn Trp Val Arg Gln Ala Pro Gly Lys Gly Leu Val Trp Val
            35                  40                  45

Ala Arg Ile Lys Ser Lys Ala Asn Gly Glu Thr Ala Asp Tyr Ala Ala
    50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                85                  90                  95

Tyr Cys Thr Thr Asp Val Asp Tyr Ser Gly Tyr Gly Tyr Trp Gly
                100                 105                 110
```

```
Gln Gly Ala Leu Val Thr Val Ser Ser
        115                 120

<210> SEQ ID NO 65
<211> LENGTH: 121
<212> TYPE: PRT
<213> ORGANISM: Artificial Sequence
<220> FEATURE:
<223> OTHER INFORMATION: Synthetic

<400> SEQUENCE: 65

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Val Trp Val
        35                  40                  45

Ala Arg Ile Lys Ser Lys Ala Asn Gly Glu Thr Thr Asp Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Val Asp Tyr Tyr Ser Gly Tyr Gly Tyr Trp Gly
            100                 105                 110

Gln Gly Ala Leu Val Thr Val Ser Ser
        115                 120

<210> SEQ ID NO 66
<211> LENGTH: 113
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Gln Ser Gly Gly Gly Leu Val Gln Pro Gly Gly
1               5                   10                  15

Ser Leu Arg Val Ser Cys Gly Ala Ser Gly Phe Ile Phe Ser Asn Ala
            20                  25                  30

Trp Met Asn Trp Val Arg Gln Ala Pro Gly Lys Gly Leu Val Trp Val
        35                  40                  45

Ala Arg Ile Lys Asn Lys Pro Asn Gly Glu Thr Ala Asp Tyr Ala Glu
    50                  55                  60

Ser Val Lys Gly Arg Phe Thr Ile Ser Arg Asp Asp Ser Lys Asn Thr
65                  70                  75                  80

Leu Phe Leu Gln Met Asn Ser Leu Lys Thr Glu Asp Thr Ala Val Tyr
                85                  90                  95

Tyr Cys Ala Met Asp Val Trp Gly Arg Gly Ala Leu Val Thr Val Ser
            100                 105                 110

Ser

<210> SEQ ID NO 67
<211> LENGTH: 121
<212> TYPE: PRT
<213> ORGANISM: Artificial Sequence
<220> FEATURE:
<223> OTHER INFORMATION: Synthetic
```

<400> SEQUENCE: 67

Gln Glu Gln Leu Val Gln Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Trp Met Asn Trp Val Arg Gln Ala Pro Gly Lys Gly Leu Asp Trp Val
        35                  40                  45

Gly Arg Ile Lys Asp Lys Val Asp Gly Gly Thr Ala Ala Tyr Ala Glu
    50                  55                  60

Ser Val Lys Gly Arg Phe Ile Ile Ser Arg Asp Asp Ser Lys Asn Thr
65                  70                  75                  80

Leu Tyr Leu Gln Met Asn Ser Leu Lys Ile Glu Asp Thr Ala Val Tyr
                85                  90                  95

Tyr Cys Ala Arg Ala Pro Tyr Trp Asp Asn Ser Leu Asp Val Trp Gly
            100                 105                 110

Arg Gly Ala Leu Val Thr Val Ser Ser
        115                 120

<210> SEQ ID NO 68
<211> LENGTH: 120
<212> TYPE: PRT
<213> ORGANISM: Artificial Sequence
<220> FEATURE:
<223> OTHER INFORMATION: Synthetic

<400> SEQUENCE: 68

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Asp Trp Val
        35                  40                  45

Gly Arg Ile Lys Asn Lys Ala Asp Gly Gly Ala Ala Ala Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Ile Glu Asp Thr Ala Val Tyr
                85                  90                  95

Tyr Cys Ala Ser Leu Gly His Ser Asp Gly Leu Asp Ser Trp Gly Gln
            100                 105                 110

Gly Ala Leu Val Thr Val Ser Ser
        115                 120

<210> SEQ ID NO 69
<211> LENGTH: 119
<212> TYPE: PRT
<213> ORGANISM: Artificial Sequence
<220> FEATURE:
<223> OTHER INFORMATION: Synthetic

<400> SEQUENCE: 69

Gln Glu Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Glu Met His Trp Val Arg Gln Ala Pro Gly Lys Gly Leu Glu Ser Val
        35                  40                  45

```
Ser Ile Ile Gly Gly Asp Ser Ser Tyr Thr His Tyr Val Asp Ser Val
    50                  55                  60

Lys Gly Arg Phe Thr Ile Ser Arg Asp Asn Ala Lys Asn Ser Leu Ser
 65                  70                  75                  80

Leu Gln Met Asn Ser Leu Arg Ala Ala Asp Thr Ala Val Tyr Tyr Cys
                 85                  90                  95

Thr Thr Leu Gly Arg Gly Ala Ile Pro Ile Arg Arg Trp Gly Gln Gly
            100                 105                 110

Ala Leu Val Thr Val Ser Ser
            115
```

<210> SEQ ID NO 70
<211> LENGTH: 119
<212> TYPE: PRT
<213> ORGANISM: Artificial Sequence
<220> FEATURE:
<223> OTHER INFORMATION: Synthetic

<400> SEQUENCE: 70

```
Gln Val Gln Leu Val Gln Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
             20                  25                  30

Glu Met His Trp Val Arg Gln Ala Pro Gly Lys Gly Leu Glu Ser Val
         35                  40                  45

Ser Ile Ile Gly Gly Asp Ser Ser Tyr Thr His Tyr Val Asp Ser Val
    50                  55                  60

Lys Gly Arg Phe Thr Ile Ser Arg Asp Asn Ala Lys Asn Ser Leu Ser
 65                  70                  75                  80

Leu Gln Met Asn Ser Leu Arg Ala Ala Asp Thr Ala Val Tyr Tyr Cys
                 85                  90                  95

Ala Arg Arg Gly Ser Trp Lys Gly Glu Leu Asp Val Trp Gly Arg Gly
            100                 105                 110

Ala Leu Val Thr Val Ser Ser
            115
```

<210> SEQ ID NO 71
<211> LENGTH: 122
<212> TYPE: PRT
<213> ORGANISM: Artificial Sequence
<220> FEATURE:
<223> OTHER INFORMATION: Synthetic

<400> SEQUENCE: 71

```
Gln Glu Gln Leu Val Gln Ser Gly Gly Gly Leu Val Gln Pro Gly Gly
  1               5                  10                  15

Ser Leu Arg Leu Ser Cys Val Thr Ser Gly Phe Thr Phe Ser Asp Tyr
             20                  25                  30

Glu Met Ala Trp Val Arg Gln Ala Thr Gly Lys Gly Leu Glu Trp Val
         35                  40                  45

Ser Ser Ile Ser Gln Pro Ser Gly Thr Asn Thr Tyr Tyr Leu Asp Pro
    50                  55                  60

Val Lys Gly Arg Phe Thr Ile Ser Arg Asp Asn Ala Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Thr Tyr Gly Ser Lys Leu Gly Tyr Phe Phe Tyr Tyr Trp
            100                 105                 110
```

```
Gly Gln Gly Ala Leu Val Thr Val Ser Ser
        115                 120

<210> SEQ ID NO 72
<211> LENGTH: 114
<212> TYPE: PRT
<213> ORGANISM: Artificial Sequence
<220> FEATURE:
<223> OTHER INFORMATION: Synthetic

<400> SEQUENCE: 72

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Pro Leu Ile Tyr Glu Val Ser Asn Arg Ala Ser Gly Val
    50                  55                  60

Pro Asp Arg Phe Ser Gly Ser Gly Ser Asp Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Ile Glu Phe Pro Tyr Ser Phe Gly Gln Gly Thr Lys Val Glu Ile
            100                 105                 110

Lys Arg

<210> SEQ ID NO 73
<211> LENGTH: 114
<212> TYPE: PRT
<213> ORGANISM: Artificial Sequence
<220> FEATURE:
<223> OTHER INFORMATION: Synthetic]

<400> SEQUENCE: 73

Asp Val Ala Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Glu Val Ser Asn Arg Ala Ser Gly Val
    50                  55                  60

Pro Asp Arg Phe Ser Gly Ser Gly Ser Asp Thr Asp Phe Thr Leu Lys
65                  70                  75                  80

Ile Ser Arg Val Glu Ala Glu Asp Val Gly Val Tyr Tyr Cys Met Gln
                85                  90                  95

Gly Ile Glu Phe Pro Tyr Ser Phe Gly Gln Gly Thr Lys Val Glu Ile
            100                 105                 110

Lys Arg

<210> SEQ ID NO 74
<211> LENGTH: 114
<212> TYPE: PRT
<213> ORGANISM: Artificial Sequence
<220> FEATURE:
<223> OTHER INFORMATION: Synthetic

<400> SEQUENCE: 74
```

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Glu Asp Gly Asn Thr Tyr Leu Asp Trp Tyr Leu Gln Lys Pro Gly Gln
        35                  40                  45

Ser Pro Gln Leu Leu Ile Tyr Glu Val Ser Asn Arg Ala Ser Gly Val
    50                  55                  60

Pro Asp Arg Phe Ser Gly Ser Gly Ser Asp Thr Asp Phe Thr Leu Lys
65              70                  75                  80

Ile Ser Arg Val Glu Ala Glu Asp Val Gly Val Tyr Tyr Cys Met Gln
                85                  90                  95

Gly Ile Glu Phe Pro Tyr Ser Phe Gly Gln Gly Thr Lys Val Glu Ile
            100                 105                 110

Lys Arg
```

<210> SEQ ID NO 75
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: s can be g or c

<400> SEQUENCE: 75
tcstctccac aggcgcccac tc                                          22

<210> SEQ ID NO 76
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: y can be t/u or c
<220> FEATURE:
<221> NAME/KEY: misc_feature
<223> OTHER INFORMATION: s can be g or c
<220> FEATURE:
<221> NAME/KEY: misc_feature
<223> OTHER INFORMATION: m can be a or c
<220> FEATURE:
<221> NAME/KEY: misc_feature
<223> OTHER INFORMATION: r can be g or a

<400> SEQUENCE: 76
tcctctmcry aggtgccmas tc                                          22

<210> SEQ ID NO 77
<211> LENGTH: 22
<212> TYPE: DNA
<213> ORGANISM: Artificial Sequence
<220> FEATURE:
<223> OTHER INFORMATION: Synthetic

<400> SEQUENCE: 77
tcctctccgc aggggcccac tc                                          22

<210> SEQ ID NO 78
<211> LENGTH: 20
<212> TYPE: DNA

<213> ORGANISM: Artificial Sequence
<220> FEATURE:
<223> OTHER INFORMATION: Synthetic

<400> SEQUENCE: 78
gtcccgtcct gggtcttgtc                                              20

<210> SEQ ID NO 79
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: r can be g or a

<400> SEQUENCE: 79
ctattttarr aggtgtccag tg                                           22

<210> SEQ ID NO 80
<211> LENGTH: 22
<212> TYPE: DNA
<213> ORGANISM: Artificial Sequence
<220> FEATURE:
<223> OTHER INFORMATION: Synthetic

<400> SEQUENCE: 80
ctcttttgaa aggtgtccag tg                                           22

<210> SEQ ID NO 81
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: w can be a or t/u
<220> FEATURE:
<221> NAME/KEY: misc_feature
<223> OTHER INFORMATION: y can be c or t/u

<400> SEQUENCE: 81
ctatwytaaa aggtgtccag tg                                           22

<210> SEQ ID NO 82
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: y can be t/u or c

<400> SEQUENCE: 82
agctcccaga tgggtcytgt cc                                           22

<210> SEQ ID NO 83
<211> LENGTH: 22
<212> TYPE: DNA
<213> ORGANISM: Artificial Sequence
<220> FEATURE:
<223> OTHER INFORMATION: Synthetic

<400> SEQUENCE: 83
tctcccccac aggagtctgt gc                                           22

<210> SEQ ID NO 84
<211> LENGTH: 18
<212> TYPE: DNA
<213> ORGANISM: Artificial Sequence
<220> FEATURE:
<223> OTHER INFORMATION: Synthetic

<400> SEQUENCE: 84
ggcctcccat ggggtgtc                                                 18

<210> SEQ ID NO 85
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: k can be g or t/u

<400> SEQUENCE: 85
ggacagcckg gaaggtgtgc                                               20

<210> SEQ ID NO 86
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: y can be t/u or c
<220> FEATURE:
<221> NAME/KEY: misc_feature
<223> OTHER INFORMATION: r can be g or a

<400> SEQUENCE: 86
tccaatytca ggtgccarat gt                                            22

<210> SEQ ID NO 87
<211> LENGTH: 21
<212> TYPE: DNA
<213> ORGANISM: Artificial Sequence
<220> FEATURE:
<223> OTHER INFORMATION: Synthetic

<400> SEQUENCE: 87
atttcaggat ccagtgggga t                                             21

<210> SEQ ID NO 88
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: y can be t/u or c

<400> SEQUENCE: 88
tccaatttca gataccacyg ga                                            22

<210> SEQ ID NO 89
<211> LENGTH: 22
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<223> OTHER INFORMATION: r can be g or a

<400> SEQUENCE: 89
tccaatctca grtaccrccg ga                                    22

<210> SEQ ID NO 90
<211> LENGTH: 21
<212> TYPE: DNA
<213> ORGANISM: Artificial Sequence
<220> FEATURE:
<223> OTHER INFORMATION: Synthetic

<400> SEQUENCE: 90
tgggtctcgg tgcccgtcag g                                     21

<210> SEQ ID NO 91
<211> LENGTH: 21
<212> TYPE: DNA
<213> ORGANISM: Artificial Sequence
<220> FEATURE:
<223> OTHER INFORMATION: Synthetic

<400> SEQUENCE: 91
tggatctctg gtgcctgtgg g                                     21

<210> SEQ ID NO 92
<211> LENGTH: 21
<212> TYPE: DNA
<213> ORGANISM: Artificial Sequence
<220> FEATURE:
<223> OTHER INFORMATION: Synthetic

<400> SEQUENCE: 92
tggatctctg atgccagggc a                                     21

<210> SEQ ID NO 93
<211> LENGTH: 21
<212> TYPE: DNA
<213> ORGANISM: Artificial Sequence
<220> FEATURE:
<223> OTHER INFORMATION: Synthetic

<400> SEQUENCE: 93
tgtgctccag gctgcaatgg g                                     21

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
gaggcagttc cagatttcaa                                       20

<210> SEQ ID NO 95
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: r can be g or a

```
<400> SEQUENCE: 95
acaggtgtcc actcggaggt ccagctggtr cagtc                           35

<210> SEQ ID NO 96
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: w can be a or t/u

<400> SEQUENCE: 96
acaggtgtcc actcgcaggw gcagctggtg cagtc                           35

<210> SEQ ID NO 97
<211> LENGTH: 37
<212> TYPE: DNA
<213> ORGANISM: Artificial Sequence
<220> FEATURE:
<223> OTHER INFORMATION: Synthetic

<400> SEQUENCE: 97
acaggtgtcc actcgcaggt gaccttgaag gagtctg                         37

<210> SEQ ID NO 98
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: r can be g or a
<220> FEATURE:
<221> NAME/KEY: misc_feature
<223> OTHER INFORMATION: y can be t/u or c

<400> SEQUENCE: 98
acaggtgtcc actcggargt gcagytggtg gagtctg                         37

<210> SEQ ID NO 99
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: s can be g or c

<400> SEQUENCE: 99
acaggtgtcc actcgcagst gcagctgcag gagtcgg                         37

<210> SEQ ID NO 100
<211> LENGTH: 37
<212> TYPE: DNA
<213> ORGANISM: Artificial Sequence
<220> FEATURE:
<223> OTHER INFORMATION: Synthetic

<400> SEQUENCE: 100
acaggtgtcc actcgcagct gcagctgcag ctgcagg                         37

<210> SEQ ID NO 101
```

```
<211> LENGTH: 37
<212> TYPE: DNA
<213> ORGANISM: Artificial Sequence
<220> FEATURE:
<223> OTHER INFORMATION: Synthetic

<400> SEQUENCE: 101
acaggtgtcc actcggaggt gcagctggtg cagtctg                              37

<210> SEQ ID NO 102
<211> LENGTH: 37
<212> TYPE: DNA
<213> ORGANISM: Artificial Sequence
<220> FEATURE:
<223> OTHER INFORMATION: Synthetic

<400> SEQUENCE: 102
acaggtgtcc actcgcaggt gcagctgcag gagtcag                              37

<210> SEQ ID NO 103
<211> LENGTH: 41
<212> TYPE: DNA
<213> ORGANISM: Artificial Sequence
<220> FEATURE:
<223> OTHER INFORMATION: Synthetic

<400> SEQUENCE: 103
gatgggccct tggtggatgc tgaggagacg gtgaccaggg c                         41

<210> SEQ ID NO 104
<211> LENGTH: 41
<212> TYPE: DNA
<213> ORGANISM: Artificial Sequence
<220> FEATURE:
<223> OTHER INFORMATION: Synthetic

<400> SEQUENCE: 104
gatgggccct tggtggatgc tgaggagatg gtgattgggg t                         41

<210> SEQ ID NO 105
<211> LENGTH: 42
<212> TYPE: DNA
<213> ORGANISM: Artificial Sequence
<220> FEATURE:
<223> OTHER INFORMATION: Synthetic

<400> SEQUENCE: 105
gatggggccc ttggtggatg ctgaagagac ggtgaccctg ag                        42

<210> SEQ ID NO 106
<211> LENGTH: 41
<212> TYPE: DNA
<213> ORGANISM: Artificial Sequence
<220> FEATURE:
<223> OTHER INFORMATION: Synthetic

<400> SEQUENCE: 106
gatgggccct tggtggatgc tgaggagacg gtgaccagga c                         41

<210> SEQ ID NO 107
<211> LENGTH: 41
<212> TYPE: DNA
<213> ORGANISM: Artificial Sequence
<220> FEATURE:
<223> OTHER INFORMATION: Synthetic

<400> SEQUENCE: 107
```
gatgggccct tggtggatgc tgaggagacg gtgaccagaa c                           41

<210> SEQ ID NO 108
<211> LENGTH: 41
<212> TYPE: DNA
<213> ORGANISM: Artificial Sequence
<220> FEATURE:
<223> OTHER INFORMATION: Synthetic

<400> SEQUENCE: 108
gatgggccct tggtggatgc tgaggagacg gtgacgacga c                           41

<210> SEQ ID NO 109
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: y can be t/u or c
<220> FEATURE:
<221> NAME/KEY: misc_feature
<223> OTHER INFORMATION: w can be t/u or a

<400> SEQUENCE: 109
cttacagacg ctcgctgcga catycagatg wcccagtctc                             40

<210> SEQ ID NO 110
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: y can be t/u or c

<400> SEQUENCE: 110
cttacagacg ctcgctgcga taytgtgatg ayccagactc                             40

<210> SEQ ID NO 111
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: y can be t/u or c
<220> FEATURE:
<221> NAME/KEY: misc_feature
<223> OTHER INFORMATION: r can be g or a

<400> SEQUENCE: 111
cttacagacg ctcgctgcga tgttgyratg actcagtctc                             40

<210> SEQ ID NO 112
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: w can be a or t/u
<220> FEATURE:
<221> NAME/KEY: misc_feature
<223> OTHER INFORMATION: r can be a or g

<400> SEQUENCE: 112
cttacagacg ctcgctgcga aatwgtratg acgcagtctc           40

<210> SEQ ID NO 113
<211> LENGTH: 40
<212> TYPE: DNA
<213> ORGANISM: Artificial Sequence
<220> FEATURE:
<223> OTHER INFORMATION: Synthetic

<400> SEQUENCE: 113
cttacagacg ctcgctgcca agttatattg actcagtctc           40

<210> SEQ ID NO 114
<211> LENGTH: 39
<212> TYPE: DNA
<213> ORGANISM: Artificial Sequence
<220> FEATURE:
<223> OTHER INFORMATION: Synthetic

<400> SEQUENCE: 114
cttacagacg ctcgctgcct ggatctctgg tgtctgtgg            39

<210> SEQ ID NO 115
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: m can be a or c

<400> SEQUENCE: 115
cttacagacg ctcgctgccc tttggatctc tgmtgccagg           40

<210> SEQ ID NO 116
<211> LENGTH: 38
<212> TYPE: DNA
<213> ORGANISM: Artificial Sequence
<220> FEATURE:
<223> OTHER INFORMATION: Synthetic

<400> SEQUENCE: 116
cttacagacg ctcgctgctg ggttccagtc tccaaggg             38

<210> SEQ ID NO 117
<211> LENGTH: 38
<212> TYPE: DNA
<213> ORGANISM: Artificial Sequence
<220> FEATURE:
<223> OTHER INFORMATION: Synthetic

<400> SEQUENCE: 117
cttacagacg ctcgctgctg tgctccaggc tgcaatgg             38

<210> SEQ ID NO 118
<211> LENGTH: 34
<212> TYPE: DNA
<213> ORGANISM: Artificial Sequence
<220> FEATURE:
<223> OTHER INFORMATION: Synthetic

<400> SEQUENCE: 118
atggtgcagc caccgtacgt ttgatctcca gctt                 34

```
<210> SEQ ID NO 119
<211> LENGTH: 34
<212> TYPE: DNA
<213> ORGANISM: Artificial Sequence
<220> FEATURE:
<223> OTHER INFORMATION: Synthetic

<400> SEQUENCE: 119
atggtgcagc caccgtacgt ttgatttcca cctt                              34

<210> SEQ ID NO 120
<211> LENGTH: 34
<212> TYPE: DNA
<213> ORGANISM: Artificial Sequence
<220> FEATURE:
<223> OTHER INFORMATION: Synthetic

<400> SEQUENCE: 120
atggtgcagc caccgtacgt ttgatctcca cttt                              34

<210> SEQ ID NO 121
<211> LENGTH: 34
<212> TYPE: DNA
<213> ORGANISM: Artificial Sequence
<220> FEATURE:
<223> OTHER INFORMATION: Synthetic

<400> SEQUENCE: 121
atggtgcagc caccgtacgt ttgatatcca gttt                              34

<210> SEQ ID NO 122
<211> LENGTH: 34
<212> TYPE: DNA
<213> ORGANISM: Artificial Sequence
<220> FEATURE:
<223> OTHER INFORMATION: Synthetic

<400> SEQUENCE: 122
atggtgcagc caccgtacgt ttaatctcca gtcg                              34
```